(12) United States Patent
Jang et al.

(10) Patent No.: US 12,128,076 B2
(45) Date of Patent: Oct. 29, 2024

(54) COMPOSITION COMPRISING PROBIOTICS AND POLYPEPTIDE HAVING BINDING AFFINITY FOR IGE AND USE THEREOF

(71) Applicant: GI INNOVATION, INC., Seoul (KR)

(72) Inventors: Myoung Ho Jang, Seoul (KR); Young Chul Sung, Seoul (KR); Zungyoon Yang, Incheon (KR)

(73) Assignee: GI Innovation, Inc., Seoul (KR)

( * ) Notice: Subject to any disclaimer, the term of this patent is extended or adjusted under 35 U.S.C. 154(b) by 980 days.

(21) Appl. No.: 16/959,016

(22) PCT Filed: Jan. 14, 2019

(86) PCT No.: PCT/KR2019/000524
§ 371 (c)(1),
(2) Date: Jun. 29, 2020

(87) PCT Pub. No.: WO2019/139434
PCT Pub. Date: Jul. 18, 2019

(65) Prior Publication Data
US 2022/0347236 A1 Nov. 3, 2022

(30) Foreign Application Priority Data

Jan. 12, 2018 (KR) .......................... 10-2018-0004421

(51) Int. Cl.
*A61K 35/745* (2015.01)
*A61K 9/00* (2006.01)
(Continued)

(52) U.S. Cl.
CPC .......... *A61K 35/745* (2013.01); *A61K 9/0019* (2013.01); *A61K 9/0056* (2013.01);
(Continued)

(58) Field of Classification Search
CPC .. A61K 9/0056; A61K 35/745; A61K 35/747; A61K 35/744; A61K 38/1774;
(Continued)

(56) References Cited

U.S. PATENT DOCUMENTS

2010/0028263 A1* 2/2010 Schiffer-Mannioui ...................... A23L 33/135 435/375
2013/0243750 A1 9/2013 Scheerens et al.
2018/0044402 A1* 2/2018 Sakamoto .............. C12N 15/09

FOREIGN PATENT DOCUMENTS

CN 1505678 A 6/2004
CN 103169733 A 6/2013
(Continued)

OTHER PUBLICATIONS

English translation of Park et al. (WO-2012169735-A2). (Year: 2012).*
(Continued)

*Primary Examiner* — Gary B Nickol
*Assistant Examiner* — Amelia Nicole Dickens
(74) *Attorney, Agent, or Firm* — Sughrue Mion, PLLC

(57) ABSTRACT

A composition containing, as active ingredients, probiotics and a polypeptide with a binding ability to IgE is disclosed. In particular, a synergistic effect of remarkably decreasing food allergy was identified at the time of combined administration of probiotics and a recombinant protein containing an extracellular domain of an alpha subunit of an IgE Fc receptor. Therefore, it is expected that the composition is highly industrially applicable due to being able to exhibit a remarkable therapeutic effect on an IgE-mediated allergic disease as compared with conventional pharmaceutical compositions.

6 Claims, 35 Drawing Sheets
Specification includes a Sequence Listing.

(51) Int. Cl.
*A61K 9/14* (2006.01)
*A61K 9/19* (2006.01)
*A61K 35/744* (2015.01)
*A61K 35/747* (2015.01)
*A61K 38/17* (2006.01)
*A61K 39/395* (2006.01)
*A61P 37/08* (2006.01)
*C07K 14/735* (2006.01)
*C07K 16/42* (2006.01)

(52) U.S. Cl.
CPC .................. *A61K 9/14* (2013.01); *A61K 9/19* (2013.01); *A61K 35/744* (2013.01); *A61K 35/747* (2013.01); *A61K 38/1774* (2013.01); *A61K 39/39566* (2013.01); *A61P 37/08* (2018.01); *C07K 14/70535* (2013.01); *C07K 16/4291* (2013.01); *C07K 2317/52* (2013.01); *C07K 2317/60* (2013.01); *C07K 2317/92* (2013.01); *C07K 2319/30* (2013.01)

(58) Field of Classification Search
CPC .. A61K 9/19; A61K 9/0019; A61K 39/39566; C07K 14/70503; C07K 16/4291; C07K 2317/52; C07K 2319/30; C07K 14/70535; C07K 2317/60; C07K 2317/92; A61P 37/08

See application file for complete search history.

(56) References Cited

FOREIGN PATENT DOCUMENTS

| | | | |
|---|---|---|---|
| CN | 102695956 B | 12/2015 | |
| JP | 9-2959 A | 1/1997 | |
| JP | 10-309178 A | 11/1998 | |
| JP | 2000-95697 A | 4/2000 | |
| JP | 2009-67679 A | 4/2009 | |
| JP | 2010-513245 A | 4/2010 | |
| JP | 2010-518815 A | 6/2010 | |
| JP | 2010-531134 A | 9/2010 | |
| JP | 2011-505349 A | 2/2011 | |
| JP | 2011-510684 A | 4/2011 | |
| KR | 2003-0082950 A | 10/2003 | |
| KR | 10-2012-0116400 A | 10/2012 | |
| KR | 10-2012-0135865 A | 12/2012 | |
| RU | 2 336 886 C2 | 10/2008 | |
| RU | 2 605 293 C2 | 12/2016 | |
| WO | WO-0137865 A1 * | 5/2001 | ........... A23L 33/135 |
| WO | 02/086102 A1 | 10/2002 | |
| WO | 2004/002501 A1 | 1/2004 | |
| WO | 2007/077812 A1 | 7/2007 | |
| WO | WO-2008028068 A2 * | 3/2008 | ....... C07K 14/70535 |
| WO | 2008/071751 A1 | 6/2008 | |
| WO | 2008/099178 A2 | 8/2008 | |
| WO | 2008/147143 A2 | 12/2008 | |
| WO | 2009/068997 A1 | 6/2009 | |
| WO | 2009/100331 A2 | 8/2009 | |
| WO | 2011/056606 A1 | 5/2011 | |
| WO | 2011/110918 A1 | 9/2011 | |
| WO | WO-2012169735 A2 * | 12/2012 | ......... A61K 38/1774 |
| WO | 2016/133197 A1 | 8/2016 | |
| WO | WO-2016141454 A1 * | 9/2016 | ............. A61K 35/74 |
| WO | WO-2019135666 A1 * | 7/2019 | ............. A23L 33/18 |
| WO | WO-2019135668 A1 * | 7/2019 | ............. A23L 33/18 |

OTHER PUBLICATIONS

Dantzer and Wood. "The use of omalizumab in allergen immunotherapy", Jan. 5, 2018, Clinical & Experimental Allergy, vol. 48, Issue 3, p. 232-240 (Year: 2018).*
Mennini et al. "Probiotics in Asthma and Allergy Prevention", Jul. 31, 2017, Frontiers in Pediatrics, vol. 5 Article 165, p. 1-5. (Year: 2017).*
Ozdemir "Various effects of different probiotic strains in allergic disorders: an update from laboratory and clinical data", 2010, British Society for Immunology, Clinical and Experimental Immunology, vol. 160, p. 295-304. (Year: 2010).*
Tang et al. "Administration of a probiotic with peanut oral immunotherapy: A randomized trial", Jan. 13, 2015, Journal of Allergy and Clinical Immunology, vol. 135, Issue 3, p. 737-744. (Year: 2015).*
Meijerik et al. "Immunomodulatory effects of potential probiotics in a mouse peanut sensitization model", May 24, 2012, FEMS Immunology & Medical Microbiology, vol. 65, p. 488-496. (Year: 2012).*
English machine translation of WO 2019135666 A1. (Year: 2019).*
English machine translation of WO 2019135668 A1. (Year: 2019).*
Communication dated Jun. 7, 2022 from the Russian Patent Office in Russian Application No. 2020122021.
M.S.P. De Azevedo et al., "Immunotherapy of allergic diseases using probiotics or recombinant probiotics" Journal of Applied Microbiology, 2013, vol. 115, pp. 319-333 (15 pages total).
Mimi L.K. Tang, et al., "Administration of a probiotic with peanut oral immunotherapy: A randomized trial", Journal of Allergy and Clinical Immunology, 2015, vol. 135, No. 3, pp. 737-744 (16 pages total).
NCBI, Genbank Accession, No. 1J89_A, "Chain A, High Affinity Immunoglobulin Epsilon Receptor Alpha-Subunit", SPO20-016-CL, Oct. 10, 2012, 4 pages total.

* cited by examiner

[FIG. 1]
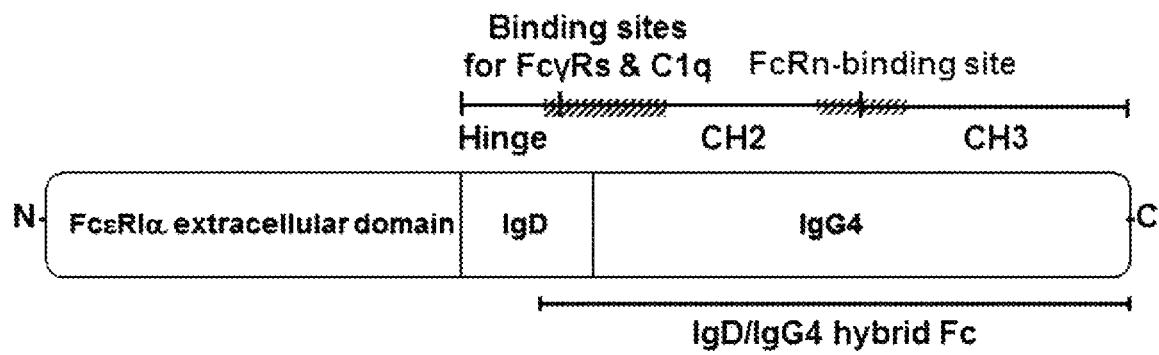
[FIG. 2]
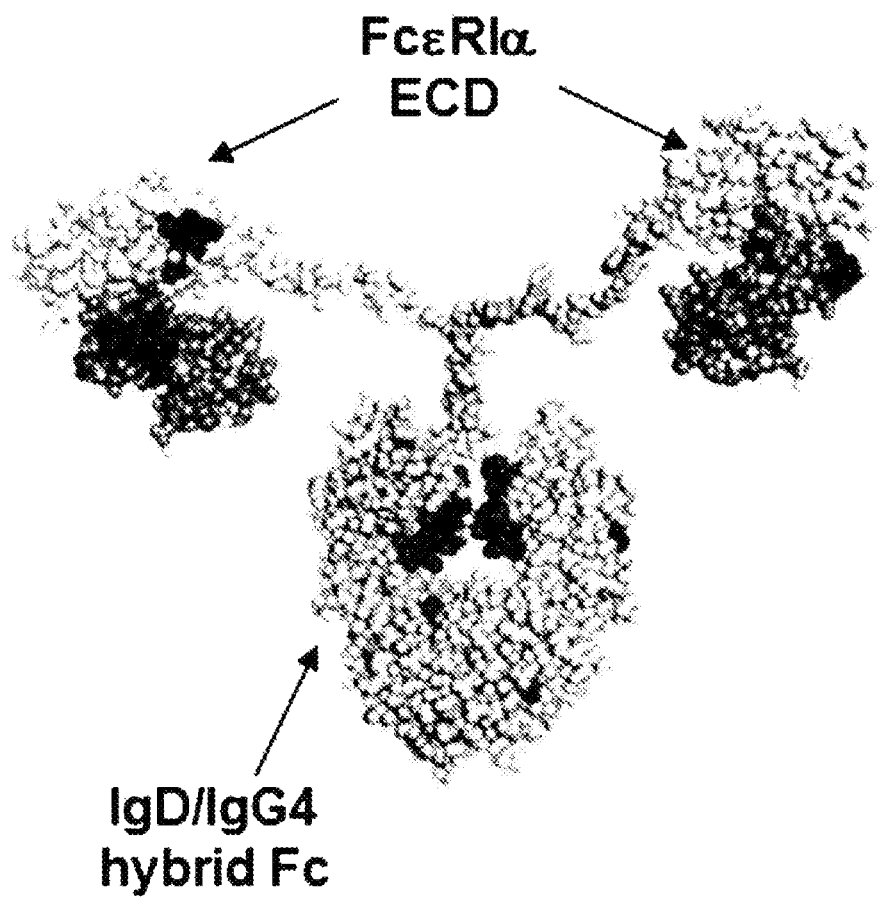

[FIG. 3A]
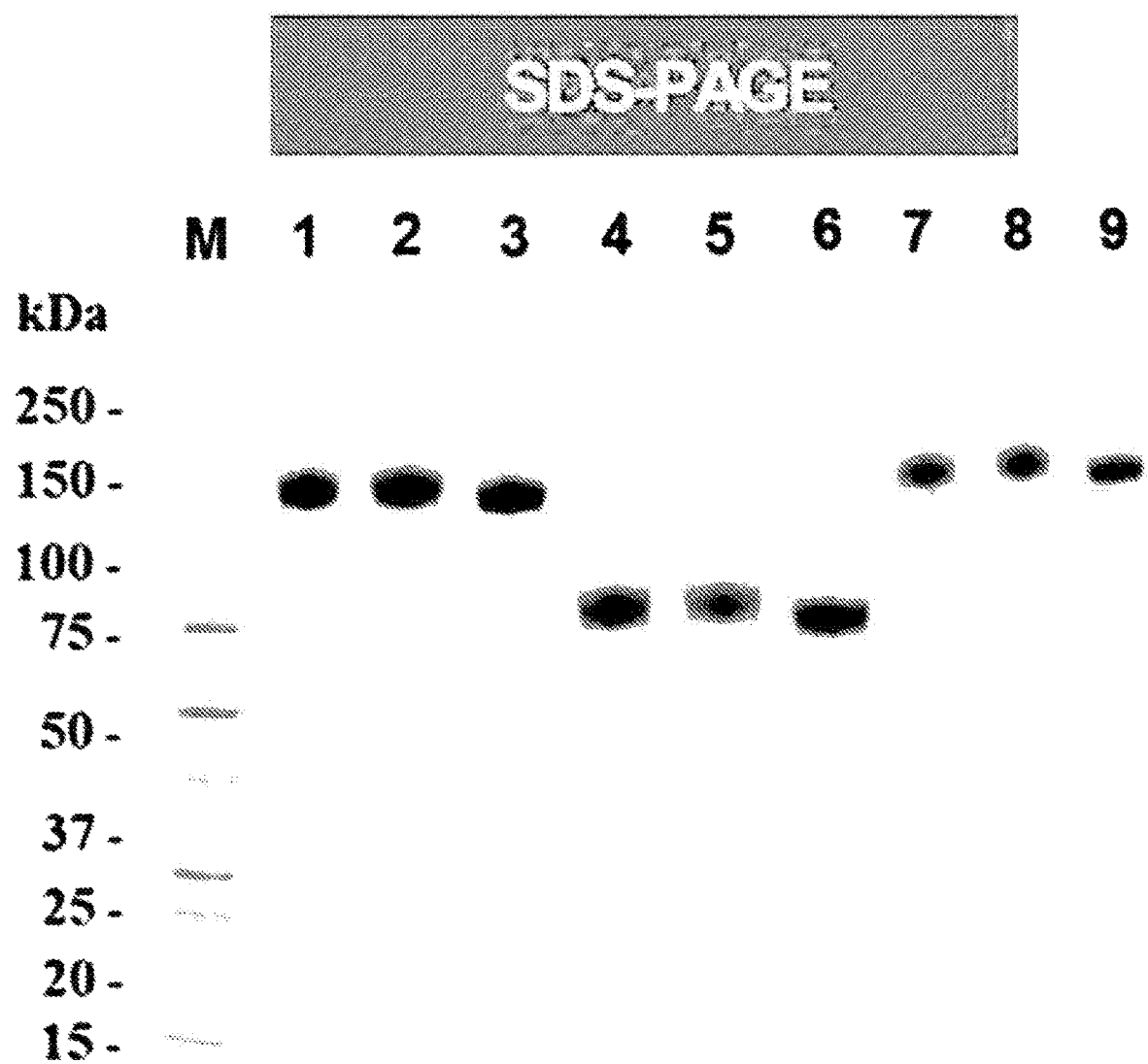

[FIG. 3B]

| Lane # | Sample | Purification | Purity (SE-HPLC) | Sample condition | |
|---|---|---|---|---|---|
| M | Protein standard | | . | . | . |
| 1 | FcεR1α ECD-Fc3 | One-step (Protein-A column) purification | 94.5% | . | Non-reducing |
| 2 | FcεR1α ECD-Fc3+2,6 ST | | 93.7% | | |
| 3 | FcεR1α ECD-Fc2+2,6 ST | | 93.2% | | |
| 4 | FcεR1α ECD-Fc3 | | 94.5% | . | Reducing |
| 5 | FcεR1α ECD-Fc3+2,6 ST | | 93.7% | | |
| 6 | FcεR1α ECD-Fc2+2,6 ST | | 93.2% | | |
| 7 | FcεR1α ECD-Fc3 | | 94.5% | Freezing/ Thawing test | Non-reducing |
| 8 | FcεR1α ECD-Fc3+2,6 ST | | 93.7% | | |
| 9 | FcεR1α ECD-Fc2+2,6 ST | | 93.2% | | |

[FIG. 4]
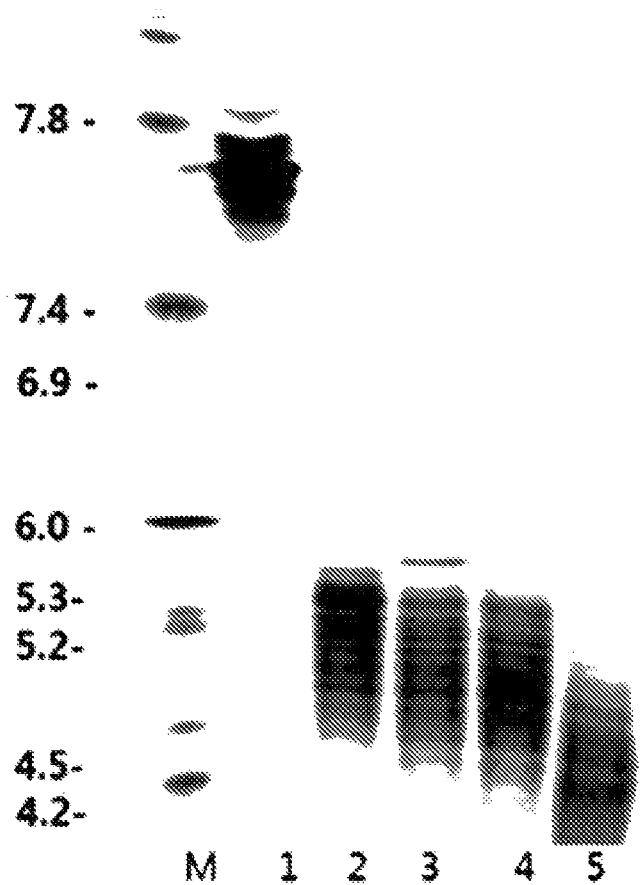
| Lane | Loading sample | Theoretical pI |
|---|---|---|
| M | Marker (SERVA pH3-10, 5uL) | |
| 1 | Xolair | 7.03 |
| 2 | FcεRIα ECD-FC2 | 5.62 |
| 3 | FcεRIα ECD-FC2+2,6 ST | 5.62 |
| 4 | FcεRIα ECD-FC3 | 5.63 |
| 5 | FcεRIα ECD-FC3+2,6 ST | 5.63 |

[FIG. 5]
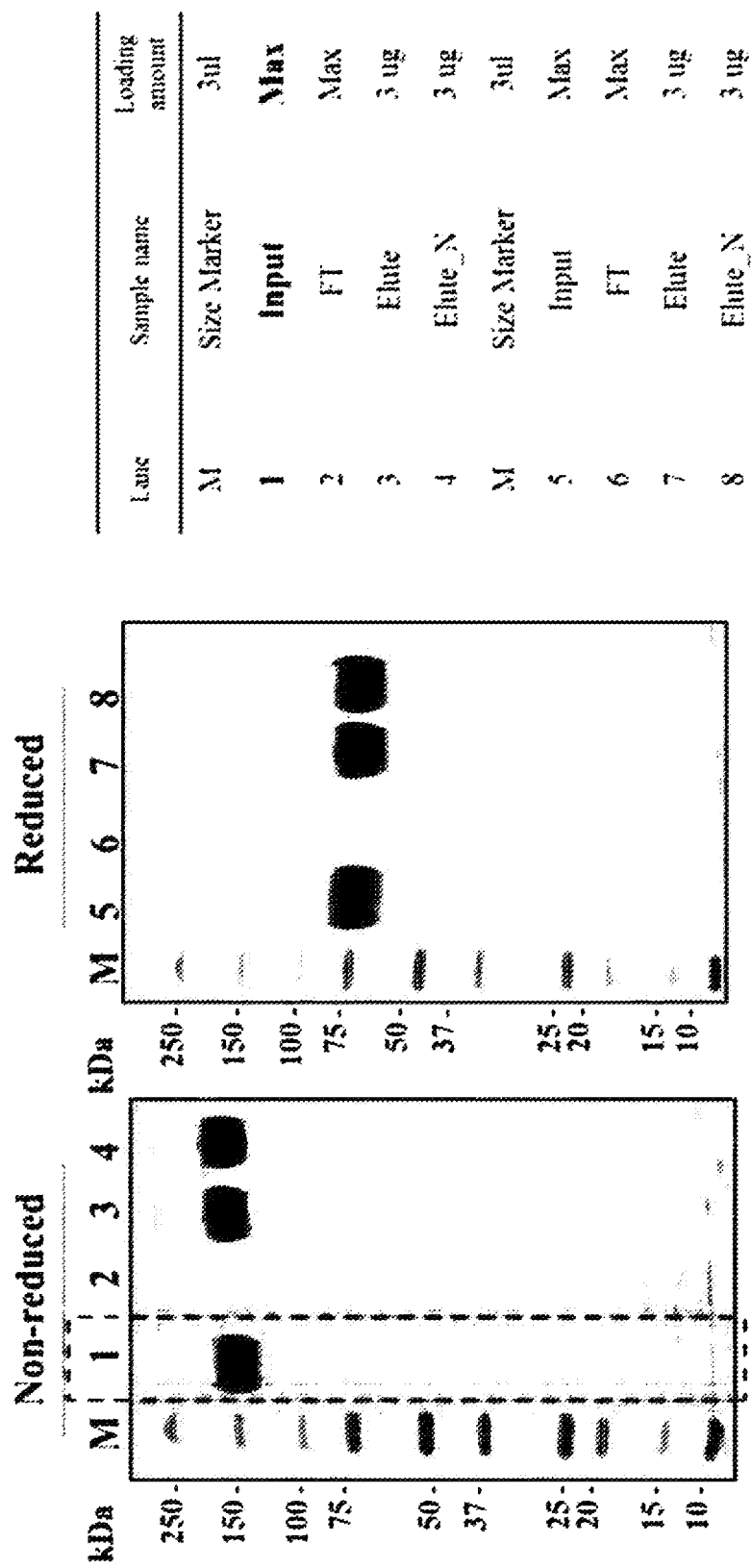

[FIG. 6]
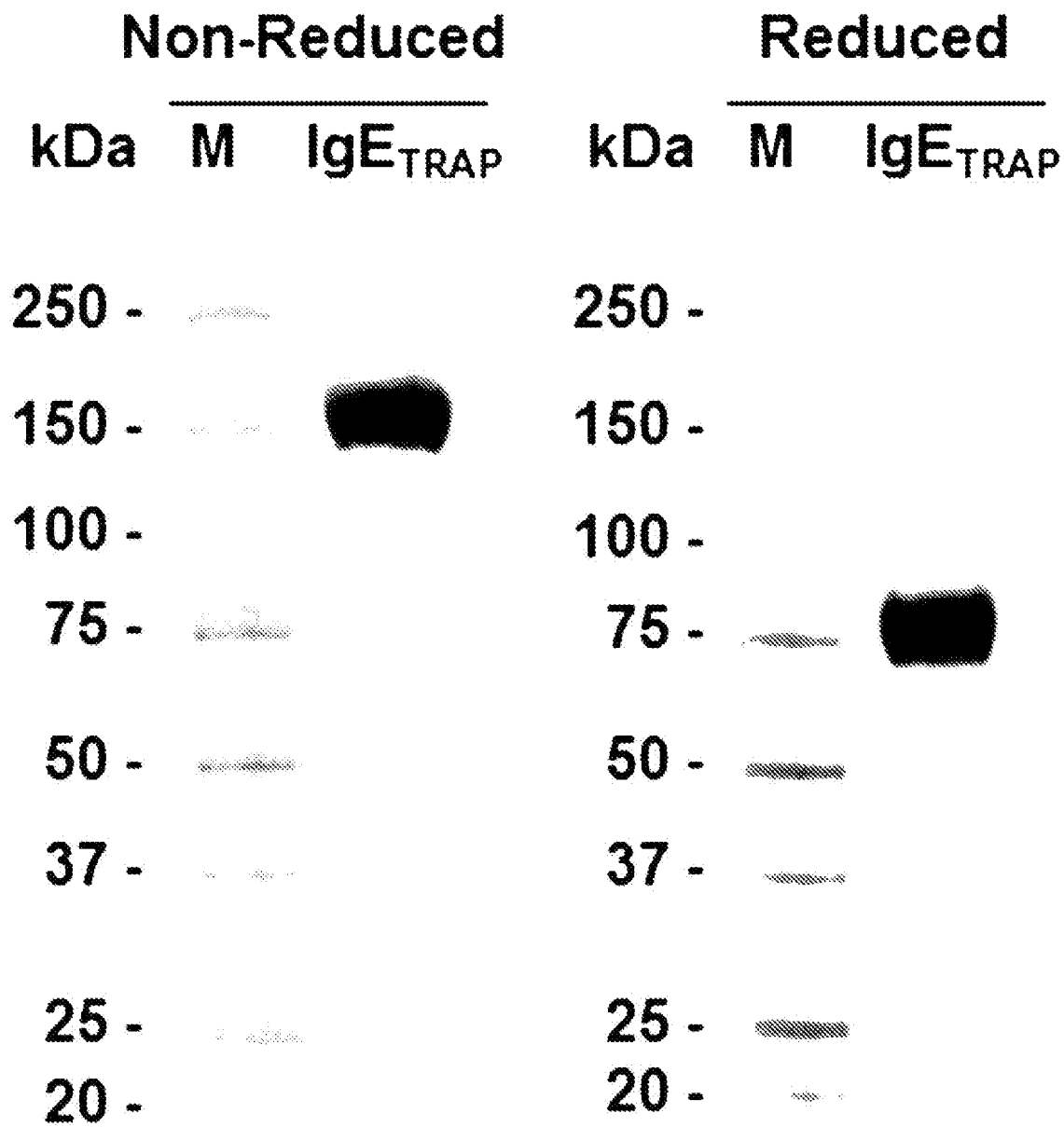

[FIG. 7]
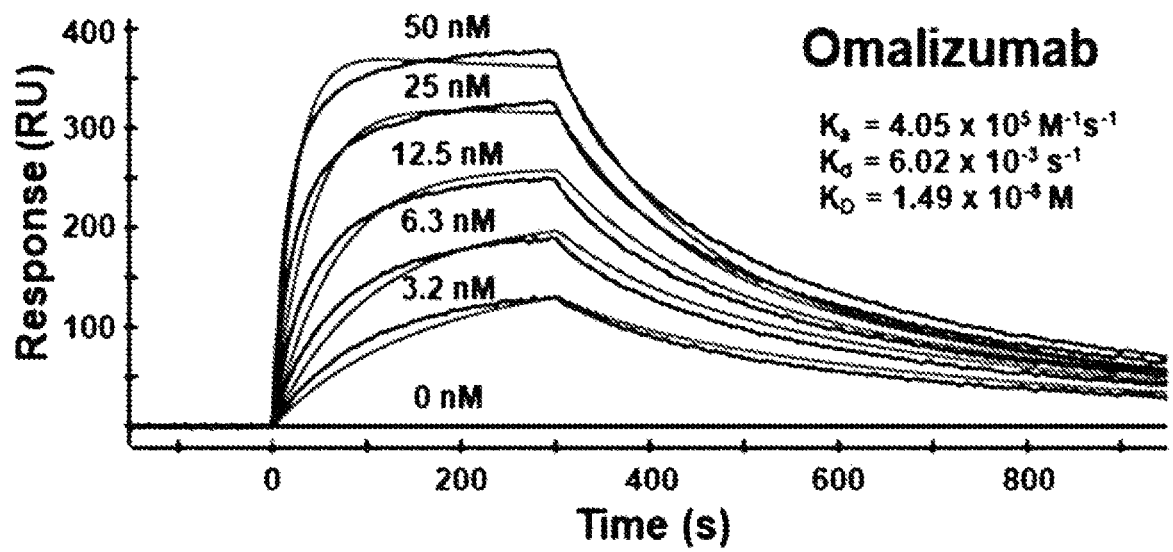
[FIG. 8]
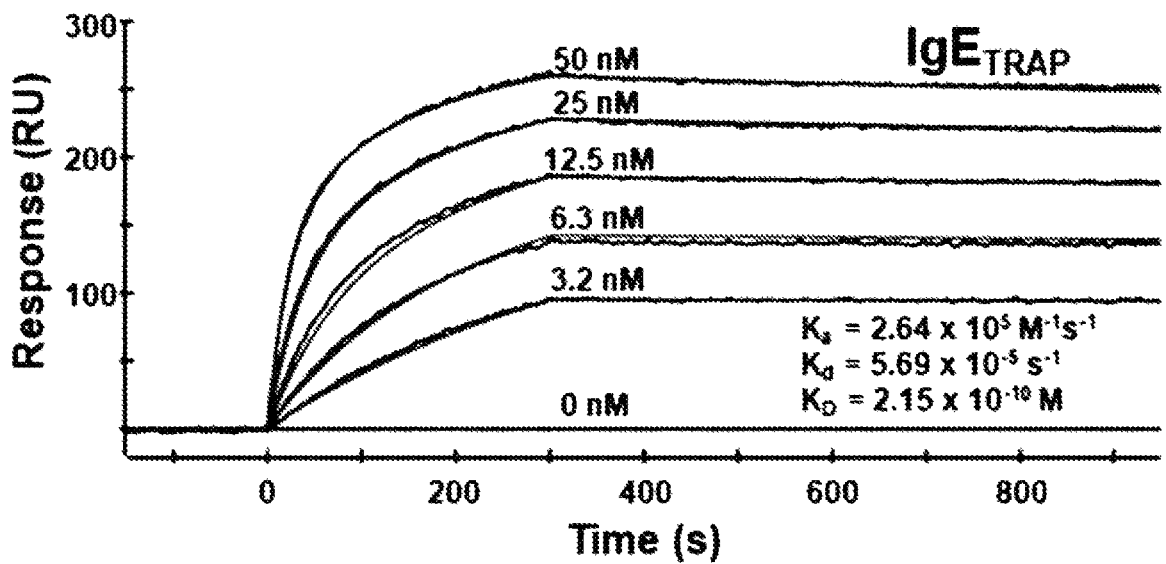

[FIG. 9]
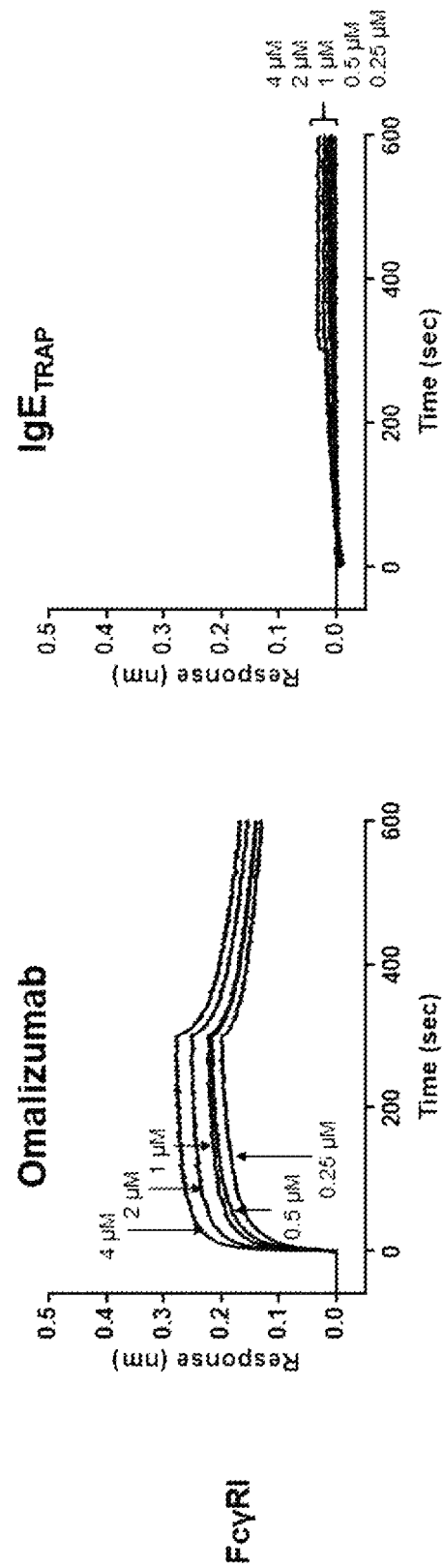

[FIG. 10]
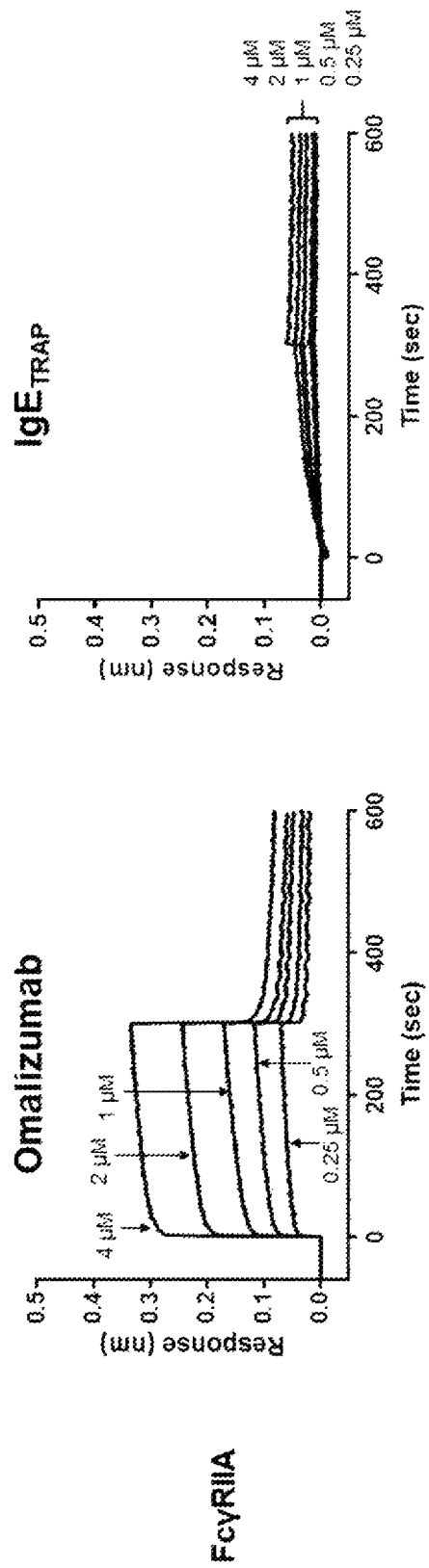

[FIG. 11]
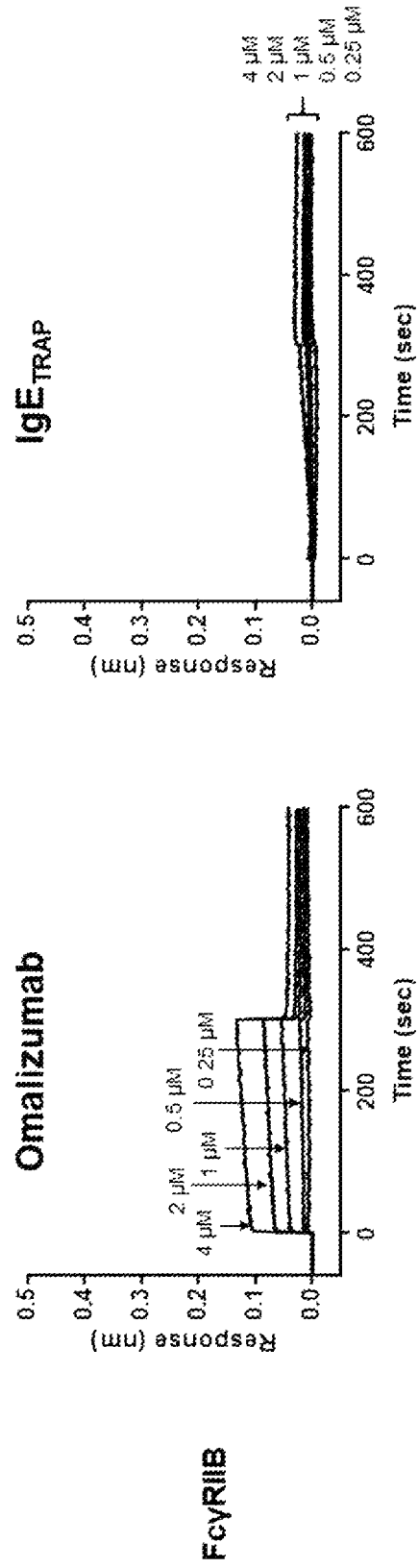

[FIG. 12]
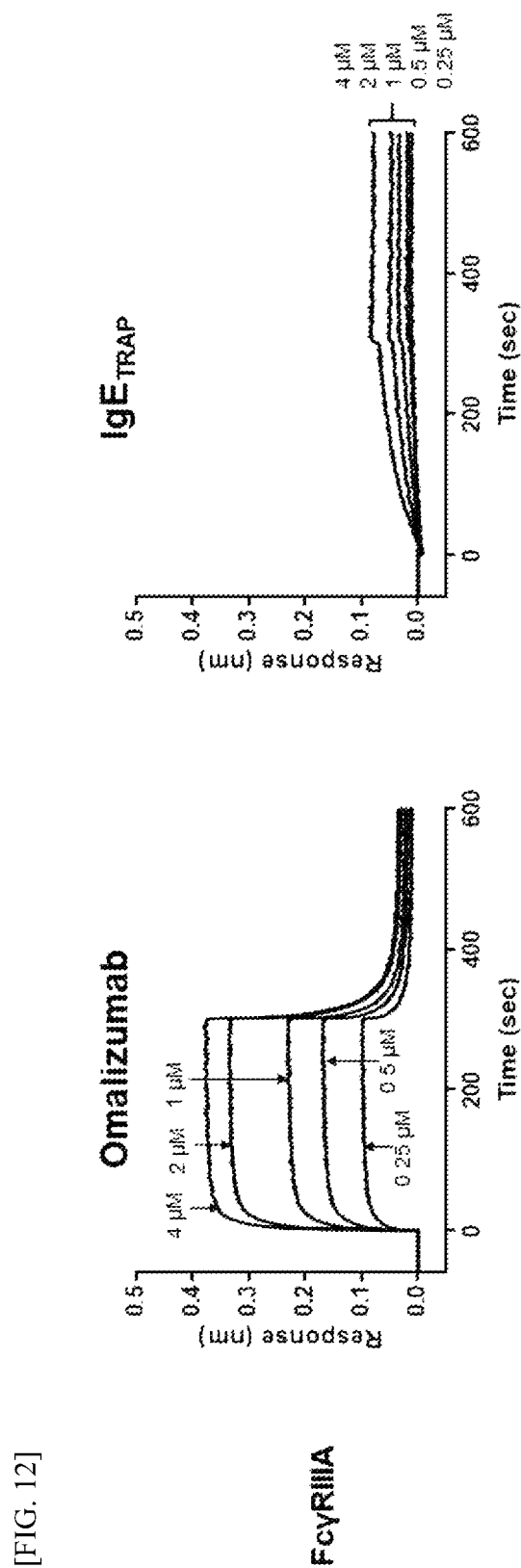

[FIG. 13]
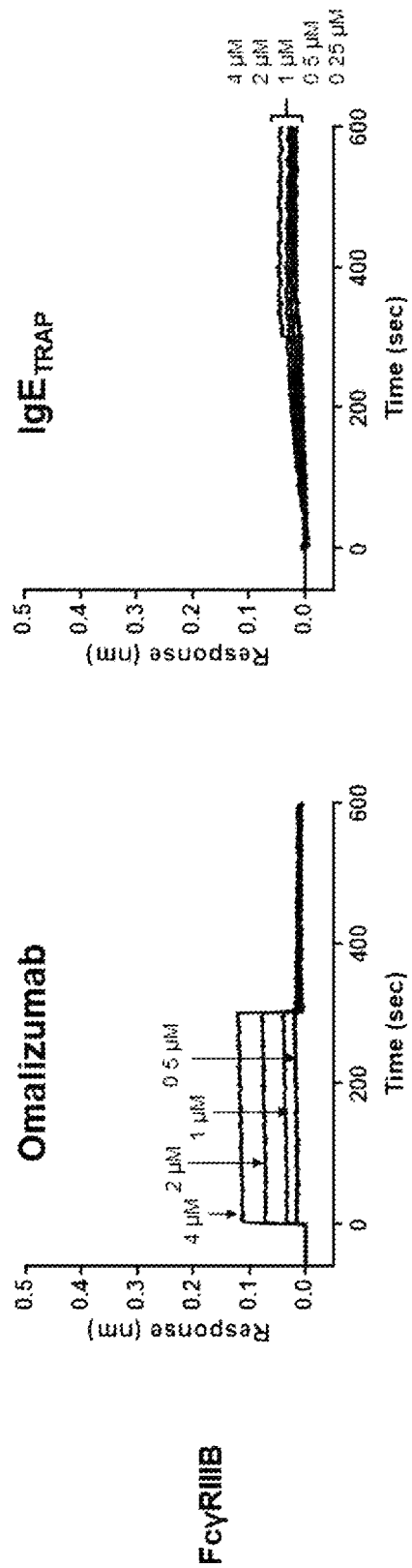

[FIG. 15B]
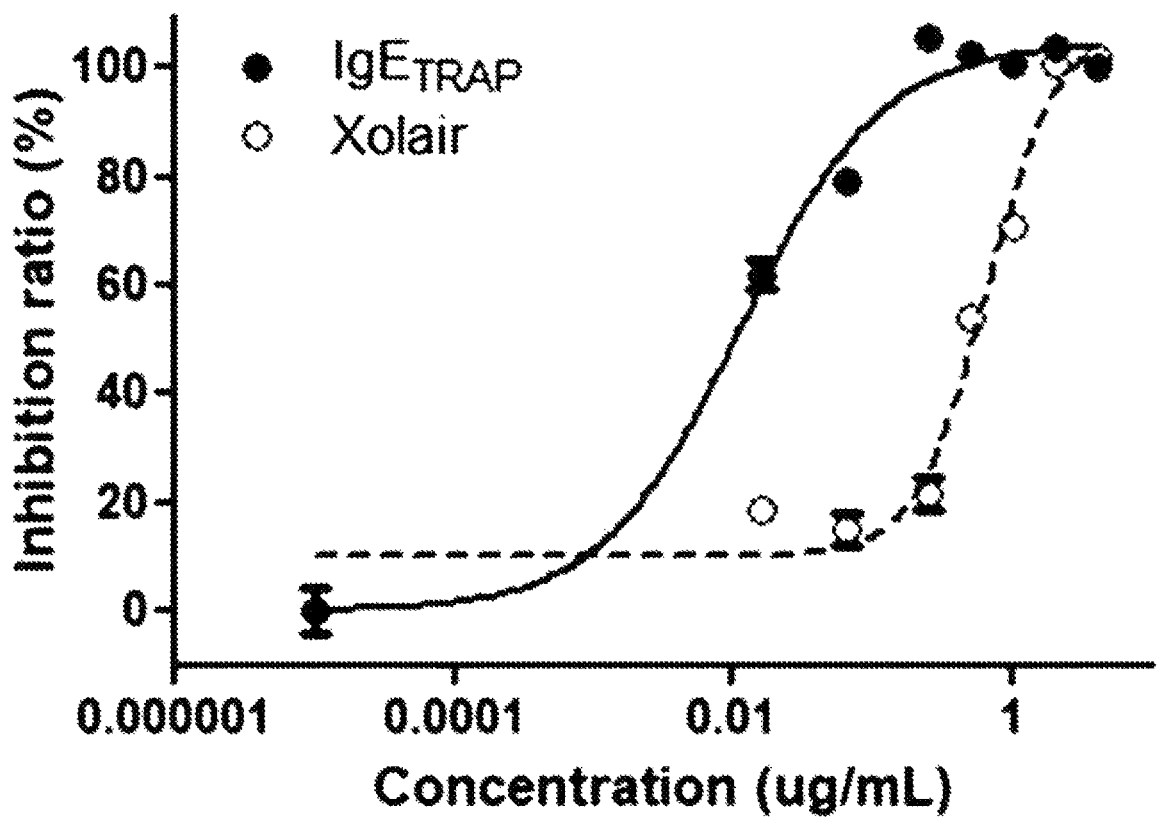

[FIG. 17]
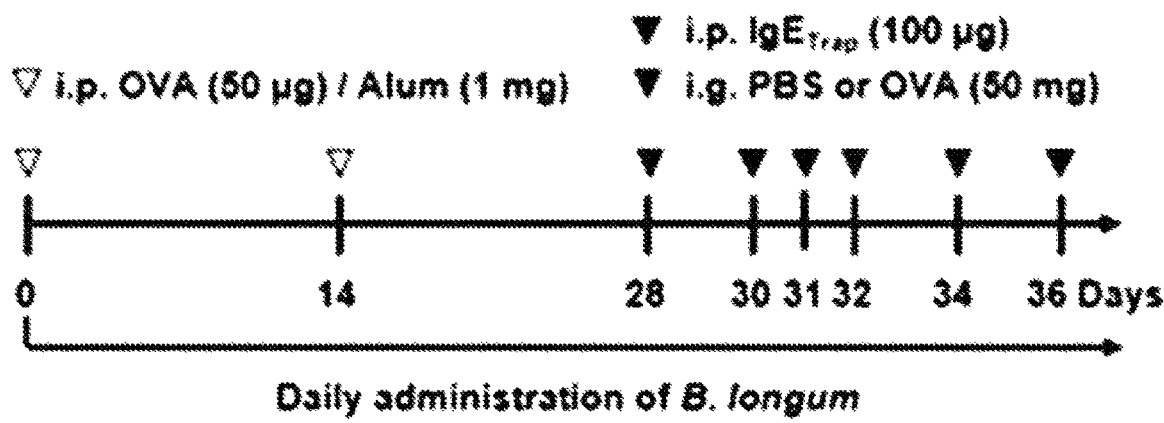
[FIG. 18]
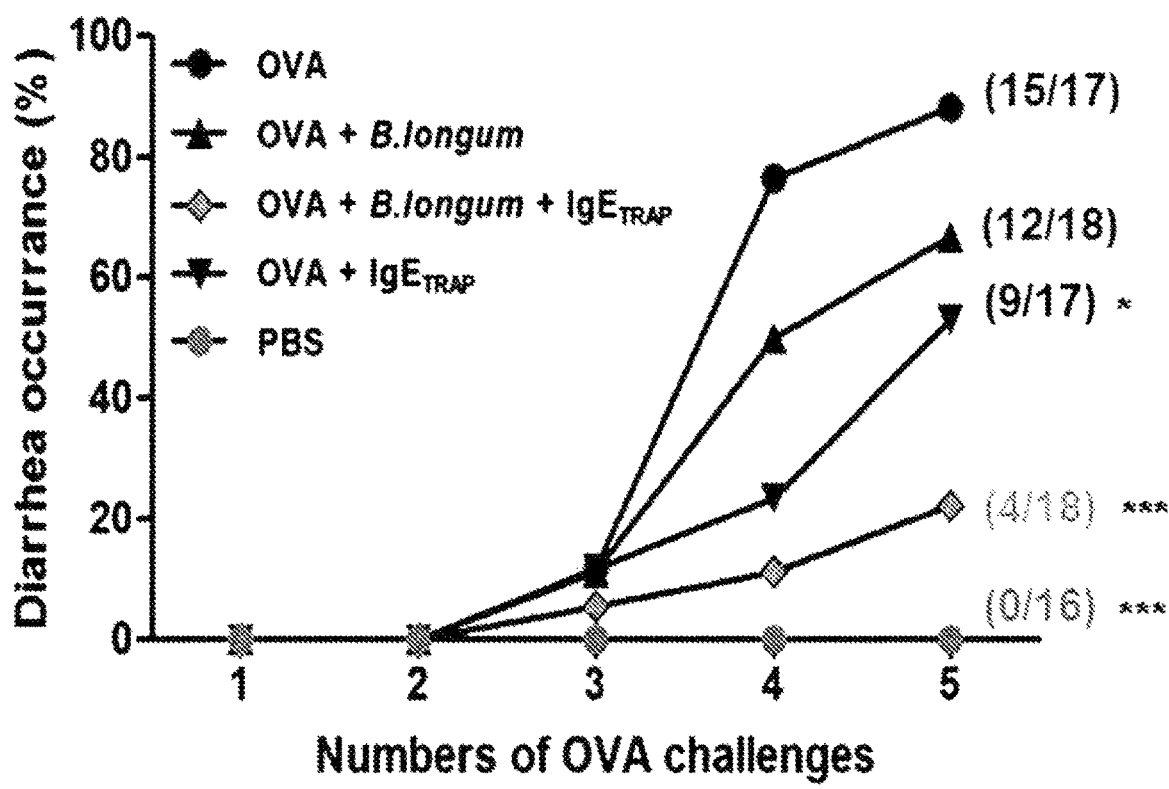

[FIG. 19A]
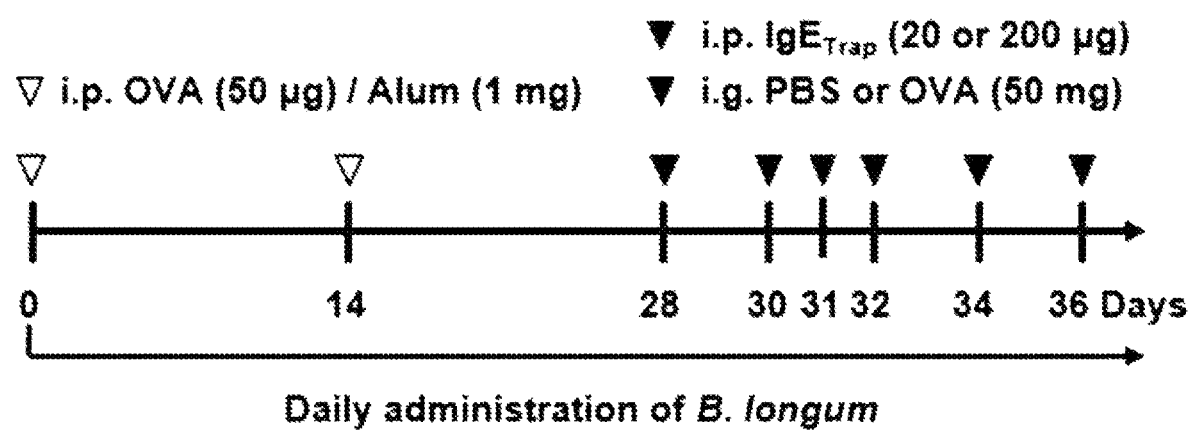

[FIG. 20]
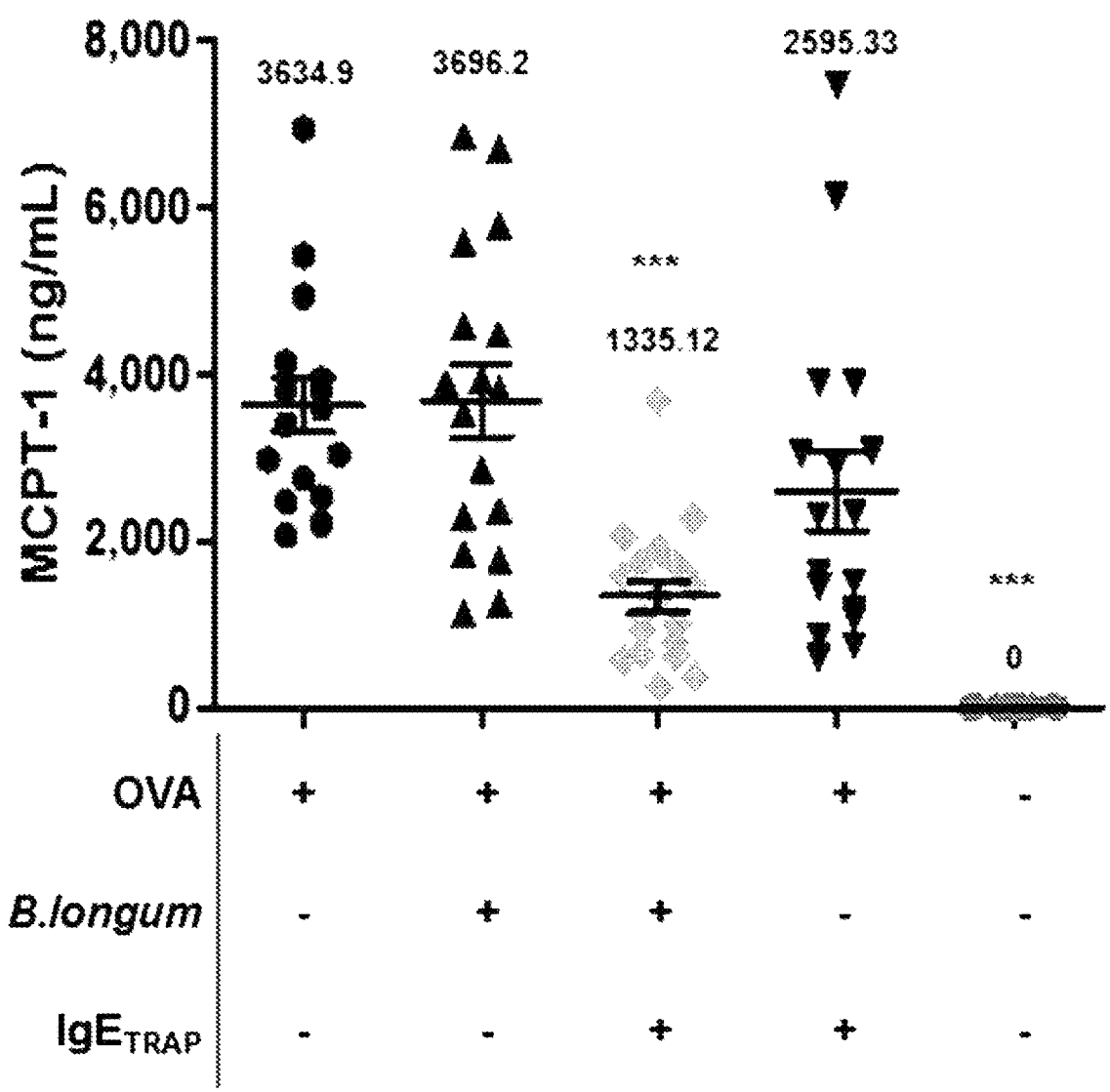

[FIG. 21]
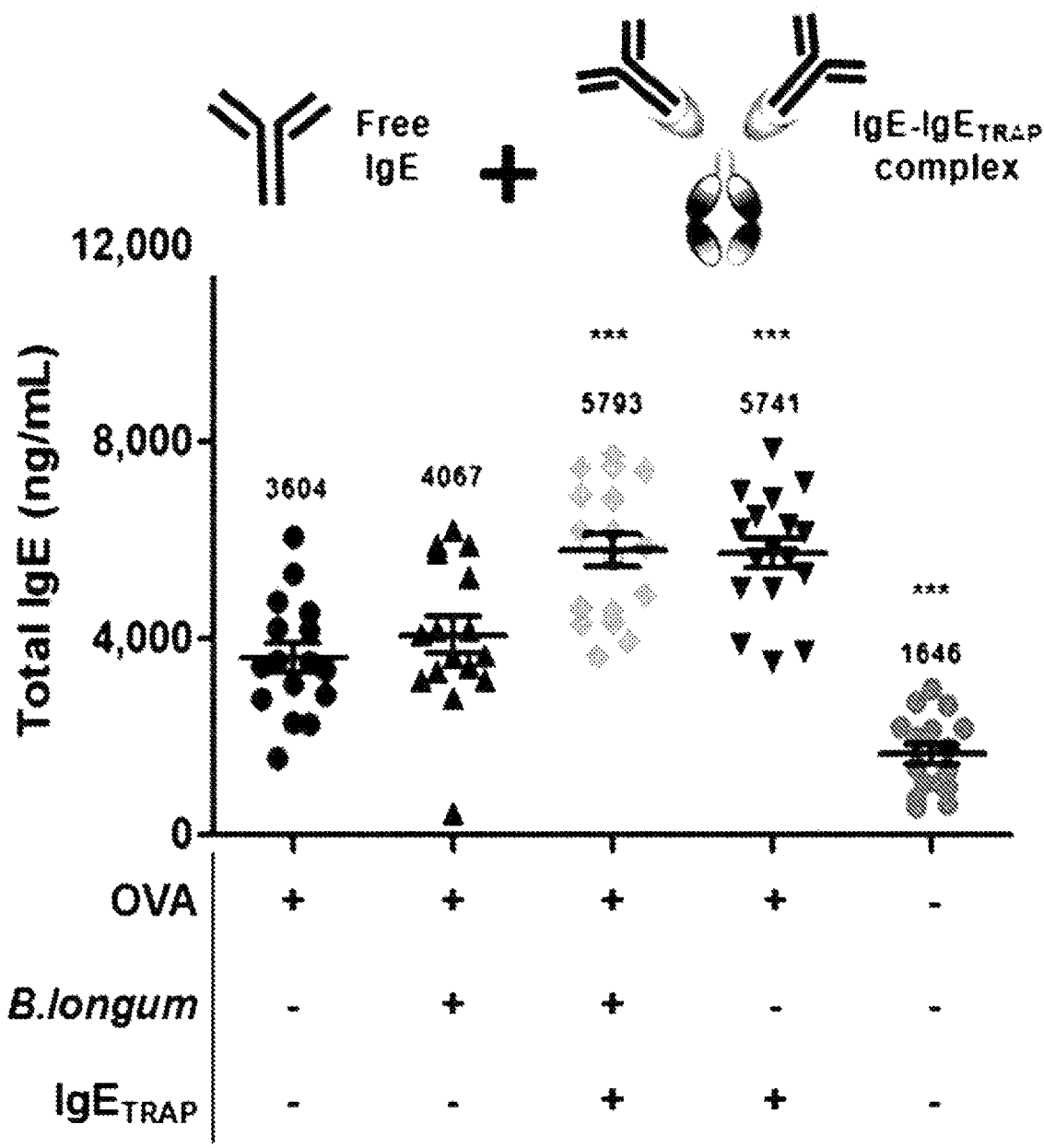

[FIG. 22]
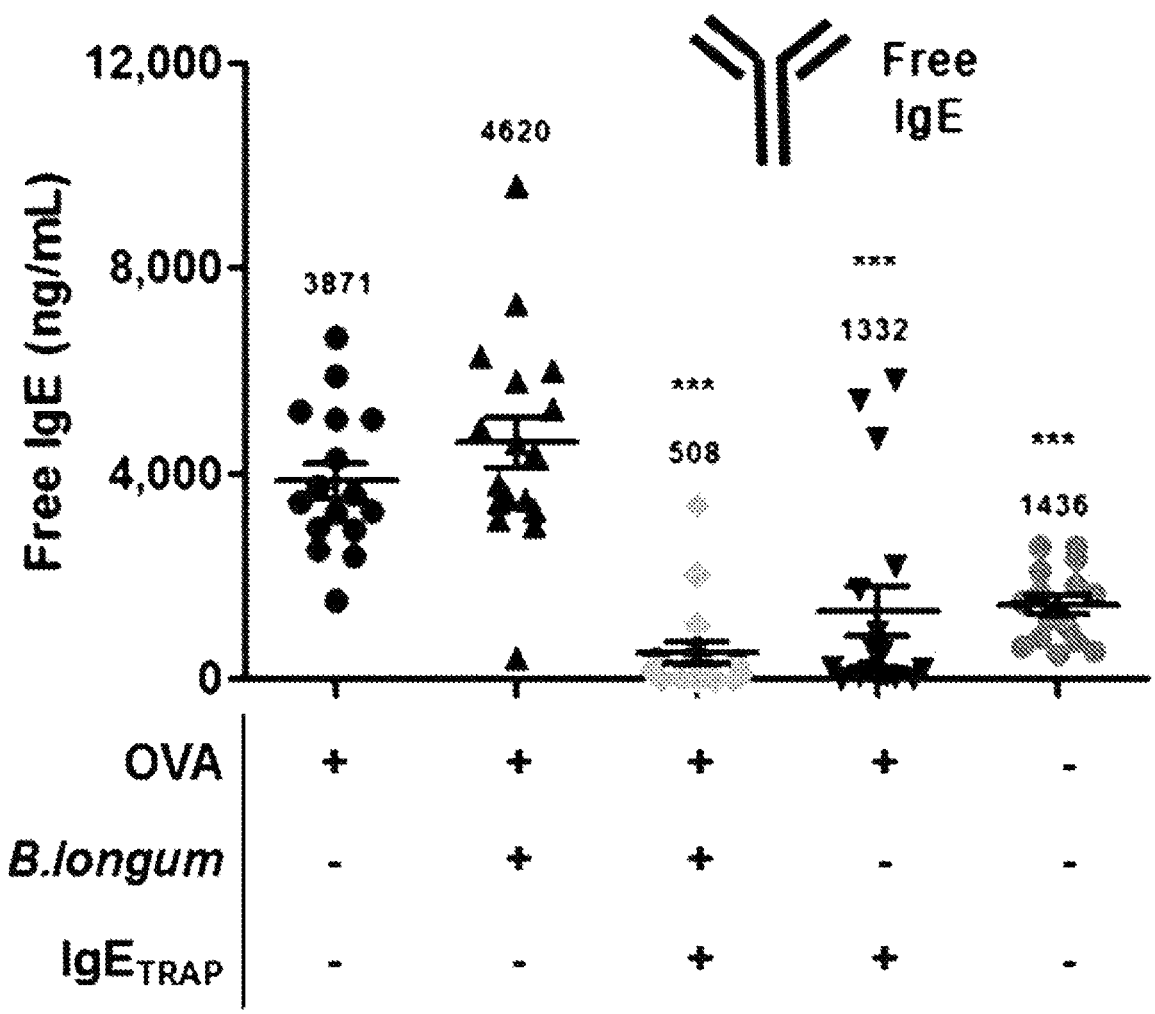

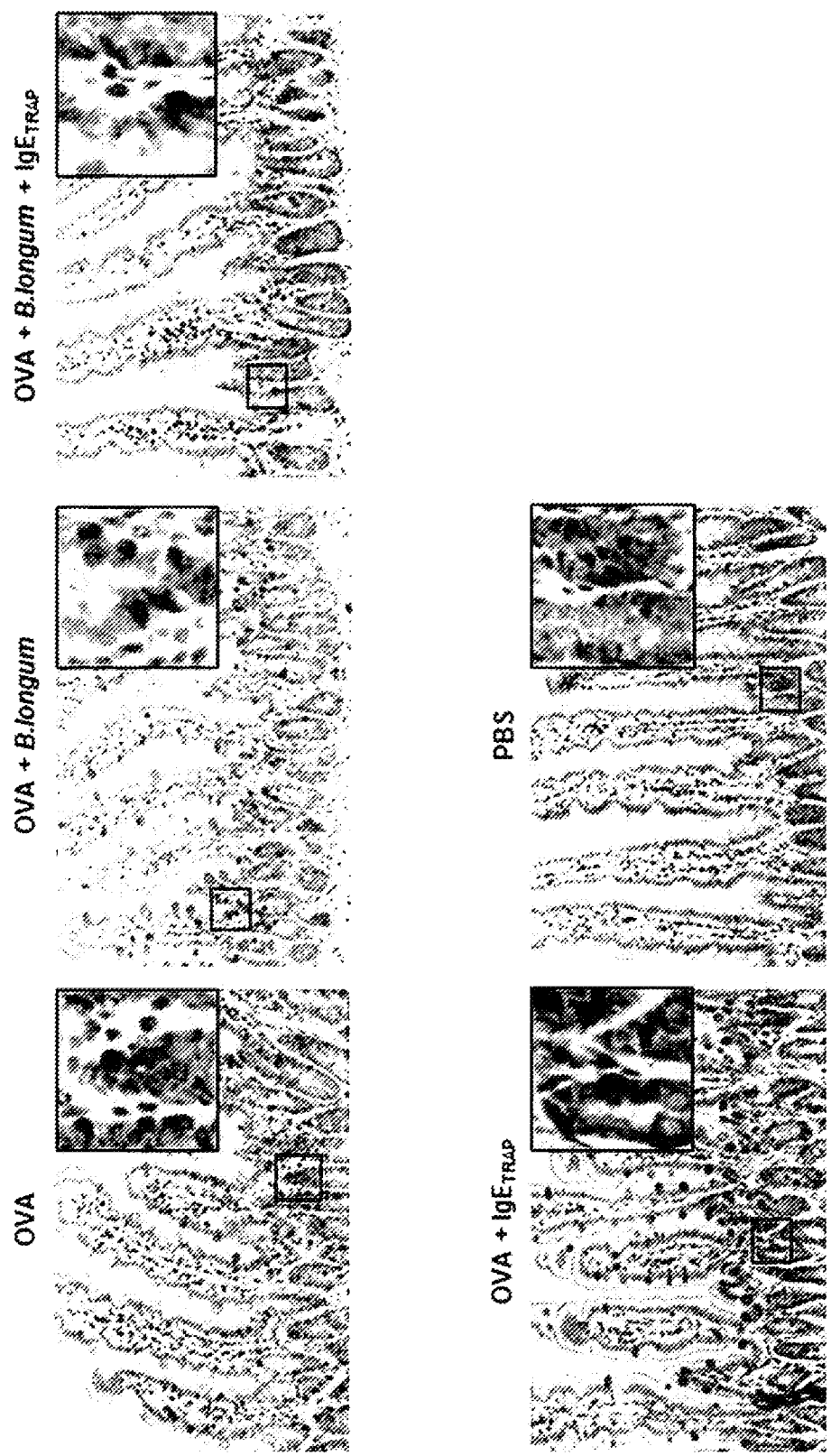
[FIG. 23]

[FIG. 24]
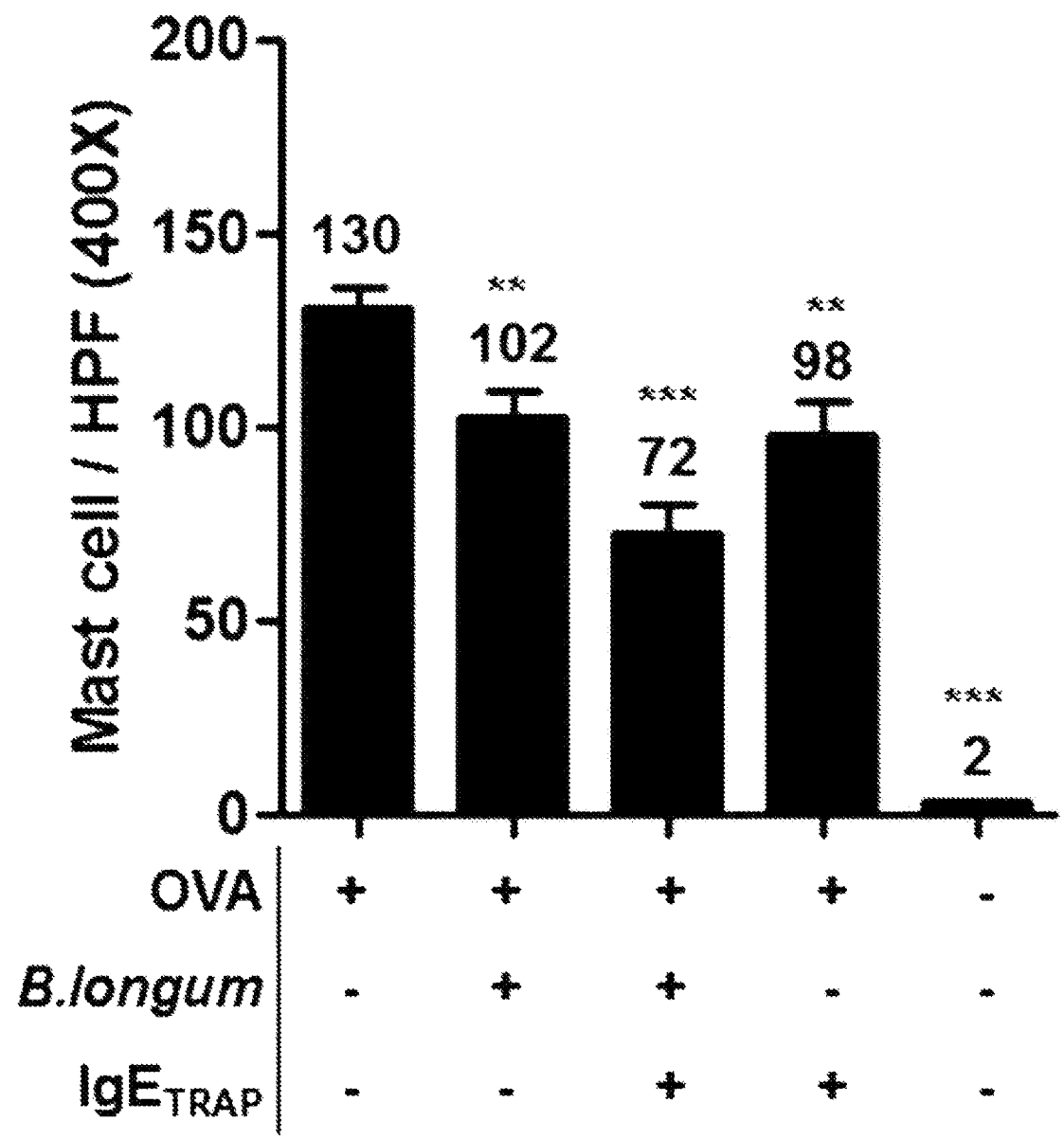

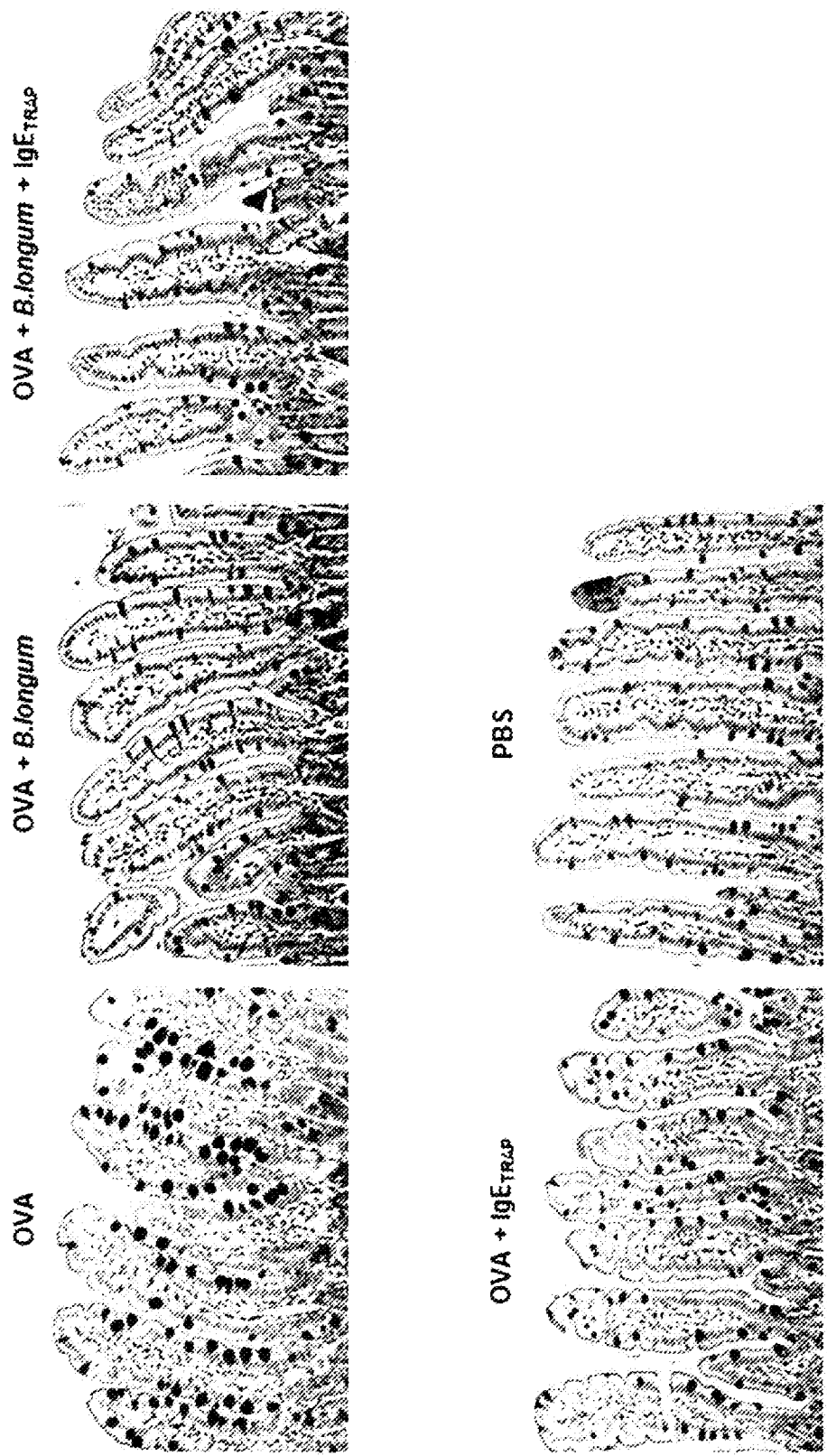
[FIG. 25]

[FIG. 26]
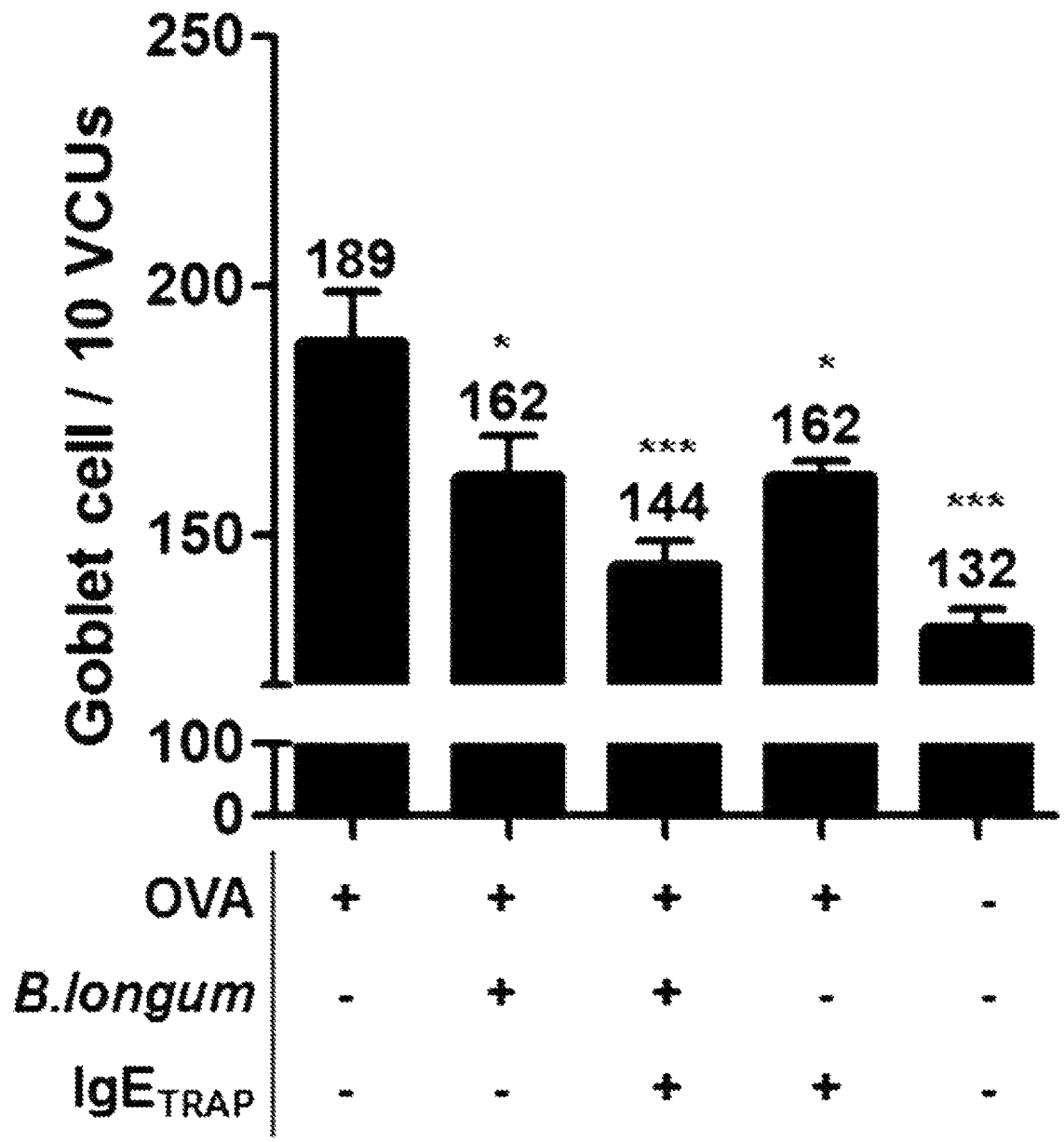

[FIG. 27]
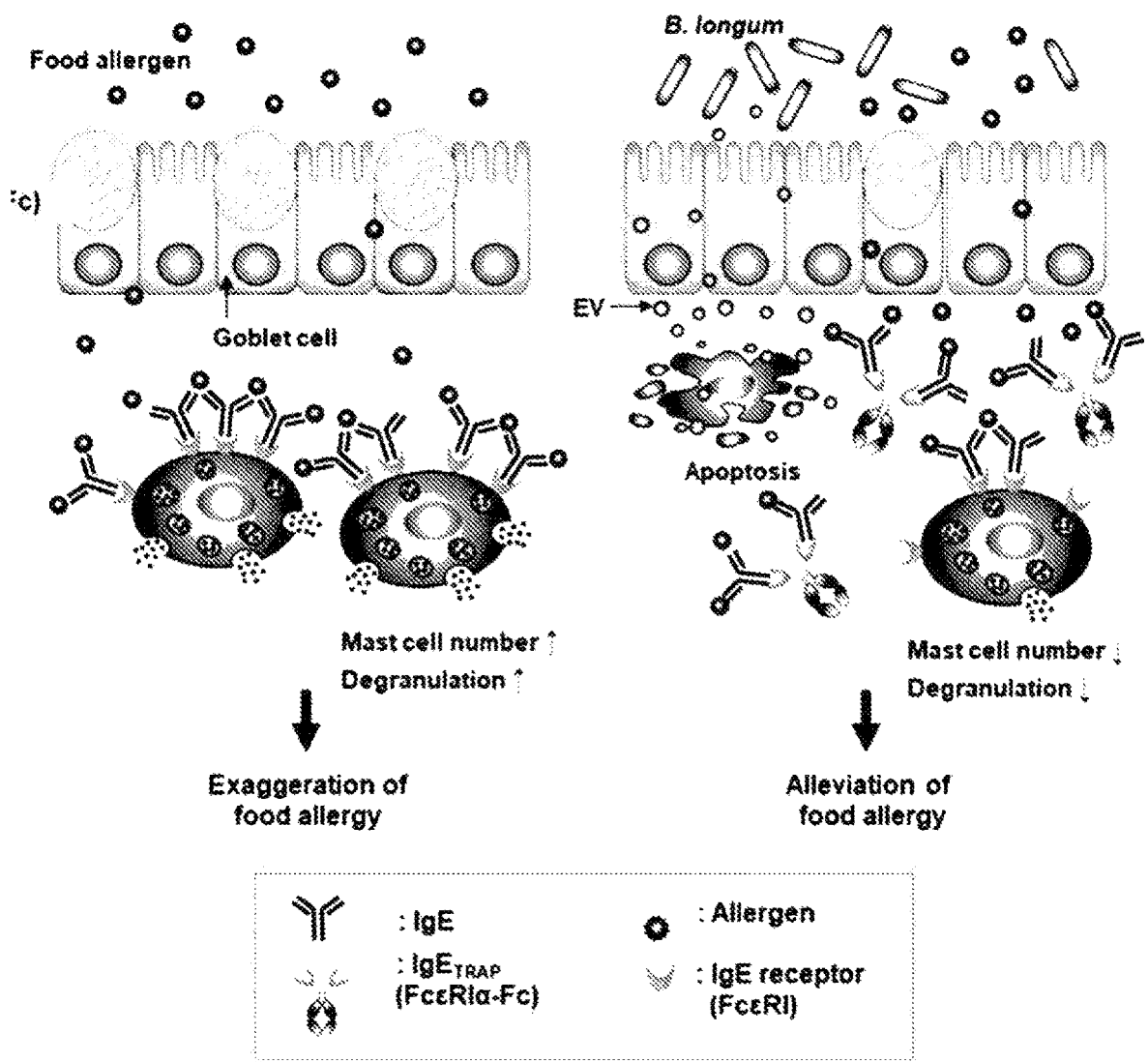

[FIG. 28]
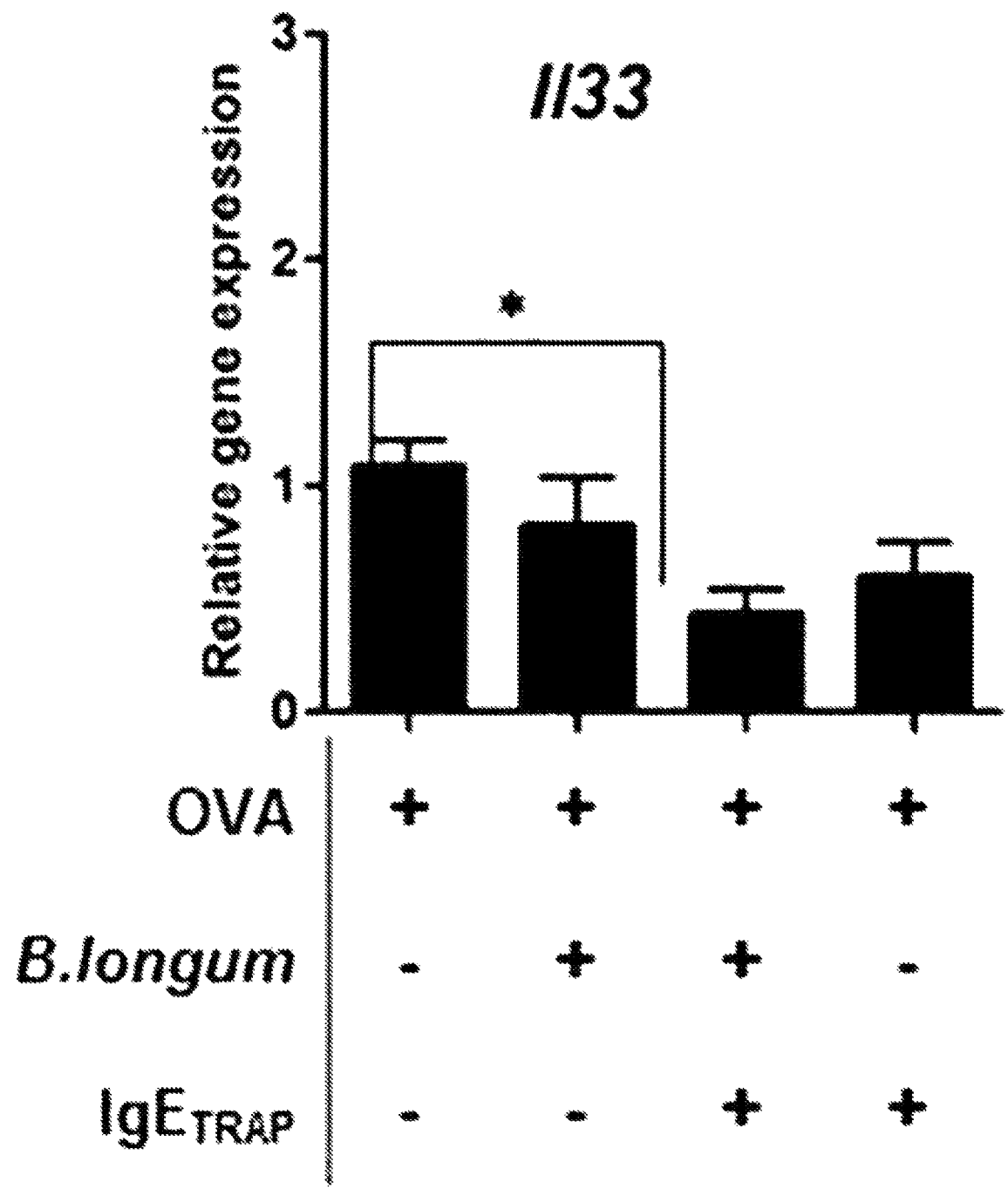

[FIG. 29]
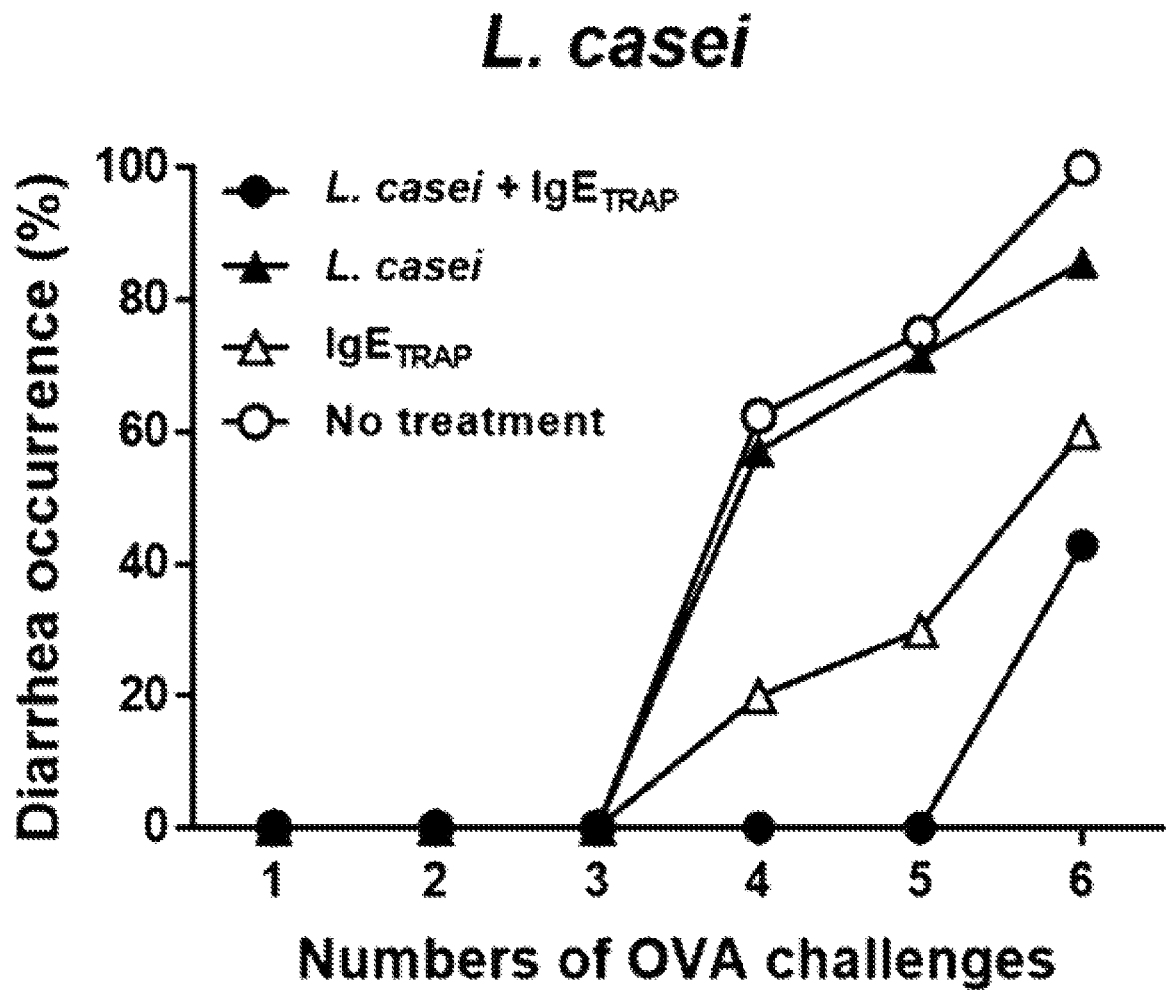

[FIG. 30]
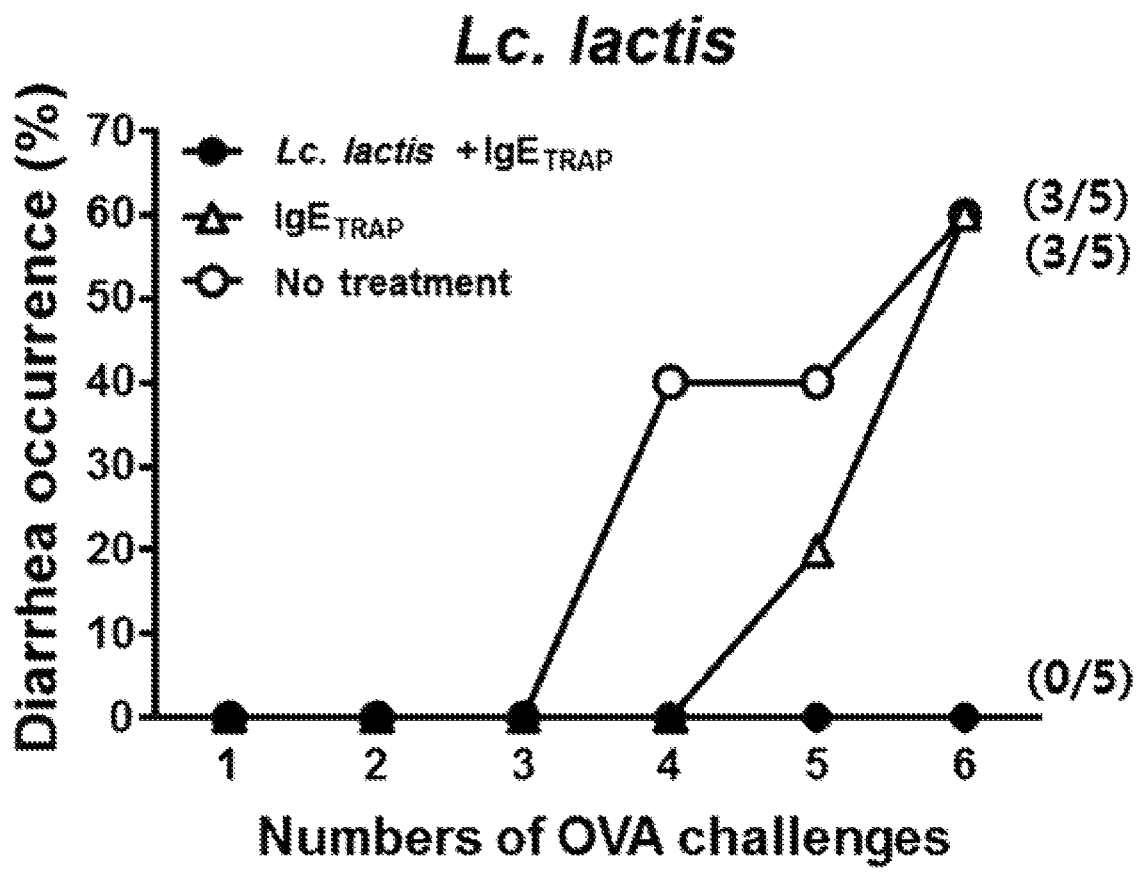

[FIG. 31]
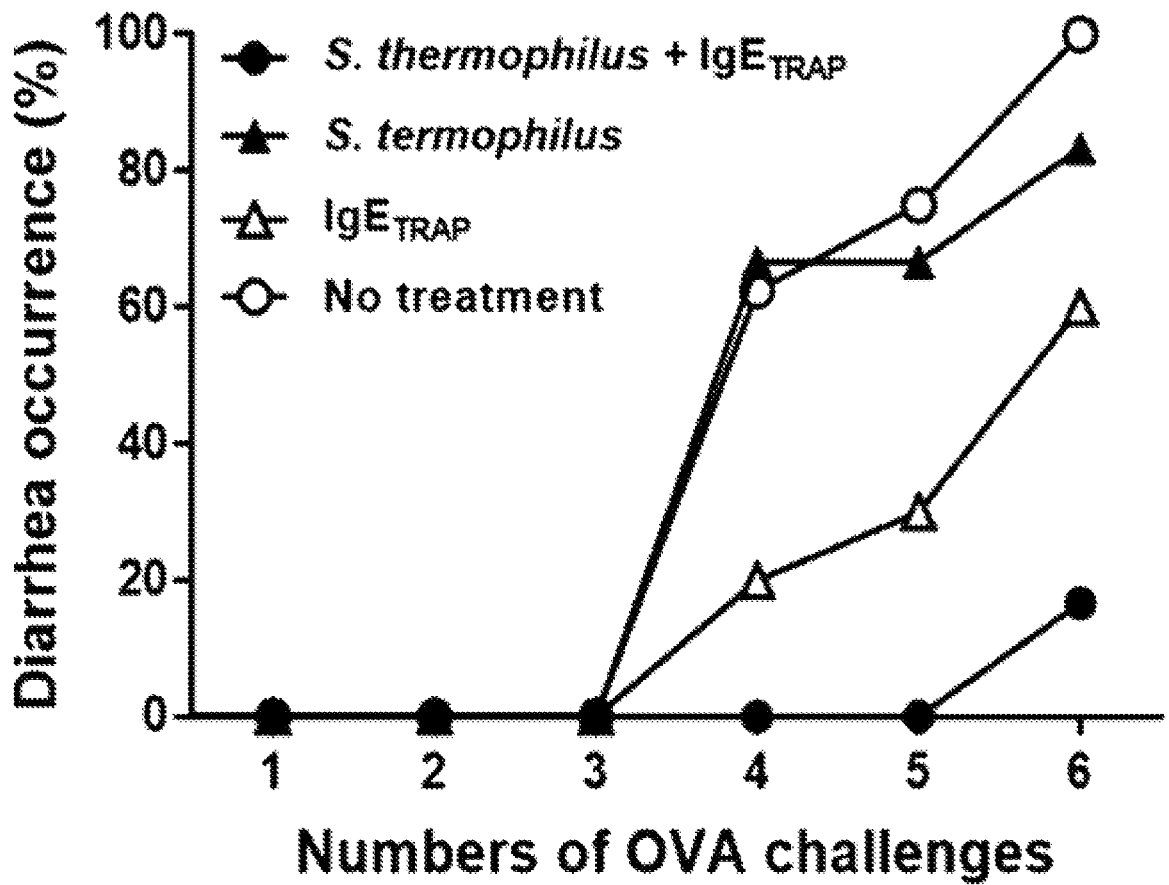

[FIG. 32]
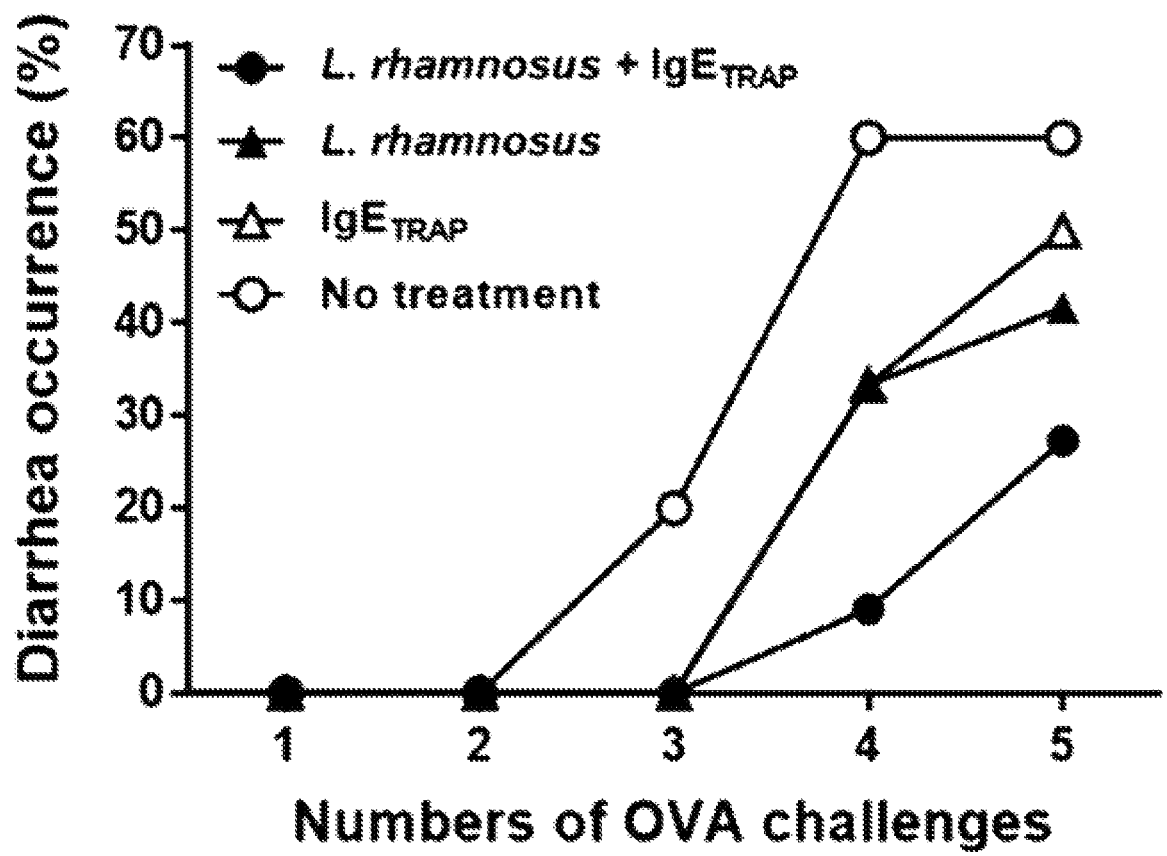

[FIG. 33]
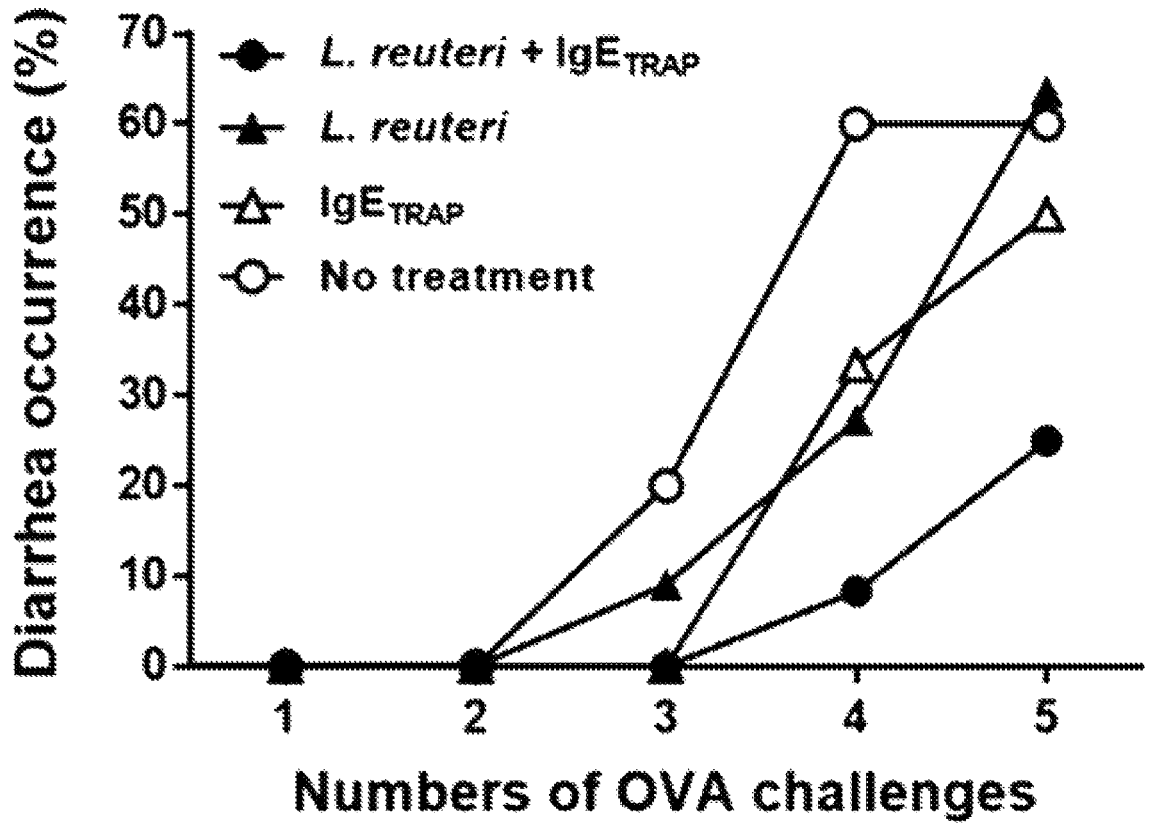

[FIG. 34]
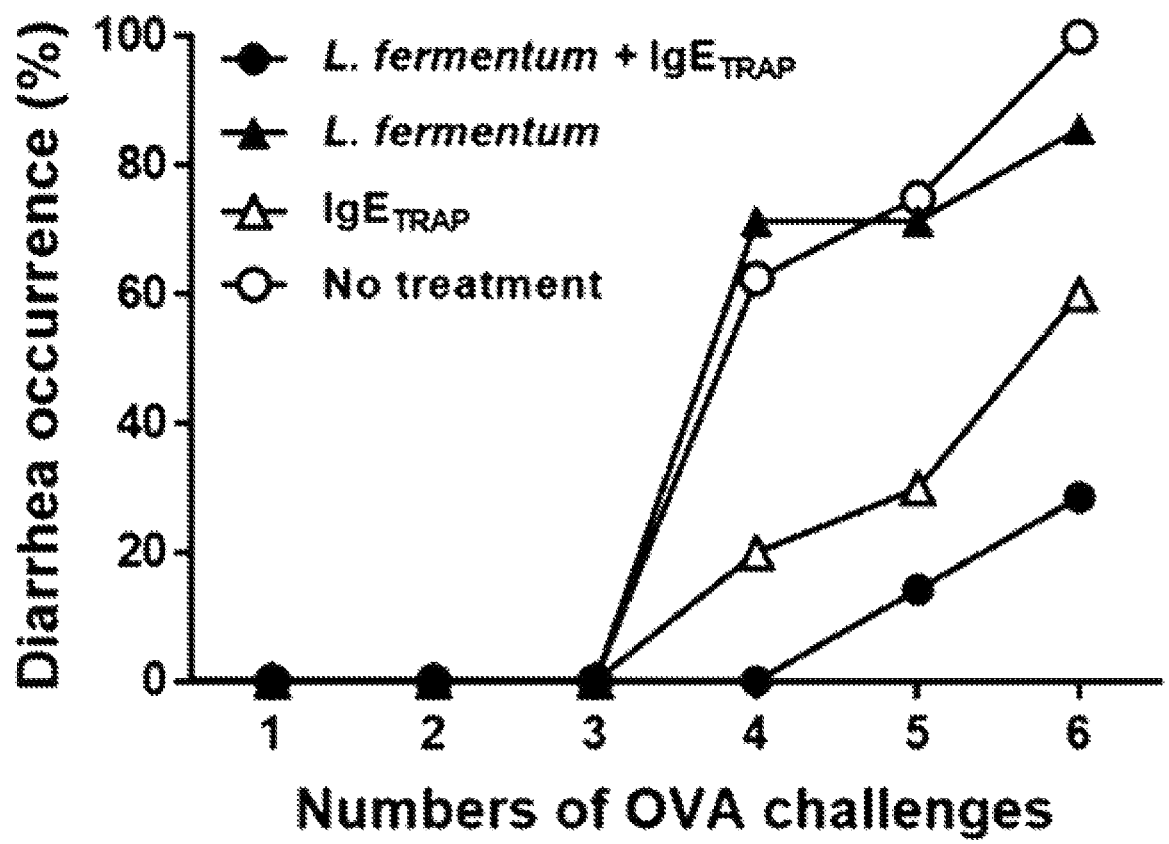

[FIG. 35]
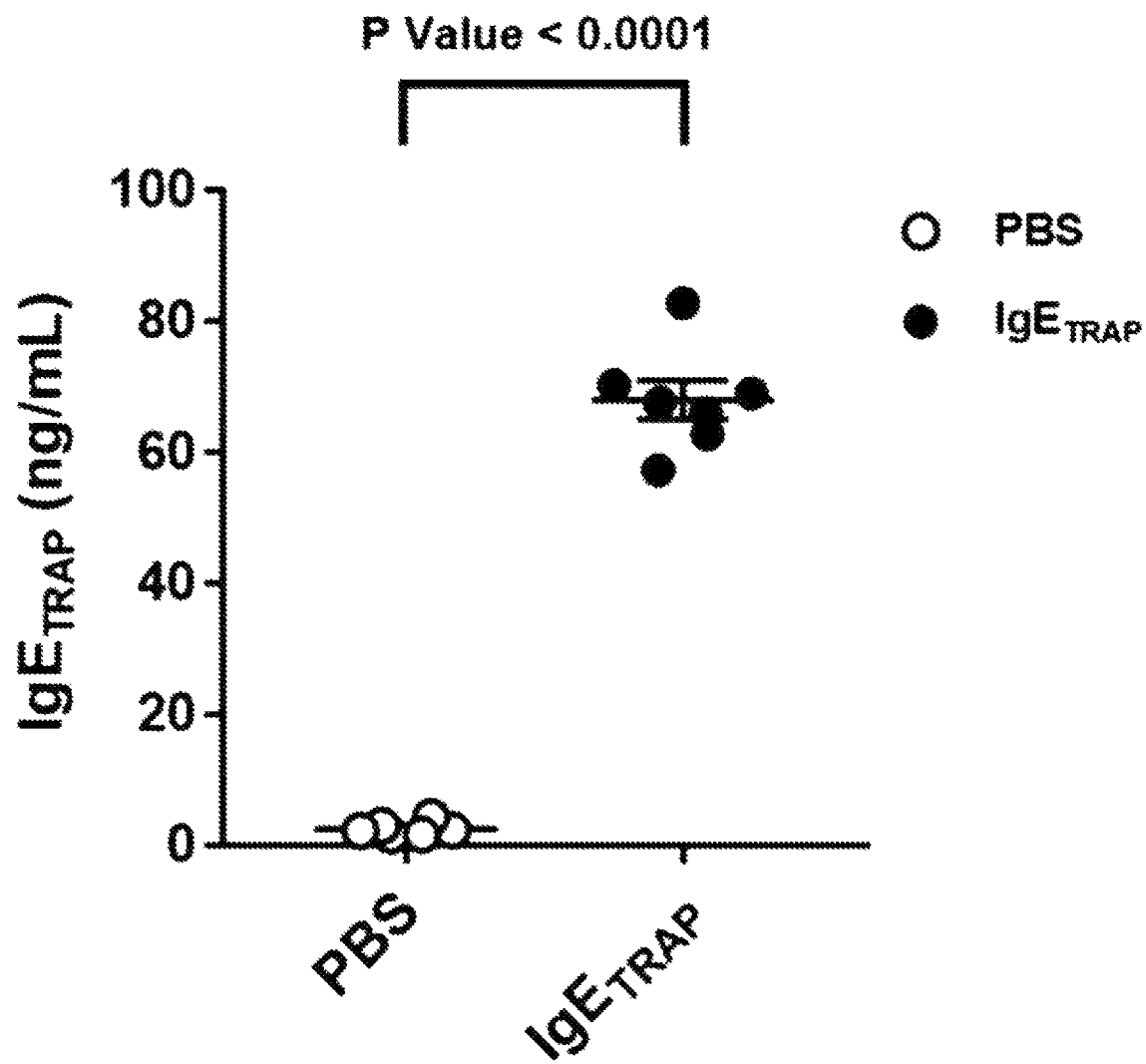

COMPOSITION COMPRISING PROBIOTICS AND POLYPEPTIDE HAVING BINDING AFFINITY FOR IGE AND USE THEREOF

CROSS REFERENCE TO RELATED APPLICATIONS

This application is a National Stage of International Application No. PCT/KR2019/000524 filed Jan. 14, 2019, claiming priority based on Korean Patent Application No. 10-2018-0004421 filed Jan. 12, 2018.

TECHNICAL FIELD

The present invention relates to a composition for treating or preventing an allergic disease.

BACKGROUND ART

Food allergy is a disease caused by decreased immunological resistance against non-pathogenic food antigens (allergens). The disease may lead to deteriorated quality of life due to dietary restrictions and may be life-threatening in a case where acute and chronic anaphylaxis develops. Allergic diseases such as allergic rhinitis and atopic dermatitis as well as such food allergy are spreading at a high rate in industrialized and westernized modern societies. In addition, development of anaphylaxis, a severe allergic reaction, is also increasing. These immune diseases severely impair quality of life and socioeconomic costs are soaring accordingly. Thus, there is a desperate need for measures to overcome such diseases.

Although food allergic diseases may develop through an IgE-mediated or non-IgE-mediated immune response, IgE-mediated food allergy is the most common. In the IgE-mediated food allergy, allergens bind to IgE, and allergen-bound IgE crosslinks FcεRI, a high-affinity IgE Fc receptor on effector cells such as mast cells and basophils, thereby inducing activation of the effector cells. In a case where the effector cells are activated, modulators are released, thereby causing immediate hypersensitivity. In addition to food allergic diseases, most allergic diseases are caused by an excessive immune response due to immunoglobulin E (IgE). IgE is an antibody that is normally present in serum at a very low concentration. IgE is also produced by innocuous antigens. In a case where the number of IgE is increased without any particular stimulus, an allergic disease may be caused. The abnormally increased number of IgE can bind to high-affinity IgE Fc receptors (FcεRIs) which are expressed on the surface of mast cells, basophils, and the like.

Such binding between IgE and the IgE Fc receptor causes mast cells or basophils to release chemical mediators such as histamine, leukotriene, prostaglandin, bradykinin, and platelet-activating factors. Release of these chemical mediators by the mast cells or basophils results in allergic symptoms. In particular, worsened allergic symptoms may be exhibited in a case where IgE and FcεRI are bound to each other. FcεRI-expressing cells are known to increase in allergic patients.

Various methods, such as allergen avoidance, administration of anti-allergic drugs, modulation of IgE synthesis in the body, and development of anti-IgE antibodies, have been proposed to treat allergic diseases. However, such methods have many drawbacks, such as inability to cure an underlying cause of allergy, insufficient drug efficacy, and occurrence of serious side effects.

Meanwhile, a method of using microorganisms such as lactic acid bacteria has been studied for the purpose of treating or ameliorating allergic diseases. Such healthy microorganisms are called probiotics. However, techniques to discover and evaluate probiotics for immune control such as allergy inhibition have not yet been established. In particular, studies on the underlying action mechanism of probiotics are inadequate, and most of the studies are conducted in vitro. In other words, although probiotics are orally ingested, most of the studies so far have focused on in vitro experiments using cell lines, and these experimental methods have a major drawback that it is not possible to provide a substitute for studies on functions that may be exhibited in a case where a human ingests probiotics.

In addition, immunoglobulin compositions have been studied to treat allergic diseases. Such compositions have been reported to be useful for treating IgE-mediated disorders including allergy and asthma (KR10-1783272B1). In particular, XOLAIR™ (omalizumab), which targets an Fc portion of an IgE antibody, has been developed and used as a therapeutic agent for intractable severe asthma and intractable urticaria. However, a high-dose administration of omalizumab is required in order to maintain effects. Thus, it has been reported that omalizumab has a high cost burden, and side effects such as angioedema and anaphylactic reaction (*The Journal of Clinical Investigation*, Volume 99, Number 5, March 1997, 915-925).

Although the underlying mechanism by which omalizumab causes side effects has not yet been identified, it can be expected that omalizumab is an IgG1 antibody. A study which targets a mouse model showed that a large number of antigen-specific IgG1 antibodies can induce passive systemic anaphylaxis (PSA) through FcγRIII, a low-affinity IgG receptor, and platelet-activating factors in an antigen-rich environment. In addition, such IgG-mediated anaphylaxis occurs exaggeratedly due to lack of FcεRI signaling. Therefore, passive systemic anaphylaxis may be caused in a case where a considerable amount of omalizumab is injected into a patient with an allergic disease who exhibits a high level of IgE. Recently, it has been reported that FcγRIIA, a low-affinity IgG receptor expressed in a human, is also associated with IgG-mediated anaphylaxis. In addition, post-marketing studies have reported abnormal reactions such as allergic granulomatous vasculitis and idiopathic severe thrombocytopenia.

Technical Problem

Although many studies have been conducted on allergic diseases, a method for dramatically ameliorating allergic diseases has not been developed so far. An object of the present invention is to provide a composition for treating or preventing such allergic diseases.

Solution to Problem

According to an aspect of the present invention, there is provided a composition comprising, as active ingredients, probiotics and a polypeptide with a binding ability to IgE.

In another aspect, there is provided a pharmaceutical composition for treating or preventing an allergic disease, comprising the composition as an active ingredient. In yet another aspect, there is provided a health functional food composition for ameliorating or alleviating an allergic symptom, comprising the composition as an active ingredient.

In still yet another aspect, there is provided a kit for treating or preventing an allergic disease, comprising a first composition that contains probiotics and a second composition that contains a polypeptide with a binding ability to IgE.

Advantageous Effects of Invention

The composition comprising, as active ingredients, probiotics and a polypeptide with a binding ability to IgE, according to the present invention, exhibits an excellent effect of ameliorating allergy in vivo. Thus, the composition can be used as a pharmaceutical composition for treating or preventing a severe allergic disease. Furthermore, from the viewpoint that the composition of the present invention can be applied to oral immunotherapy, the composition may not only be more effective for food allergy while decreasing side effects, but also ideal for treating children suffering from IgE-mediated allergies. Therefore, the composition can be used as a health functional food for ameliorating or alleviating an allergic symptom.

BRIEF DESCRIPTION OF DRAWINGS

FIG. 1 illustrates a schematic diagram of the constitution of a monomer forming an embodiment ($IgE_{TRAP}$) of the polypeptide dimer of the present invention. An embodiment of $IgE_{TRAP}$ can consist of 425 amino acids from human FcεRIα (region from $26^{th}$ amino acid to $205^{th}$ amino acid in FcεRIα extracellular domain, 180 aa) to human IgD/IgG4 hybrid Fc (245 amino acids). The IgD/IgG4 hybrid Fc has an FcRn-binding site (right hatched line) but lacks binding sites for FcγR and C1q (left hatched line). Here, IgD may be a region (38 aa) from $133^{rd}$ amino acid to $170^{th}$ amino acid, and IgG4 may be a region (207 aa) from $121^{st}$ amino acid to $327^{th}$ amino acid.

FIG. 2 illustrates a three-dimensional structural model of an $IgE_{TRAP}$ homodimer. The structure shows an FcεRIα extracellular domain (blue), an IgD hinge (yellow), and an IgG4 Fc (green).

FIGS. 3A-3B illustrate SDS-PAGE results for polypeptides with a binding ability to IgE produced in each cell line (FIG. 3A). Here, it can be seen that a truncated form is not generated at both reducing and non-reducing conditions (FIGS. 3A and 3B).

FIG. 4 illustrates results of isoelectric focusing (GEL-IEF) experiments performed to identify an increase in sialic acid content of polypeptides with a binding ability to IgE which have been produced in each cell line. A content of proteins with lowered major isoelectric point (pI) is increased due to an increase in content of negatively charged sialic acid caused by introduction of a sialic acid transferase gene. From this, it can be seen that a content of acidic proteins is increased through addition of sialic acid transferase.

FIG. 5 illustrates SDS-PAGE results for non-reduced and reduced forms of a polypeptide dimeric protein ($IgE_{TRAP}$) according to an embodiment of the present invention. In particular, it can be seen that the polypeptide dimer has high purity even in culture supernatant which corresponds to Input.

FIG. 6 illustrates results obtained by performing SDS-PAGE analysis of $IgE_{TRAP}$ under non-reduced and reduced conditions.

FIG. 7 illustrates a graph showing a binding ability of omalizumab to IgE. The graph shows results obtained by immobilizing omalizumab and analyzing a binding ability thereof depending on IgE concentrations treated. Interaction between human IgE and omalizumab was analyzed using surface plasmon resonance (SPR), and a binding affinity of each molecule was calculated.

FIG. 8 illustrates a graph showing a binding ability, to IgE, of the polypeptide dimeric protein ($IgE_{TRAP}$) according to an embodiment of the present invention. The graph shows results obtained by immobilizing the $IgE_{TRAP}$ and analyzing a binding ability thereof depending on IgE concentrations treated. Interaction between human IgE and the $IgE_{TRAP}$ was analyzed using surface plasmon resonance (SPR), and a binding affinity of each molecule was calculated.

FIGS. 9 to 13 illustrate results obtained by identifying interactions of the dimeric protein ($IgE_{TRAP}$), an embodiment of the present invention, and omalizumab with IgG receptors FcγRI (FIG. 9), FcγRIIA (FIG. 10), FcγRIIB (FIG. 11), FcγRIIIA (FIG. 12), and FcγRIIIB (FIG. 13) using bio-layer interferometry (BLI) assay.

FIG. 15B illustrates a graph showing a comparison between inhibitory abilities, on activity of human FcεRI-expressing mouse-derived mast cells, of the polypeptide dimeric protein ($IgE_{TRAP}$) according to an embodiment of the present invention and XOLAIR™ (omalizumab) depending on concentrations thereof.

FIG. 17 illustrates an experimental schedule for food allergy induction, and $IgE_{TRAP}$, *B. longum*, and combination therapy. i.p., intraperitoneal; i.g., intragastric FIG. 18 illustrates potencies of $IgE_{TPAP}$, *B. longum*, and combination therapy to inhibit allergy-induced diarrhea symptoms. n=16 to 18 mice per group, OVA vs OVA+$IgE_{TRAP}$: *P<0.05, OVA vs OVA+*B. longum*+$IgE_{TRAP}$, and OVA vs PBS: ***P<0.0001

FIG. 19A illustrates an experimental plan to identify that *B. longum* improves therapeutic effects of $IgE_{TRAP}$. Specifically, an experimental plan for food allergy induction, and single or combined administration of $IgE_{TRAP}$ and *B. longum* is shown. i.p., intraperitoneal; i.g., intragastric

FIG. 20 illustrates results obtained by analyzing, with ELISA, mast cell protease-1 (MCPT-1) levels in sera obtained from respective experimental groups, at the time of administration of $IgE_{TRAP}$, *B. longum*, and a combination thereof, in a food allergy-induced disease model.

FIG. 21 illustrates results obtained by measuring, with ELISA, total IgE (free IgE and IgE-$IgE_{TRAP}$ complex) levels in sera obtained from respective experimental groups, at the time of administration of $IgE_{TRAP}$, *B. longum*, and a combination thereof, in a food allergy-induced disease model.

Figure 14:
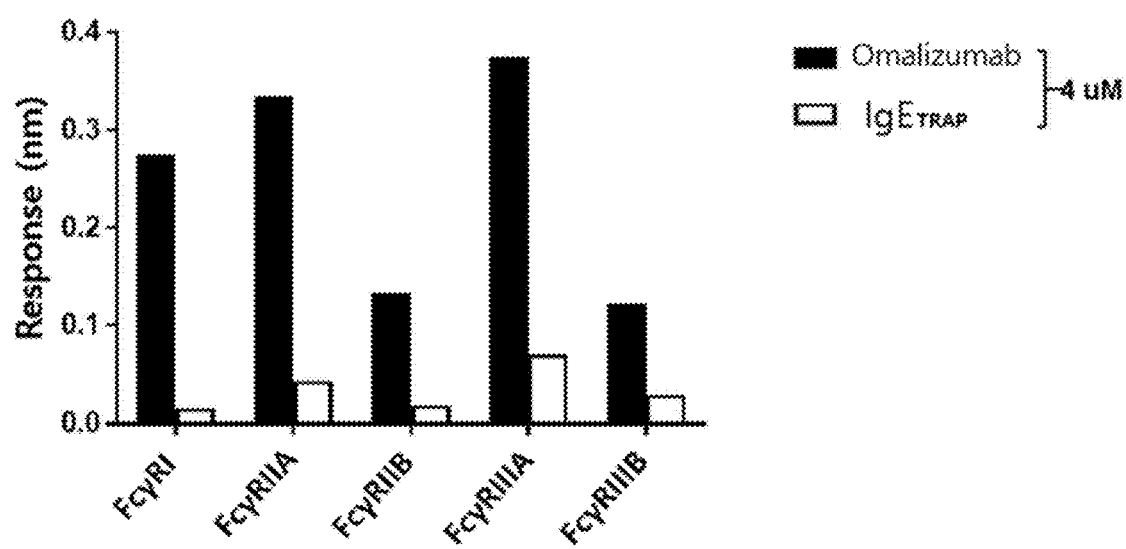
FIG. 14 illustrates a graph obtained by quantifying a binding capacity between $IgE_{TRAP}$ and IgG receptors, and between omalizumab and IgG receptors.

n=16 to 18 mice per group, OVA vs OVA+IgE$_{TRAP}$, OVA vs OVA+B. longum+IgE$_{TRAP}$, and OVA vs PBS: ***P<0.0001

FIG. 22 illustrates results obtained by measuring, with ELISA, free IgE levels in sera obtained from respective experimental groups, at the time of administration of IgE$_{TRAP}$, B. longum, and a combination thereof, in a food allergy-induced disease model. n=16 to 18 mice per group, OVA vs OVA+IgE$_{TRAP}$, OVA vs OVA+B. longum+IgE$_{TRAP}$, and OVA vs PBS: ***P<0.0001

FIG. 23 illustrates results obtained by identifying inhibitory effects on mast cell proliferation and goblet cell proliferation in respective experimental groups, at the time of administration of IgE$_{TRAP}$, B. longum, and a combination thereof, in a food allergy-induced disease model. Results obtained by staining mast cells (red) in representative paraffin sections of the jejunum in the respective experimental groups are shown (magnification 400×). Enlargement of the jejunum clearly shows the mast cells (red).

FIG. 24 illustrates results obtained by enlarging the mast cells 400 times in FIG. 23 and identifying the mast cells. n=10 to 12 mice per group, OVA vs B. longum, and OVA vs IgE$_{TRAP}$: P<0.001, OVA vs OVA+B. longum+IgE$_{TRAP}$, and OVA vs PBS: *P<0.0001

FIG. 25 illustrates results obtained by identifying inhibitory effects on mast cell proliferation and goblet cell proliferation in respective experimental groups, at the time of administration of IgE$_{TRAP}$, B. longum, and a combination thereof, in a food allergy-induced disease model. Results obtained by staining goblet cells for identification in representative paraffin sections of the jejunum in the respective experimental groups are shown (purple, magnification 400×).

FIG. 26 illustrates results obtained by randomly selecting globet cells from villus-crypt units (VCUs) in FIG. 25 and counting 10 VCUs. n=5 to 6 mice per group, OVA vs B. longum, and OVA vs IgE$_{TRAP}$: *P<0.05, OVA vs OVA+B. longum+IgE$_{TRAP}$, and OVA vs PBS: ***P<0.0001

FIG. 27 illustrates a schematic diagram of mechanism of food allergy inhibition caused by combined therapy with B. longum and IgE$_{TRAP}$. Food allergens ingested can induce activation of effector cells (mast cells and basophils) by binding of IgE to a high-affinity IgE Fc receptor (FcεRI) on the effector cells. Activated effector cells release modulators, thereby causing an immediate hypersensitivity reaction. B. longum induces apoptosis of mast cells through secretion of extracellular vesicle (EV) which decreases the number of mast cells. In the meantime, IgE$_{TRAP}$ can block IgE binding to FcεRI on effector cells, and thus inhibit activation and proliferation of the effector cells. Combined administration of B. longum and IgE$_{TRAP}$ made it possible to effectively alleviate food allergic symptoms and goblet cell hyperplasia.

FIG. 28 illustrates a graph obtained by identifying changes in IL-33 expression in intestinal tissue after administration of B. longum and IgE$_{TRAP}$. Administration of B. longum and IgE$_{TRAP}$ decreased expression of IL-33 mRNA in the jejunum of food allergy model mice. n=16 to 18 mice per group, OVA vs OVA+B. longum+IgE$_{TRAP}$: *P<0.05

FIG. 29 illustrates a graph obtained by identifying diarrhea frequency after intraperitoneal injection of IgE$_{TRAP}$ and L. casei. n=7 to 10 mice per group FIG. 30 illustrates a graph obtained by identifying diarrhea frequency after intraperitoneal injection of IgE$_{TRAP}$ and Lc. lactis. n=5 mice per group FIG. 31 illustrates a graph obtained by identifying diarrhea frequency after intraperitoneal injection of IgE$_{TRAP}$ and S. thermophilus. n=6 to 10 mice per group FIG. 32 illustrates a graph obtained by identifying diarrhea frequency after intraperitoneal injection of IgE$_{TRAP}$ and L. rhamnosus. n=5 to 10 mice per group FIG. 33 illustrates a graph obtained by identifying diarrhea frequency after intraperitoneal injection of IgE$_{TRAP}$ and L. reuteri. n=5 to 10 mice per group FIG. 34 illustrates a graph obtained by identifying diarrhea frequency after intraperitoneal injection of IgE$_{TRAP}$ and L. fermentum. n=7 to 10 mice per group FIG. 35 illustrates a graph obtained by orally administering IgE$_{TRAP}$ to normal mice and then identifying IgE$_{TRAP}$ adsorbed in serum of the mice.

DETAILED DESCRIPTION OF INVENTION

In an aspect of the present invention, there is provided a composition comprising, as active ingredients, probiotics and a polypeptide with a binding ability to IgE.

As used herein, the term "probiotics" collectively refers to microorganisms that are favorable to the human body in a case of being ingested in an appropriate amount, indicating bacteria beneficial to the human body. The probiotics may be lactic acid bacteria or Bifidobacterium. The lactic acid bacteria collectively refer to bacteria that ferment sugar to produce lactic acid. Most intestinal beneficial bacteria are classified as lactic acid bacteria, and the lactic acid bacteria can degrade sugars, of which 50% or more thereof is produced as lactic acid.

The lactic acid bacteria may be any one selected from the group consisting of Lactobacillus, Lactococcus, Enterococcus, and Streptococcus. Specifically, the Lactobacillus may be any one selected from the group consisting of L. acidophilus, L. casei, L. gasseri, L. delbrueckii ssp. bulgaricus, L. helveticus, L. fermentum, L. paracasei, L. plantarum, L. reuteri, L. rhamnosus, L. pentosus, and L. salivarius. In addition, the Lactococcus may be Lc. lactis, and the Streptococcus may be S. thermophilus. In addition, the Bifidobacterium may be any one selected from the group consisting of B. bifidum, B. breve, B. longum, and B. animalis ssp. lactis.

Preferably, the probiotics may be Lactobacillus casei or Bifidobacterium longum. In particular, Bifidobacterium longum may be accession no. KACC 91563 (KR10-1778734B1). In particular, the KACC 91563 strain targets mast cells which are important cells in allergic reactions, and thus can be utilized as lactic acid bacteria that treat allergy. Usually, the probiotics can be used in the form of live bacteria, in which the live bacteria can be used in a lyophilized form. In addition, the probiotics may be used in the form of dead bacteria.

As used herein, the term "polypeptide with a binding ability to IgE" means a polypeptide capable of binding to IgE. As used herein, the term "IgE" means an antibody protein known as immunoglobulin E. IgE has an affinity to mast cells, blood basophils, or the like. In addition, reaction between an IgE antibody and an antigen (allergen) corresponding thereto causes an inflammatory reaction. In addition, IgE is known to be an antibody that causes anaphylaxis.

Specifically, the polypeptide with a binding ability to IgE may be any one of recombinant proteins including an anti-IgE antibody, an IgE Fc receptor, an extracellular domain of an alpha subunit of the IgE Fc receptor, a fragment of the extracellular domain fragment of the alpha subunit of the IgE Fc receptor, and an extracellular domain of an alpha subunit of the IgE Fc receptor or a fragment thereof.

Here, the anti-IgE antibody means an antibody capable of recognizing IgE as an antigen and binding IgE. Here, a fragment of the anti-IgE antibody may be any one selected from the group consisting of Fab, scFv, F(ab)², and Fv, as long as the fragment can bind to IgE. Antibody fragments mean antigen binding domains excluding a crystallizable region (Fc region) that performs a function (effector function) to transfer, to a cell or a complement, stimulus due to binding with an antigen. An embodiment of the anti-IgE antibody may be omalizumab.

As used herein, the term "IgE Fc receptor" is also referred to as Fcεreceptor and binds to an Fc portion of IgE. There are two types for the receptor. The receptor having high affinity to IgE Fc is called Fcεreceptor I (FcεRI). The receptor having low affinity to IgE Fc is called Fcεreceptor II (FcεRII). FcεRI is expressed in mast cells and basophils. In a case where IgE antibodies bound to FcεRI are cross-linked by polyvalent antigens, degranulation occurs in mast cells or basophils, thereby releasing various chemical transmitter substances including histamine. This release leads to an immediate allergic reaction.

The FcεRI is a membrane protein composed of one α chain, one β chain, and two γ chains linked by a disulfide bond. Among these chains, a portion to which IgE binds is the α chain (FcεRIα), and FcεRIα has a size of about 60 kDa. FcεRIα is composed of a hydrophobic domain existing inside the cell membrane and a hydrophilic domain existing outside the cell membrane. In particular, IgE binds to an extracellular domain of the α chain.

Specifically, the alpha subunit of the IgE Fc receptor may have the amino acid sequence set forth in NP_001992.1. In addition, the extracellular domain (FcεRIaECD) of the alpha subunit of the IgE Fc receptor may have the amino acid sequence of SEQ ID NO: 1. In the present specification, the extracellular domain of the alpha subunit of the IgE Fc receptor may be a fragment or variant of the extracellular domain of the alpha subunit of the IgE Fc receptor, as long as the fragment or variant is capable of binding to IgE.

Production of the variant can be achieved through a method of substituting, deleting, or adding one or more proteins in the wild-type FcεRIaECD (extracellular domain), as long as the method does not alter a function of the α chain of FcεRI. Such various proteins or peptides may be 90%, 91%, 92%, 93%, 94%, 95%, 96%, 97%, 98%, 99% or more identical to the amino acid sequence of SEQ ID NO: 1. In addition, the FcεRIaECD of SEQ ID NO: 1 may be encoded by a polynucleotide having the sequence of SEQ ID NO: 5.

Therefore, the extracellular domain itself of the alpha subunit of the IgE Fc receptor or a fragment of the extracellular domain of the alpha subunit of the IgE Fc receptor can be used as the polypeptide with a binding ability to IgE. An embodiment of the fragment of the extracellular domain may be in a form in which some of the amino acids at the N-terminus of the extracellular domain of the alpha subunit of the IgE Fc receptor are deleted. In an embodiment, the fragment of the extracellular domain may be one in which 1 to 30 amino acids at the N-terminus are deleted. In addition, the fragment of the extracellular domain may be one in which 5 to 25 amino acids at the N-terminus are deleted. In addition, the fragment of the extracellular domain may be in a form in which 1, 2, 3, 4, 5, 6, 7, 8, 9, or 10 amino acids at the N-terminus are deleted. In addition, an embodiment of the fragment of the extracellular domain may be in a form in which some of the amino acids at the C-terminus of the extracellular domain of the alpha subunit of the IgE Fc receptor are deleted. In an embodiment, the fragment of the extracellular domain may be one in which 1 to 30 amino acids at the C-terminus are deleted. In addition, the fragment of the extracellular domain may be one in which 5 to 25 amino acids at the C-terminus are deleted. In addition, the fragment of the extracellular domain may be in a form in which 1, 2, 3, 4, 5, 6, 7, 8, 9, or 10 amino acids at the C-terminus are deleted. In addition, an embodiment of the fragment of the extracellular domain may be in a form in which some of the amino acids at the N-terminus and C-terminus of the extracellular domain of the alpha subunit of the IgE Fc receptor are deleted. In an embodiment, the fragment of the extracellular domain may be in a form in which 1, 2, 3, 4, 5, 6, 7, 8, 9, or 10 amino acids, respectively, at the N-terminus and C-terminus are deleted.

However, the extracellular domain of the alpha subunit of the wild type IgE receptor, or a fragment thereof, is poorly persistent in the body. In order to improve this, the extracellular domain of the alpha subunit of the IgE receptor, or a fragment thereof, can be modified through various methods. As an embodiment of the modification method, polyethylene glycol (PEG) may be bound thereto. As another embodiment of the modification method, an Fc region of an immunoglobulin may be bound thereto. Here, in addition to a native form of immunoglobulin Fc, a modified Fc region may be used.

In addition, as used herein, the term "modified Fc region" means a region in which a part of an Fc portion of an antibody has been modified. Here, the term "Fc region" refers to a protein which contains heavy chain constant region 2 (CH2) and heavy chain constant region 3 (CH3) of an immunoglobulin, and does not contain variable regions of heavy and light chains and light chain constant region 1 (CH1) of an immunoglobulin. In particular, the modified Fc region means a region obtained by substituting some amino acids in the Fc region or by combining different types of Fc regions. Specifically, the modified Fc region may have the amino acid sequence of SEQ ID NO: 2. In addition, the modified Fc region of SEQ ID NO: 2 may be encoded by a polynucleotide having the sequence of SEQ ID NO: 6.

In addition, the modified Fc region of the present invention may be in the form of having sugar chains in a native form, increased sugar chains relative to a native form, or decreased sugar chains relative to a native form, or may be in the form of being sugar chain-removed. Immunoglobulin Fc sugar chains may be modified by conventional methods such as chemical methods, enzymatic methods, and genetic engineering methods using microorganisms.

Here, the modified Fc region of the present invention may be a region that lacks antibody dependent cellular cytotoxicity (ADCC) and complement dependent cytotoxicity (CDC) functions due to having no binding site for FcγR or C1q.

In addition, the FcεRIα-ECD or a fragment thereof may be linked to a wild-type Fc or modified Fc region via a linker. The linker may be composed of 20 to 60 consecutive amino acids, 25 to 50 consecutive amino acids, or 30 to 40 amino acids. In an embodiment, the linker may be composed of 30 or 49 amino acids as shown below. Also, the linker may contain at least one cysteine. Specifically, the linker may contain one, two, or three cysteines. Preferably, the linker contains one cysteine. In an embodiment, the linker may be a hinge region derived from an IgD antibody. In addition, the linker may be a hinge variant obtained by modifying the hinge region of the IgD antibody. The hinge variant may be obtained by modifying some in a hinge sequence of the IgD antibody in order to minimize generation of truncated forms during a protein production process.

In an embodiment, the hinge may contain the following sequence:

Arg Asn Thr Gly Arg Gly Gly Glu Glu Lys Lys Xaa1 Xaa2 Lys Glu Lys Glu Glu Gln Glu Glu Arg Glu Thr Lys Thr Pro Glu Cys Pro (SEQ ID NO: 17), where Xaa1 may be Lys or Gly, and Xaa2 may be Glu, Gly, or Ser. Specifically, the linker may have the amino acid sequence of SEQ ID NO: 3 and SEQ ID NO: 19, thereby minimizing generation of truncated forms during a protein production process.

In another embodiment, the hinge may contain the following sequence:

Ala Gln Pro Gln Ala Glu Gly Ser Leu Ala Lys Ala Thr Thr Ala Pro Ala Thr Thr Arg Asn Thr Gly Arg Gly Gly Glu Glu Lys Lys Xaa3 Xaa4 Lys Glu Lys Glu Glu Gln Glu Glu Arg Glu Thr Lys Thr Pro Glu Cys Pro (SEQ ID NO: 18), where Xaa3 may be Lys or Gly, and Xaa4 may be Glu, Gly, or Ser. Specifically, the linker may have the amino acid sequence of SEQ ID NO: 4, thereby minimizing generation of truncated forms during a protein production process.

In particular, in the linker having the amino acid sequence of SEQ ID NO: 4, at least one of Thr's may be glycosylated. Specifically, among the amino acids of SEQ ID NO: 18, the $13^{th}$, $14^{th}$, $18^{th}$, and $19^{th}$ Thr's may be glycosylated. Preferably, all four amino acids may be glycosylated. Here, the glycosylation may be O-glycosylation.

IgE$_{TRAP}$, which is an embodiment of the polypeptide with a binding ability to IgE of the present invention, means an Fc-fusion protein of an FcεRIα extracellular domain and an IgD/IgG4 hybrid Fc domain. IgE Fc receptor FcεR consists of α-chain, β-chain, and two identical disulfide-linked γ-chains. FcεRIβ and FcεRIγ have no extracellular domain. However, FcεRIα has two extracellular immunoglobulin-related domains and is involved in IgE binding. Thus, in order to produce a more safe and effective IgE inhibitor, a human FcεRIα extracellular domain was linked to a human IgD/IgG4 hybrid Fc domain (FIGS. 1 and 2) to produce IgE$_{TRAP}$. Unlike omalizumab, IgE$_{TRAP}$ does not bind to IgG receptors and is likely to decrease risk of IgG-mediated anaphylaxis (FIGS. 9 to 13). In addition, IgE$_{TRAP}$ has an affinity to IgE which is 69-fold higher than omalizumab. Therefore, IgE$_{TRAP}$ would be more safe and effective than omalizumab as a therapeutic agent for food allergy.

The polypeptide with a binding ability to IgE serves to block binding between FcεRIα on effector cells and IgE. The human IgD/IgG4 hybrid Fc contains the upper CH2 domain of IgD and the last CH2 and CH3 domains of IgG4, which do not have a binding site for FcγR or C1q (FIG. 1). However, this hybrid Fc may have a binding site for a neonatal Fc receptor (FIG. 1). In addition, a theoretical molecular weight of IgE$_{TRAP}$ in homodimeric form is about 97.6 kDa. However, an actual molecular weight thereof is about 150 kDa due to glycosylation (FIG. 6).

The polypeptide dimeric protein with a binding ability to IgE according to an embodiment of the present invention not only has excellent safety and persistence in the body as compared with conventionally used anti-IgE antibodies, but also binds to IgE very strongly due to having a binding capacity to IgE which is about 70-fold higher than the conventionally used anti-IgE antibody, omalizumab, which allows an extended administration cycle. In addition, the polypeptide dimeric protein according to the present invention is a substance obtained by applying a modified Fc, which has IgE alone as a single target and does not bind to an Fc gamma receptor, and thus lacks antibody dependent cellular cytotoxicity (ADCC) and complement dependent cytotoxicity (CDC) functions. Therefore, unlike conventional anti-IgE antibodies containing an IgG1 Fc region, the polypeptide dimeric protein does not bind to an Fc gamma receptor, and thus can inhibit release of mediators caused by being bound to the Fc gamma receptor on the surface of mast cells. Therefore, the polypeptide with a binding ability to IgE of the present invention can minimize severe side effects such as occurrence of anaphylaxis which can be caused by binding between IgG1 and Fc gamma receptor III on mast cells. Accordingly, the polypeptide dimeric protein according to the present invention can be utilized as a new pharmaceutical composition which can replace therapeutic agents containing a conventional anti-IgE antibody.

In addition, an embodiment of the polypeptide with a binding ability to IgE which is provided by the present invention may be in the form of a monomer. In particular, in a case where there is no cysteine in the linker used, the polypeptide may be in a monomeric form.

In addition, an embodiment of the polypeptide with a binding ability to IgE, which is provided by the present invention, may be a polypeptide dimer. Here, as described above, the polypeptide dimer may be in a form in which two monomers are bound to each other and each monomer is obtained by binding between an extracellular domain of an alpha subunit of an IgE Fc receptor and a modified Fc region. The polypeptide dimer may be in a form in which the same two monomers are bound to each other by cysteine located at a linker site. In addition, the polypeptide dimer may be in a form in which two different monomers are bound to each other. For example, in a case where the two monomers are different from each other, the polypeptide dimer may be in a form in which one monomer contains the extracellular domain of the alpha subunit of the IgE Fc receptor, and the other monomer contains a fragment of the extracellular domain of the alpha subunit of the IgE Fc receptor. Here, an embodiment of the monomer may have the amino acid sequence of SEQ ID NO: 20, SEQ ID NO: 21, or SEQ ID NO: 22.

In another aspect of the present invention, there is provided a pharmaceutical composition for treating or preventing an allergic disease, comprising a composition that contains, as active ingredients, probiotics and a polypeptide with a binding ability to IgE.

The probiotics and the polypeptide with a binding ability to IgE are as described above. A mixing amount of the probiotics and the polypeptide with a binding ability to IgE in the composition can be appropriately determined. In an embodiment, the probiotics in the composition may be contained in an amount of $1\times10^5$ cfu to $1\times10^{12}$ cfu. Alternatively, the probiotics in the composition may be contained in an amount of $1\times10^6$ cfu to $1\times10^{11}$ cfu, $1\times10^7$ cfu to $1\times10^{10}$ cfu, or $1\times10^9$ cfu to $5\times10^9$ cfu. In addition, the polypeptide with a binding ability to IgE may be contained in an amount of, but is not limited to, 0.1 ug to 5 mg, 0.5 ug to 1 mg, 1 ug to 500 ug, 10 ug to 400 ug, or 200 ug to 300 ug. In addition, a mixing ratio of the probiotics and the polypeptide with a binding ability to IgE in the composition can be appropriately altered.

In the present specification, "allergic disease" means a pathological symptom caused by an allergic reaction mediated by mast cell activation such as mast cell degranulation. Such allergic diseases include food allergy, atopic dermatitis, asthma, allergic rhinitis, allergic conjunctivitis, allergic dermatitis, allergic contact dermatitis, anaphylaxis, urticaria, pruritus, insect allergy, chronic idiopathic urticaria, drug allergy, and the like. In particular, the allergic diseases may be IgE-mediated.

In an embodiment of the present invention, a polypeptide with a binding ability to IgE which contains an FcεRIα extracellular domain blocks binding of IgE to FcεRI on effector cells through its binding with IgE, and thus can be referred to as IgE$_{TRAP}$. In addition, it was identified that *B. longum* can improve a therapeutic effect of IgE$_{TRAP}$ and remarkably decrease a dose of IgE$_{TRAP}$ required for treatment.

In the composition for treating or preventing an allergic disease of the present invention, an active ingredient may be contained in any amount (effective amount) depending on use, formulation, blending purpose, and the like, as long as the active ingredient can exhibit anti-allergic activity. A typical effective amount of the active ingredient may be determined within a range of 0.001% by weight to 20.0% by weight based on a total weight of the composition. Here, "effective amount" refers to an amount of an active ingredient which is capable of inducing an anti-allergic effect. Such an effective amount can be determined experimentally within the ordinary skill of those skilled in the art.

Here, the pharmaceutical composition may further contain a pharmaceutically acceptable carrier. For the pharmaceutically acceptable carrier, any carrier can be used as long as the carrier is a non-toxic substance suitable for delivery to a patient. Distilled water, alcohol, fat, wax, and an inert solid may be contained as carriers. Pharmacologically acceptable adjuvants (buffers and dispersants) may also be contained in the pharmaceutical composition. In particular, any pharmaceutically acceptable formulation can be used as long as the probiotics and the polypeptide with a binding ability to IgE can maintain their stability in the formulation.

Specifically, the pharmaceutical composition of the present invention contains, in addition to active ingredients, a pharmaceutically acceptable carrier, and may be made into an oral or parenteral formulation depending on a route of administration by a conventional method known in the art. Here, the term "pharmaceutically acceptable" means not having more toxicity than a subject to be applied (prescribed) can accommodate without inhibiting activity of the active ingredient.

In a case where the pharmaceutical composition of the present invention is made into an oral formulation, the pharmaceutical composition may be made into formulations such as powders, granules, tablets, pills, sugar coating tablets, capsules, liquids, gels, syrups, suspensions, and wafers, together with suitable carriers, in accordance with methods known in the art. Here, examples of suitable pharmaceutically acceptable carriers can include sugars such as lactose, glucose, sucrose, dextrose, sorbitol, mannitol, and xylitol, starches such as corn starch, potato starch, and wheat starch, celluloses such as cellulose, methylcellulose, ethylcellulose, sodium carboxymethyl cellulose, and hydroxypropylmethyl cellulose, polyvinyl pyrrolidone, water, methylhydroxybenzoate, propylhydroxybenzoate, magnesium stearate, mineral oil, malt, gelatin, talc, polyol, vegetable oil, and the like. In a case of being made into preparations, the preparations can be carried out, as necessary, by including diluents and/or excipients such as a filler, an extender, a binder, a wetting agent, a disintegrant, and a surfactant.

In a case where the pharmaceutical composition of the present invention is made into a parenteral formulation, the pharmaceutical composition may be made into preparations in the form of injections, transdermal drugs, nasal inhalers, and suppositories, together with suitable carriers, in accordance with methods known in the art. In a case of being prepared into injections, sterilized water, ethanol, polyol such as glycerol and propylene glycol, or a mixture thereof may be used as a suitable carrier. For the carrier, isotonic solutions such as Ringer's solution, phosphate buffered saline (PBS) containing triethanolamine, sterile water for injection, and 5% dextrose, and the like may be preferably used.

Preparation of the pharmaceutical composition is known in the art, and specifically, reference can be made to Remington's Pharmaceutical Sciences (19th ed., 1995) and the like. The document is considered part of the present specification.

A preferable daily dosage of the pharmaceutical composition of the present invention is ranged from 0.01 ug/kg to 10 g/kg, and preferably from 0.01 mg/kg to 1 g/kg, depending on the patient's condition, body weight, sex, age, disease severity, or route of administration. Administration may be carried out once or several times a day. Such a dosage should in no way be interpreted as limiting the scope of the present invention.

The subject to which the composition of the present invention can be applied (prescribed) is a mammal and a human, with a human being particularly preferred. The composition for anti-allergy of the present invention may further comprise, in addition to the active ingredient, any compound or natural extract, on which safety has already been verified and which is known to have anti-allergic activity, for the purpose of raising and reinforcing the anti-allergic activity. Here, the pharmaceutical composition may further comprise extracellular endoplasmic reticulum isolated from *Bifidobacterium longum* KACC 91563.

In yet another aspect of the present invention, there is provided a health functional food composition for ameliorating or alleviating an allergic symptom, comprising a composition that contains, as active ingredients, probiotics and a polypeptide with a binding ability to IgE. Here, the food composition may further comprise, as an active ingredient, extracellular endoplasmic reticulum isolated from *Bifidobacterium longum* KACC 91563.

Meanwhile, the food composition of the present invention may further comprise a sitologically acceptable carrier. In addition, the food composition may be used together with another food or food ingredient, and may be suitably used according to conventional methods. A mixing amount of the active ingredient can be suitably determined according to its intended use (prevention, health, or therapeutic treatment).

There is no particular limitation on a type of the food. Examples of the food include meats, sausages, bread, chocolates, candies, snacks, confections, dairy products including ice cream, various soups, beverages, tea, drinks, alcoholic beverages, and vitamin complexes. All functional health foods in a conventional sense are included. Foods to which the above substances may be added contain ingredients that are typically added during manufacture, and examples of the ingredients include proteins, carbohydrates, fat, nutrients, flavoring agents, and seasonings. The above-mentioned carbohydrates are typical sugars, for example, a monosaccharide such as glucose and fructose, a disaccharide such as maltose and sucrose, and a polysaccharide such as dextrin and cyclodextrin, and sugar alcohol such as xylitol, sorbitol, and erythritol. As the flavoring agent, a natural flavoring agent such as thaumatin and a stevia extract, a synthetic flavoring agent such as saccharin and aspartame, or the like may be used.

For example, in a case where the food composition of the present invention is prepared as a drink, citric acid, liquid fructose, sugar, glucose, acetic acid, malic acid, juice, extract, or the like may be further contained in addition to the composition of the present invention.

In addition to the above, the composition of the present invention may contain various nutrients, vitamins, electrolytes, flavors, colorants, pectic acid and salts thereof, alginic acid and salts thereof, organic acids, protective colloid thickeners, pH adjusting agents, stabilizers, preservatives, glycerin, alcohol, carbonating agent used in carbonated beverages, and the like. In addition, the composition of the present invention may contain flesh for the production of fruit juice beverages and vegetable beverages. These ingredients may be used independently or in admixture.

In addition, the food composition of the present invention may fall within any product category in legal or functional classification as long as the food composition complies with the enforcement regulations at the time of being manufactured and distributed. For example, the food composition may be a health functional food according to the Health Functional Foods Act, or may fall within confectioneries, beans, teas, beverages, special-purpose foods, or the like according to each food type in the Food Code of Food Sanitation Act (standards and specifications for food, notified by Food and Drug Administration). With regard to other food additives that may be contained in the food composition of the present invention, reference can be made to the Food Code or the Food Additive Code according to the Food Sanitation Act.

In still yet another aspect of the present invention, there is provided a kit for treating or preventing an allergic disease, comprising a first composition that contains probiotics; and a second composition that contains a polypeptide with a binding ability to IgE. Here, the second composition may be a composition for subcutaneous or intravenous administration.

In still yet another aspect of the invention, there is provided a method for treating or preventing an allergic disease, comprising a step of administering probiotics; and administering a polypeptide with a binding ability to IgE.

The probiotics are as described above and may be orally administered. Here, the polypeptide with a binding ability to IgE may be orally administered, and may be parenterally administered. Here, parenteral administration can be carried out by a method such as subcutaneous administration, intravenous administration, mucosal administration, or the like.

In a mouse food allergic model, it has been shown that $IgE_{TRAP}$ not only lowers a free IgE level but also decreases the number of mast cells, thereby alleviating food allergic symptoms (FIGS. 21 to 26). A decreased number of mast cells caused by $IgE_{TRAP}$ is expected to be due to the fact that IgE increases the number of mast cells by increasing a survival rate of the mast cells. In addition, over-proliferation of goblet cells in the small intestine was significantly inhibited by administration of $IgE_{TRAP}$ and B. longum alone, and was even further inhibited at the time of combined administration (FIGS. 23 to 26). Since Th2 cytokines such as IL-13 are known to induce over-proliferation of goblet cells, it is expected that $IgE_{TRAP}$, B. longum, and a combination thereof mitigate an environment for Th2 cytokines in the small intestine. As support for this, $IgE_{TRAP}$ and B. longum showed a tendency to decrease mRNA expression of IL-33, which is involved in promoting IL-13 secretion, in the small intestine, by activating type 2 innate lymphoid cells (ILC2s); and a combination thereof significantly decreased the expression of IL-33 in a more effective manner (FIG. 28). In addition, IL-33 is not only secreted in IgE-activated mast cells but also involved in promoting degranulation of mast cells. Thus, IL-33 has a close correlation with severity of food allergies. This suggests that $IgE_{TRAP}$ and B. longum can ameliorate food allergic symptoms by various mechanisms.

Figure 19B:
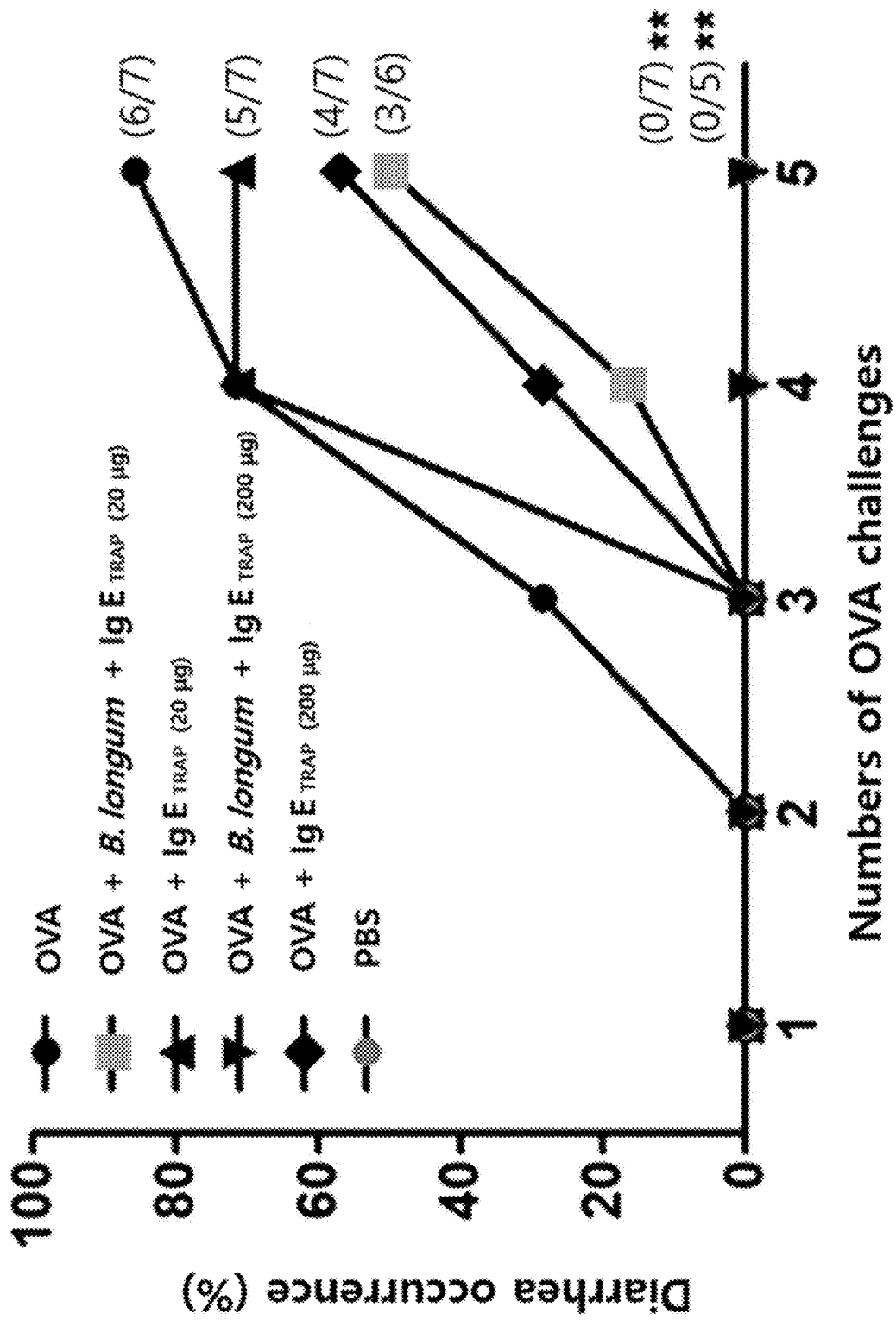
FIG. 19B illustrates a graph obtained by identifying effects of combined administration of probiotics and the polypeptide dimeric protein ($IgE_{TRAP}$) with a binding ability to IgE depending on increased doses in a food allergy-induced disease model. Effects of $IgE_{TRAP}$, *B. longum*, and a combination thereof to inhibit food allergic diarrhea are shown. n=14 mice per group, OVA vs OVA+*B. longum*+$IgE_{TRAP}$ (20 µg), OVA vs OVA+*B. longum*+$IgE_{TRAP}$ (200 µg), and OVA vs PBS: **P<0.001

Previously, B. longum has been reported to induce apoptosis of mast cells and to improve food allergic symptoms, which is consistent with the results of the present inventors. However, daily administration of B. longum for the treatment of food allergy was less effective than administration of $IgE_{TRAP}$ alone. However, B. longum remarkably improved a therapeutic effect of $IgE_{TRAP}$ (FIG. 18), and $IgE_{TRAP}$ used in combination with B. longum exhibited a therapeutic effect which is similar to that obtained by administration of $IgE_{TRAP}$ alone at a 10-fold higher dose (FIG. 19B). In addition, it has been reported that some intestinal bacteria can ameliorate an allergic disease by increasing Treg cells or decreasing levels of IgE and Th2 cytokines. Thus, other probiotics in addition to B. longum are expected to be capable of improving a therapeutic effect of $IgE_{TRAP}$. Indeed, it was identified that an elevated therapeutic effect is exhibited at the time of combined administration of various types of probiotics and $IgE_{TRAP}$ (FIGS. 29 to 34).

In still yet another aspect of the present invention, there is provided a method for treating or preventing an allergic disease, comprising a step of administering, to an individual, the polypeptide with a binding ability to IgE and the probiotics in combination. The individual may be a mammal, preferably a human. Here, administration may be performed orally or parenterally. Here, the polypeptide with a binding ability to IgE and the probiotics can be prepared into suitable formulations for oral administration. In addition, parenteral administration may be performed by methods such as subcutaneous administration, intravenous administration, mucosal administration, and muscular administration.

DETAILED DESCRIPTION OF THE INVENTION

Hereinafter, the present invention will be described in more detail with reference to the following examples. However, the following examples are intended to merely illustrate the present invention, and the scope of the present invention is not limited only thereto.

Materials and Methods

Cell Line Construction for IgETRAP and Purification Thereof

A nucleotide sequence of $IgE_{TRAP}$ was constructed by linking the C-terminus ($26^{th}$ to $205^{th}$) of the FcεRIα extracellular domain to the N-terminus of the IgD/IgG4 hybrid Fc domain (IgD, $133^{rd}$ to $170^{th}$; IgG4, $121^{st}$ to $327^{th}$). The protein was expressed in dihydrofolate reductase-deficient Chinese hamster ovary DG44 cells. $IgE_{TRAP}$ was purified using the HITRAP™ rProtein A FF column (GE Healthcare), and its purity was identified by SDS-PAGE under reducing and non-reducing conditions.

3D Structure Modeling

A structural model of $IgE_{TRAP}$ was designed using WinCoot and was built with the PyMOL software on the basis of information on FcεRIα (PDB accession 1F6A) and IgD/IgG4 Fc (PDB accession 1ADQ) of the Protein Data Bank.

Surface Plasmon Resonance (SPR) Assay

SPR assay was conducted using the PROTEON™ XPR36 (Bio-Rad) apparatus. A degree of binding of omalizumab and $IgE_{TRAP}$ to human IgE (Calbiochem) was identified using kinetic analysis. 850 response units (RUs) of omalizumab in acetate buffer (pH 5.5) and 500 RUs of IgE$_{TRAP}$ in acetate buffer (pH 4.0) were immobilized on the PROTEON™ GLC sensor chip (Bio-Rad). PBS containing TWEEN®-20 (polysorbate 20) was used as a running buffer and a flow rate was set at 30 ul/min. A graph of each data set was analyzed using the PROTEON™ Manager software (Bio-Rad).

Biolayer Interferometry (BLI) Assay

A degree of binding of IgE$_{TRAP}$ and omalizumab to IgG receptors was identified using the OCTET® RED384 system (Pall ForteBio, CA, USA). FcγRI, FcγRIIA, FcγRIIB, FcγRIIIA, and FcγRIIIB recombinant proteins (R & D Systems Inc., 5 μg/ml) which had been diluted in 300 mM acetate buffer (pH 5) were immobilized on the Amine Reactive 2 Generation (AR2G) biosensor activated by a combination of 400 mM EDC and 10 mM sulfo-NHS. Then, association with and dissociation from IgE$_{TRAP}$ and omalizumab at various concentrations were measured, respectively, for 300 seconds. Here, the kinetic buffer used was PBS containing 0.1% TWEEN®-20 (polysorbate 20) and 1% bovine serum, and all experiments were carried out at 30° C. with a sample plate shaker at a rate of 1,000 rpm.

β-Hexosaminidase Release Assay

Bone marrow-derived mast cells (BMMCs) were cultured at 37° C. in RPMI containing 10% heat-inactivated FBS, 10 ng/mL mouse IL-3 (PeproTech, Inc.), and 50 ng/mL mouse SCF (PeproTech, Inc.). Before analysis, 1 ug/mL of anti-dinitrophenyl IgE (Sigma-Aldrich) and various concentrations of IgE$_{TRAP}$ were incubated at room temperature for 30 minutes. The bone marrow-derived mast cells were incubated in a mixture of anti-dinitrophenyl IgE (Sigma-Aldrich) and IgE$_{TRAP}$ at 37° C. for 30 minutes, and 0.1 μg/ml of anti-dinitrophenyl IgE was added thereto. The resultant was incubated again at 37° C. for 30 minutes. Culture supernatant was collected and incubated with 3 mM p-nitrophenyl-N-acetyl-β-D-glucosaminide at 37° C. for 20 minutes. 0.1 M sodium carbonate buffer (pH 10) was added to stop the reaction, and absorbance at 405 nm was measured. A ratio of released β-hexosaminidase was calculated by comparison with a total intracellular content of BMMCs dissolved with 0.1% Triton X-100.

Food Allergy Induction and Administration of *B. longum*

On days 0 and 14, 50 ug of OVA (Grade V; Sigma-Aldrich) and 1 mg of aluminum potassium sulfate adjuvant (Sigma-Aldrich) were administered intraperitoneally into mice. After 14 days, the mice were orally administered 50 mg of OVA (Grade III; Sigma-Aldrich) 5 times at 2-day intervals. The mice were fasted for about 4 to 5 hours prior to oral administration of OVA. Diarrhea occurrence was evaluated by monitoring the mice for up to 1 hour after OVA inoculation. *B. longum* was lyophilized and mixed with powdered mouse feed at 3×10$^9$ cfu/g. The mice were allowed ad libitum access to the feed. In order to maintain freshness, the mouse feed mixed with *B. longum* was replaced every 2 to 3 days.

Histology

The jejunum of the small intestine was fixed with 4% paraformaldehyde and embedded in paraffin to make a block. Then, a paraffin section slide was produced. The slide was deparaffinized and mast cells were stained with a naphthol AS-D chloroacetate esterase kit (Sigma-Aldrich). For goblet cells, the slide was stained with a periodic acid-Schiff stain kit (ScyTek Laboratories, Inc.). An image of the stained slide was taken using Pannoramic MIDI (3D HISTECH Ltd.).

ELISA

Mouse Total IgE ELISA kit (BioLegend) and MCPT-1 ELISA kit (Invitrogen) were used according to the manufacturers' protocol to measure total concentrations of IgE and MCPT-1 in mouse serum. In order to measure free IgE, the plate was coated with 1 mg/mL of IgE$_{TRAP}$ and allowed to react overnight at 4° C. The rest of the analysis was conducted according to the manufacturer's protocol for the Mouse Total IgE ELISA kit.

Statistical Analysis

Statistical analysis for all data was performed using the GraphPad Prism 5 software (GraphPad Software Inc.). Kaplan-Meier survival curve analysis with log-rank (Mantel-Cox) assay was used to calculate diarrhea occurrence. One-way ANOVA with Newman-Keuls multiple comparison test was used to identify meaningful differences in the test.

I. Preparation and Characterization of IgETRAP

Example 1. Preparation of Polypeptide Containing FcεRIα-ECD and Modified Fc Region A C-terminal modified polypeptide of the extracellular domain (FcεRIα-ECD) of the alpha subunit of the IgE Fc receptor was prepared according to the method disclosed in U.S. Pat. No. 7,867,491.

First, a fusion protein that contains the extracellular domain of the α-chain of FcεRI having the amino acid sequence of SEQ ID NO: 1 and the modified immunoglobulin Fc of SEQ ID NO: 2 was prepared. Specifically, in order to express a protein (FcεRIαECD-Fc1), a protein (FcεRIαECD-Fc2), and a protein (FcεR1αECD-Fc3), which were linked, respectively, via a hinge of SEQ ID NO: 19, a hinge of SEQ ID NO: 3, and a hinge of SEQ ID NO: 4, cassettes obtained by linking the gene encoding each protein were cloned into the pAD15 vectors (Genexin, Inc.) to construct FcεRIαECD-Fc protein expression vectors. Then, each of the expression vectors was transduced into CHO DG44 cells (from Dr. Chasm, Columbia University, USA).

Here, at the time of being transduced into the cell line, an expression vector obtained by cloning an α-2,6-sialic acid transferase gene into the pCI Hygro vector (Invitrogen) was simultaneously transduced to separately prepare cell lines which were capable of expressing FcεRIαECD-Fc2ST and FcεRIα ECD-Fc3ST proteins to which sialic acid was added.

As a primary screening procedure, HT selection was carried out using 5-hydroxytryptamine (HT)-free 10% dFBS medium (Gibco, USA, 30067-334), MEMα medium (Gibco, 12561, USA, Cat No. 12561-049), and HT+ medium (Gibco, USA, 11067-030). Then, methotrexate (MTX) amplification was performed using HT-selected clones to amplify productivity using the dihydrofolate reductase (DHFR)-system.

After completion of the MTX amplification, subculture was carried out about 1 to 5 times for cell stabilization for the purpose of evaluation of productivity. Thereafter, unit productivity evaluation of the MTX-amplified cells was performed. The results are shown in Table 1 below.

TABLE 1

| Version | Media | MTX concentration | Productivity 3-day culture ug/mL | Productivity 3-day culture ug/10⁶ cells | Batch culture (mg/ml) |
|---|---|---|---|---|---|
| FcεRIαECD-Fc2 | Ex-cell | 500 nM | 37.23 | 20.9 | 225 |
| FcεRIαECD-Fc2 + a2,6-ST | DHFR | 100 nM | 45.4 | 25.1 | 338.2 |
| FcεRIαECD-Fc3 | | 2 uM | 27.0 | 16.9 | 180.4 |
| FcεRIαECD-Fc3 + a2,6-ST | | 1 uM | 17.5 | 10.2 | 101.7 |

As shown in Table 1, the FcεRIαECD-Fc3 cell line exhibited productivity of 16.9 ug/10⁶ cells after the methotrexate amplification at 2 uM. On the other hand, the FcεRIαECD-Fc3 cell line (FcεRIαECD-Fc3ST) co-transduced with 2,6-sialic acid transferase exhibited productivity of 10.2 ug/10⁶ cells after the methotrexate amplification at 1 uM. In addition, the FcεRIαECD-Fc2 cell line exhibited productivity of 20.9 ug/10⁶ cells under the methotrexate amplification condition at 0.5 uM. In addition, the FcεRIαECD-Fc2 cell line (FcεRIαECD-Fc2ST) co-transduced with 2,6-sialic acid transferase exhibited productivity of 25.1 ug/10⁶ cells after the methotrexate amplification at 0.1 uM. That is, it was identified that the FcεRIαECD-Fc2 cell line co-transfected with 2,6-sialic acid transferase, which had been selected under the methotrexate amplification condition at 0.1 uM, exhibited the most excellent productivity.

Example 2. Purification of FcεRIα ECD Fusion Protein and Identification of Purity Thereof Among the cell lines selected in Example 1 above, i) FcεRIαECD-Fc3, ii) FcεRIαECD-Fc3ST, and iii) FcεRIαECD-Fc2ST were cultured at a 60 ml scale by a batch culture method. The resulting cultures were purified using a Protein-A affinity column, and then purified proteins were subjected to SDS-PAGE and size-exclusion HPLC (SE-HPLC) to identify purity of the proteins.

As shown in FIGS. 3A and 3B, it was identified that all respective proteins purified by the SE-HPLC method have purity of 93% or higher. In addition, as a result of SDS-PAGE analysis, it was identified that proteins having sizes of about 150 kDa and about 75 kDa were detected, respectively, in the non-reducing and reducing conditions (FIG. 3A, Lanes 1 to 6). From this, it was found that the Fc-bound FcεRIαECD forms a dimer. In addition, no impurities such as a truncated form were observed in the SDS-PAGE results. In particular, even after the process of thawing/freezing (FIG. 3A, Lanes 7 to 9), it was identified that all proteins have purity of 93% or higher, and has no impurities. Here, Gel-IEF was performed under the following test conditions to identify a degree of sialic acid content in the proteins following introduction of the sialic acid transferase. From this, it was identified that a content of acidic proteins was increased due to increased sialic acid content.

TABLE 2

| Test conditions | |
|---|---|
| Gel | pH3-10 IEF gel 1.0 mm |
| Sample buffer | IEF sample buffer (2×) |
| Loading condition | 100 V 1 hr, 200 V 1 hr, 500 V 2 hr |

In order to identify reproducibility of purification yield, the FcεRIαECD-Fc2ST cell line was batch-cultured in a 1 L flask at a 250 ml scale and purified using a Protein-A affinity column. Subsequently, the culture supernatant and the purified product were subjected to running on a 4% to 15% TGX™ gel (Bio-Rad Laboratories, Inc.) for 30 minutes at a condition of Tris-Glycine SDS (TGS) buffer and 200 V, and then subjected to SDS PAGE analysis. As a result, it was identified that proteins with very high purity (98% or higher) were purified even by only the first step purification and proteins were expressed with very high purity even in the culture supernatant. This indicates that process development steps can be simplified in developing the FcεRIαECD-Fc protein, which was expressed in the cell line in question, into a medical product, and as a result, it is highly likely for the development cost of the medical product to be remarkably decreased.

Experimental Example 1. Identification of Binding Ability of FcεRIα ECD Fusion Protein to IgE A binding ability to IgE was comparatively measured for the four proteins, i) FcεRIαECD-Fc2, ii) FcεRIαECD-Fc2ST, iii) FcεRIαECD-Fc3, and iv) FcεRIαECD-Fc3ST which had been purified through the method of Example 2 above, and the commercially available anti-IgE antibody, XOLAIR™ (omalizumab)). Specifically, the binding ability to IgE was measured by coating IgE on the channel of the Protein GLC sensor chip (Bio-Rad Laboratories, Inc.), and causing omalizumab or each FceR1αECD-Fc protein at various concentrations to flow at a rate of 30 µl per minute.

The experiments were conducted by identifying zero base using 25 mM NaOH as a regeneration buffer, and then repeating the above steps. Thereafter, a binding curve was identified using a protein binding analyzer (PROTEON™ XPR36, Bio-Rad Laboratories, Inc., USA). The results are shown in Table 3, and FIGS. 7 and 8. IgE$_{TRAP}$ in FIG. 8 means FceR1αECD-Fc2ST, which is an embodiment of the polypeptide with a binding ability to IgE of the present invention.

TABLE 3

| Samples items Drug type | | | FcεRIa ECD-Fc Fc fusion protein | Omalizumab Anti-IgE Ab | Remarks |
|---|---|---|---|---|---|
| Binding affinity | ka (association rate) | Fc2 | 2.14 × 10⁵ | 4.05 × 10⁵ | 1.9-fold weaker than omalizumab |
| | | Fc2ST | 2.64 × 10⁵ | | 1.5-fold weaker than omalizumab |
| | | Fc3 | 1.98 × 10⁵ | | 2.0-fold weaker than omalizumab |
| | | Fc3ST | 2.40 × 10⁵ | | 1.7-fold weaker than omalizumab |
| | kd (dissociation | Fc2 | 8.29 × 10⁻⁵ | 6.02 × 10⁻³ | 73-fold better than omalizumab |
| | | Fc2ST | 5.69 × 10⁻⁵ | | 106-fold better than omalizumab |

TABLE 3-continued

| Samples items Drug type | | FcεRIa ECD-Fc Fc fusion protein | Omalizumab Anti-IgE Ab | Remarks |
|---|---|---|---|---|
| rate) | Fc3 | $1.33 \times 10^{-4}$ | | 45-fold better than omalizumab |
| | Fc3ST | $1.49 \times 10^{-4}$ | | 40-fold better than omalizumab |
| KD | Fc2 | $3.88 \times 10^{-10}$ | $1.49 \times 10^{-8}$ | 38-fold better than omalizumab |
| (kd/ka) | Fc2ST | $2.16 \times 10^{-10}$ | | 69-fold better than omalizumab |
| | Fc3 | $6.72 \times 10^{-10}$ | | 22-fold better than omalizumab |
| | Fc3ST | $6.21 \times 10^{-10}$ | | 24-fold better than omalizumab |

As shown in Table 3, the association rate (ka) value of the polypeptide dimer according to an embodiment of the present invention was measured to be 1.5- to 2.0-fold lower than that of omalizumab. That is, it was found that a binding ability thereof to substances other than IgE was 1.5- to 2.0-fold lower than that of omalizumab. In addition, the dissociation rate (kd) value of the polypeptide dimer according to an embodiment of the present invention was measured to be 40- to 106-fold higher than that of omalizumab. In addition, as shown in FIGS. 7 and 8, it was able to identify that omalizumab lost its binding to IgE in a case where a certain period of time has passed after the binding, whereas once the polypeptide dimer of the FcεRIαECD fusion protein of the present invention binds to IgE, the polypeptide dimer was not separated from IgE. That is, it can be seen that the polypeptide dimer of the present invention is not easily separated from IgE, and has a much better ability to maintain its bound state than omalizumab. As a result, it was found that the polypeptide dimer according to an embodiment of the present invention has an equilibrium dissociation constant (KD<kd/ka>) value which was 22- to 69-fold higher than omalizumab.

From this, it can be seen that the FcεRIαECD fusion protein of the present invention has a remarkably increased binding ability to IgE as compared with omalizumab. In particular, it was identified that the FcεRIαECD-Fc2 (FcεRIαECD-Fc2ST) to which sialic acid was added exhibits the highest IgE-binding capacity which was 69-fold higher than omalizumab. In particular, for FceR1αECD-Fc2ST, the association rate (Ka) and dissociation rate (Kd) of $IgE_{TRAP}$p were about 1.5-fold and 94.5-fold lower than omalizumab, respectively (FIGS. 7 and 8, and Table 4). It has previously been reported that IgE was dissociated very slowly from FcεRIα. It was identified that $IgE_{TRAP}$ was also dissociated very slowly (FIG. 8). As a result, a binding ability of $IgE_{TRAP}$ to human IgE was 69-fold higher than omalizumab (FIG. 8 and Table 4).

TABLE 4

| | Ka (M$^{-1}$ S$^{-1}$) | Kd (S$^{-1}$) | KD (M) |
|---|---|---|---|
| $IgE_{TRAP}$ | $2.64 \times 10^5$ | $5.69 \times 10^{-5}$ | $2.15 \times 10^{-10}$ |
| Omalizumab | $4.05 \times 10^5$ | $6.02 \times 10^{-3}$ | $1.49 \times 10^{-8}$ |
| Comparison of KD [Omalizumab/$IgE_{TRAP}$] | | | About 69-fold |

Experimental Example 2. Identification of Binding Ability of IgETRAP to IgG-Mediated IgG Receptors $IgE_{TRAP}$ does not bind to low-affinity IgG receptors associated with IgG-mediated anaphylaxis. Since anaphylaxis, a major side effect of omalizumab, was expected to be caused by the possibility of binding to a low-affinity IgG receptor, BLI assay was used to check a binding ability of $IgE_{TRAP}$ to IgG receptors while using omalizumab as a control. Specifically, a degree of binding of $IgE_{TRAP}$ and omalizumab to IgG receptors was identified using the OCTET© RED384 system (Pall ForteBio, CA, USA).

FcγRI, FcγRIIA, FcγRIIB, FcγRIIIA, and FcγRIIIB recombinant proteins (R & D Systems Inc., 5 μg/ml) which had been diluted in 300 mM acetate buffer (pH 5) were immobilized on the Amine Reactive 2 Generation (AR2G) biosensor activated by a combination of 400 mM EDC and 10 mM sulfo-NHS. Then, association with and dissociation from $IgE_{TRAP}$ and omalizumab at various concentrations were measured, respectively, for 300 seconds. Here, the kinetic buffer used was PBS containing 0.1% TWEEN©-20 (polysorbate 20) and 1% bovine serum, and all experiments were carried out at 30° C. with a sample plate shaker at a rate of 1,000 rpm.

As expected, omalizumab showed a significant binding ability to FcγRI, a high-affinity IgG receptor, as well as to low-affinity IgG receptors such as FcγRIIA, FcγRIIB, FcγRIIIA, and FcγRIIIB (FIGS. 9 to 14). This means that, unlike omalizumab, $IgE_{TRAP}$ cannot bind to IgG receptors such as FcγRIIA and FcγRIII, and thus has a very low risk of inducing IgG-mediated anaphylaxis (FIGS. 9 to 14). Binding abilities of omalizumab and $IgE_{TRAP}$ to the IgG receptors were quantified and shown in FIG. 14.

Experimental Example 3. Identification of Activity of FcεRIα ECD Fusion Protein Through Beta-Hexosaminidase Assay in Mouse Bone Marrow-Derived Mast Cells Beta-hexosaminidase assay was performed for in vitro activity analysis of the FcεRIαECD fusion protein of the present invention. Specifically, the FcεRIαECD-Fc2 protein according to an embodiment of the present invention was mixed, at each concentration, with mouse IgE (1 ug/mL), and incubated at room temperature (20° C.) for 30 minutes to prepare samples. Mouse bone marrow-derived mast cells in culture for mast cell activation were washed with Hank's balanced salt solution (HBSS) buffer to remove the medium, and the number of cells was measured. Then, an adjustment was made so that 5×10$^5$ cells were injected into 40 μL of HBSS buffer.

Then, 50 uL of the sample solution prepared through the pre-incubation was added to the activated mast cells. Then, the resultant was incubated in a 5% $CO_2$ incubator at 37° C. for 30 minutes. Subsequently, after the addition of each 10 μL of DNP (2,4-dinitrophenol, 100 ng/mL), which is a foreign antigen, incubation was performed again at 37° C. for 30 minutes in 5% $CO_2$, and then 30 μL of the supernatant was separated. 30 uL of the separated supernatant and 30 uL of the substrate (4-nitrophenyl N-acetyl-β-D-glucosaminide, 5.84 mM) were mixed well, and then incubated at 37° C. for 20 minutes in 5% $CO_2$. Then, 140 μL of 0.1 M sodium carbonate buffer (pH 10) as a stop solution was added to terminate the reaction. Thereafter, absorbance at 405 nm was measured to identify a secretion amount of β-hexosaminidase secreted by the foreign antigen in the activated mast cells. The results are shown in FIG. 15A.

Figure 15A:
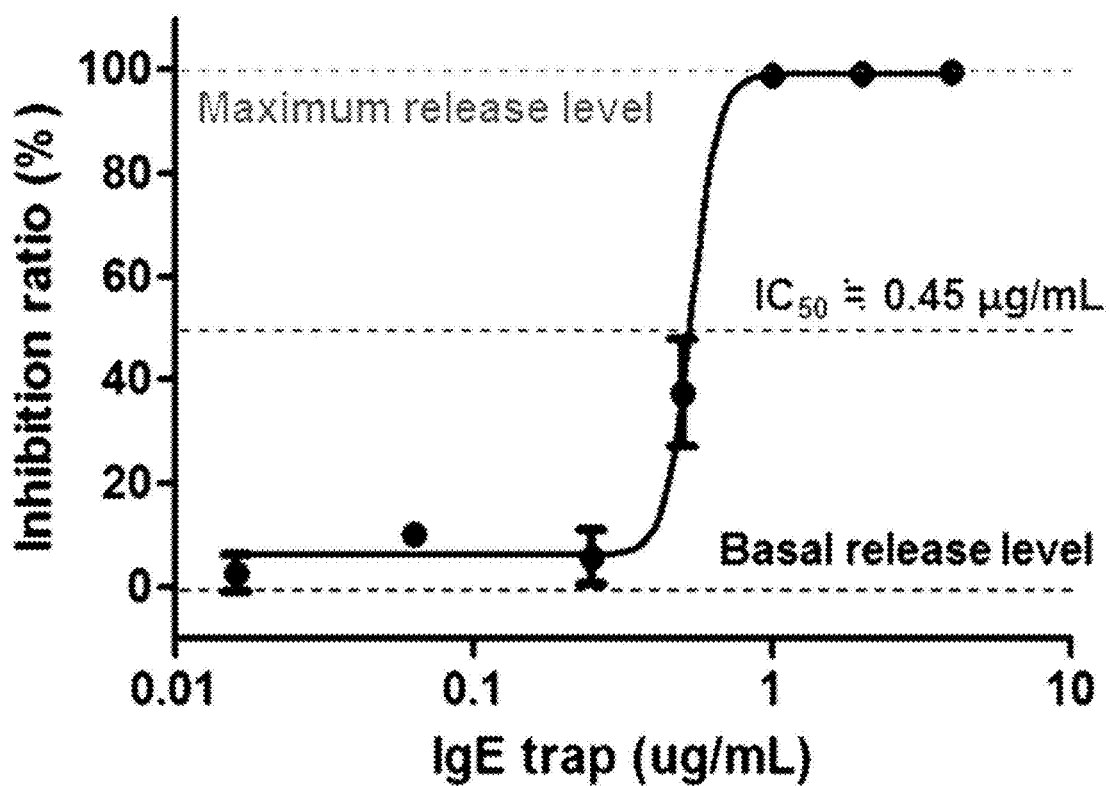
FIG. 15A illustrates a graph showing an inhibitory ability, on activity of mouse-derived mast cells, of the polypeptide dimeric protein ($IgE_{TRAP}$) according to an embodiment of the present invention depending on concentrations thereof.

IgE$_{TRAP}$ inhibited degranulation of mast cells in a dose-dependent manner with 0.45 μg/ml of IC$_{50}$ (concentration of drug necessary to show inhibitory effect of 50%) in the presence of 1 μg/ml of mouse IgE (FIG. 15A). IgE$_{TRAP}$ completely inhibited degranulation of the bone marrow-derived mast cell at a molecular ratio of IgE:IgE$_{TRAP}$ of 0.79 (Table 5).

TABLE 5

| Anti-DNP IgE | 1 ug/mL (=5.26 nM) | | | | | | | |
|---|---|---|---|---|---|---|---|---|
| IgE$_{TRAP}$ (ug/mL) | 0 | 0.016 | 0.063 | 0.25 | 0.5 | 1 | 2 | 4 |
| IgE$_{TRAP}$ (nM) | 0 | 0.11 | 0.42 | 1.67 | 3.33 | 6.67 | 13.3 | 26.7 |
| [IgE/IgE$_{TRAP}$] molar ratio | 0 | 47.8 | 12.5 | 3.15 | 1.58 | 0.79 | 0.40 | 0.20 |
| Average inhibition ratio (%) | 0 | 2.12 | 12.4 | 13.8 | 49.4 | 99.3 | 99.4 | 99.8 |

Specifically, as shown in FIG. 15A, the polypeptide dimer of an embodiment of the present invention exhibited a mast cell inhibition ratio of about 49.4% in a case of having half (0.5 ug/mL) the concentration of mouse IgE, and exhibited a mast cell inhibition ratio of about 99.4% in a case of having the same concentration (1 ug/mL) of mouse IgE. That is, it can be seen that IgE-induced activity of bone marrow-derived mast cells is greatly suppressed by the FcεRIa-ECD polypeptide dimer of the present invention.

Experimental Example 4. Comparison of Activity of FcεRIα ECD Fusion Protein and Anti-Human IgE Antibody Using β-Hexosaminidase Assay in Human FcεRI-Expressing Bone Marrow-Derived Mast Cells β-Hexosaminidase assay was conducted to identify superiority of the FcεRIα ECD fusion protein relative to XOLAIR™ (omalizumab) through in vitro activity analysis. The respective drugs, FcεRIαECD-Fc2ST (IgE$_{TRAP}$) and XOLAIR™ (omalizumab), were prepared at each concentration, and then mixed with human IgE (1 ug/mL). Then, incubation was performed at room temperature for 30 minutes. During pre-incubation of the drug, a human FcεRI gene was introduced, and mast cells derived from and differentiated from mouse bone marrow, in which the mouse FcεRI gene had been removed, were prepared. The prepared mast cells were washed with HBSS buffer, and then 5×10$^5$ cells were injected into 60 μL of HBSS buffer. 20 μL of the pre-incubated sample was added to the prepared mast cells, and then incubated in a 5% CO$_2$ incubator at 37° C. for 30 minutes.

Subsequently, after 20 uL of anti-human IgE antibody (BioLegend, Cat No. 325502, 0.5 ug/mL) was added to induce a similar reaction to a foreign antigen, and then the resultant was incubated again in 5% CO$_2$ incubator at 37° C. for 30 minutes. Subsequently, after centrifugation at 1,500 rpm at 4° C., 30 uL of the supernatant was separated. 30 uL of the separated supernatant and 30 uL of the substrate (4-nitrophenyl N-acetyl-β-glucosaminide, 5.84 mM) were mixed well, and then incubated in a 5% CO$_2$ incubator at 37° C. for 25 minutes. Then, 140 uL of 0.1 M sodium carbonate buffer (pH 10) was added to terminate the reaction.

Subsequently, absorbance at 405 nm was measured to compare relative amounts of secreted β-hexosaminidase, and a mass cell-inhibitory effect depending on each drug concentration was identified. The results are shown in FIG. 15B. As shown in FIG. 15B, IC$_{50}$ of the FcεRIα ECD fusion protein was measured to be approximately 11.16 ng/mL, and IC$_{50}$ of the XOLAIR™ (omalizumab) protein was measured to be approximately 649.8 ng/mL. Therefore, it was identified that the FcεRIα ECD fusion protein has a 58-fold higher inhibitory ability on mast cell activity than XOLAIR™ (omalizumab).

Experimental Example 5. In Vivo Assay of FcεRIα ECD Fusion Protein: Food Allergy Model 50 ug of ovalbumin (OVA) and 1 mg of alum were intraperitoneally administered to Balb/c mice (Orientbio Inc.) two times at a 14-day interval to induce sensitization. Thereafter, 50 mg of OVA was orally administered five times in total on days 28, 30, 32, 34, and 36, to induce food allergy in intestines.

After the OVA was orally administered two times, that is, on day 31, the mice were divided into three groups, each containing 7 mice. The three divided groups were as follows: The first group receiving the FcεRIαECD-Fc2ST fusion protein at a high concentration (200 ug), the second group receiving the FcεRIαECD-Fc2ST fusion protein at a low concentration (20 ug), and the third group receiving nothing. While orally administering the OVA, it was identified whether diarrhea occurs due to food allergy induction. The mice were sacrificed on day 37, and the number of mast cells in the small intestine, the IgE concentration in blood, and the concentration of enzyme (mast cell protease-1 (MCPT-1)) of mast cell degranulation in blood were analyzed for the mice belonging to each group.

Figure 16:
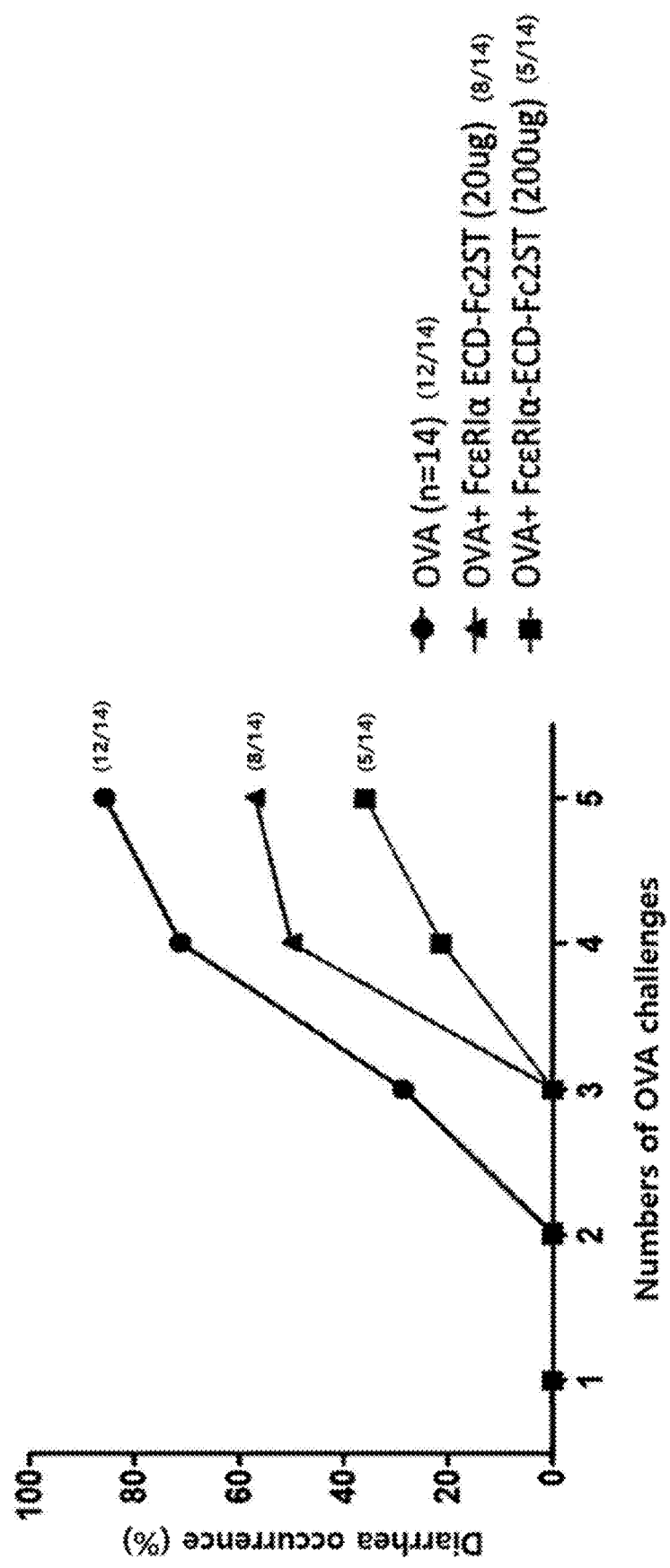
FIG. 16 illustrates potencies of a polypeptide dimeric protein according to an embodiment of the present invention in a food allergy-induced disease model.

As shown in FIG. 16, it was identified that the mice belonging to the group receiving the FcεRIαECD-Fc2ST, which is a polypeptide dimer, at a high concentration exhibits an effect of alleviating food allergy in a concentration-dependent manner, as compared with the mice belonging to the group receiving nothing.

II. Preparation of Combination of Polypeptide with Binding Ability to IgE and Probiotics, and Identification of its Effect Example 3: Culture and Administration of Probiotics

*L. casei* (*Lactobacillus casei*; KACC 12413), *Lc. lactis* (*Lactococcus lactis*; KACC 13877), *L. fermentum* (*Lactobacillus fermentum*; KACC 11441), and *L. rhamnosus* (*Lactobacillus rhamnosus*; KACC 11953) were inoculated on MRS broth or Brain Heart Infusion (BHI) medium and cultured in a 37° C. incubator (N-Biotek Cat #NB201L) for 24 hours. *L. reuteri* (*Lactobacillus reuteri*; KACC 11452) and *S. thermophiles* (*Streptococcus thermophiles*; KACC 11857) were cultured in a shaking incubator (N-biotek) at 37° C. and 50 rpm for 24 hours in view of their aerobic nature.

The cultured probiotics were dissolved in a lyophilization medium containing 10% skim milk and 10% sucrose, and lyophilized using a freeze dryer (Labcono). Then, the resultant was powdered. For the completed probiotics, a colony forming unit (cfu) present per gram was measured by serial dilution.

The lyophilized probiotics were continuously fed at $1 \times 10^9$ to $2.5 \times 10^9$ cfu per mouse using an oral zonde at 2- to 3-day intervals during the experiment. A negative control was fed an equal amount of lyophilized medium.

Example 4: Preparation of Composition Comprising Probiotics and Polypeptide with Binding Ability to IgE The polypeptide with a binding ability to IgE which had been obtained in Example 1 and the probiotics obtained in Example 3 were mixed to prepare a composition for treating allergy.

Experimental Example 6. Identification of Effect of FcεRIα-Fc Fusion Protein on Amelioration of Allergy 50 ug of ovalbumin (OVA) and 1 mg of alum were intraperitoneally administered to Balb/c mice (Orientbio Inc.) two times at a 14-day interval to induce sensitization. Thereafter, 50 mg of OVA was orally administered five times in total on days 28, 30, 32, 34, and 36, to induce food allergy in intestines. The mice in which food allergy had been induced were divided into five groups, each containing 7 mice. The five divided groups were as follows: The first group receiving an FcεRIαECD recombinant protein at a high concentration (200 ug), the second group receiving the FcεRIαECD recombinant protein at a low concentration (20 ug), the third group receiving the FcεRIαECD recombinant protein at a high concentration (200 ug) plus B. longum, the fourth group receiving the FcεRIαECD recombinant protein at a low concentration (20 ug) plus B. longum, and the fifth group receiving nothing.

While orally administering the OVA, it was identified whether diarrhea occurs due to food allergy induction. The mice were sacrificed on day 37, and the number of mast cells in the small intestine, the IgE concentration in blood, and the concentration of enzyme (mast cell protease-1 (MCPT-1)) with mast cell degranulation in blood were analyzed for the mice belonging to each group. As shown in FIG. 19B, it was found that the mice belonging to the group receiving a combination of the FcεRIαECD polypeptide dimer and B. longum exhibits an effect of alleviating food allergy as compared with the mice belonging to the group receiving nothing.

Experimental Example 7. Identification of Effect of Combined Administration of IgETRAP and Probiotics on Amelioration of Allergy In order to evaluate an effect of $IgE_{TRAP}$ on food allergy, dose-dependent acute diarrhea was induced in BALB/c mice to produce a mouse model with allergen-induced food allergy. Specifically, experiments were carried out in the same manner as in Experimental Example 6, except that $IgE_{TRAP}$, an FcεRIαECD recombinant protein, was administered at 100 ug/head. In addition, the probiotics B. longum was lyophilized and mixed with powdered mouse feed at $3 \times 10^9$ cfu/g. The mice were allowed ad libitum access to the feed. In order to maintain freshness, the mouse feed mixed with B. longum was replaced every 2 to 3 days. As a result, as shown in the following Table 6 and FIG. 18, it was found that an excellent allergy-alleviating effect was exhibited in the experiment group simultaneously receiving the probiotics B. longum and $IgE_{TRAP}$, an FcεRIαECD polypeptide dimer.

TABLE 6

| Group | Final number of mice | Characteristic feature | 1st OVA challenge | 2nd OVA challenge | 3rd OVA challenge | 4th OVA challenge | 5th OVA challenge |
|---|---|---|---|---|---|---|---|
| 1 | 17 | Disease Ctrl | 0/17 (0.00%) | 0/17 (0.00%) | 2/17 (11.76%) | 14/17 (82.35%) | 15/17 (88.24%) |
| 2 | 17 | B. longum only | 0/17 (0.00%) | 0/17 (0.00%) | 2/17 (11.11%) | 11/17 (61.11%) | 11/17 (64.71%) |
| 3 | 18 | IgE trap + B. longum | 0/18 (0.00%) | 0/18 (0.00%) | 1/18 (5.56%) | 2/18 (11.11%) | 4/18 (22.22%) |
| 4 | 17 | IgE trap only | 0/17 (0.00%) | 0/17 (0.00%) | 3/17 (17.65%) | 6/17 (35.29%) | 9/17 (52.94%) |
| 5 | 16 | Normal Ctrl | 0/16 (0.00%) | 0/16 (0.00%) | 0/16 (0.00%) | 0/16 (0.00%) | 0/16 (0.00%) |

Using this model, the present inventors have found that administration of $IgE_{TRAP}$ alone effectively decreased occurrence of diarrhea, and have identified that administration of $IgE_{TRAP}$ in combination with B. longum remarkably decreased occurrence of diarrhea as compared with the administration of $IgE_{TRAP}$ alone (FIG. 18). It has been reported that B. longum decreased the number of mast cells and alleviated food allergic symptoms through apoptosis. However, the group receiving intraperitoneal injection of $IgE_{TRAP}$ exhibited a better therapeutic effect than the group daily receiving B. longum (FIG. 18). Interestingly, even in a case where $IgE_{TRAP}$ with a 10-fold decreased concentration was used, a combination therapy of $IgE_{TRAP}$ and B. longum exhibited a similar effect to the $IgE_{TRAP}$-alone therapy (FIG. 19B).

Experimental Example 8. Identification of Effects at Time of Combined Administration of IgETRAP and B. longum: MCPT-1 and IgE Levels In addition, a level of serum MCPT-1 was measured to identify mast cell degranulation. Administration of $IgE_{TRAP}$ and B. longum alone did not decrease a level of MCPT-1, but a combination of $IgE_{TRAP}$ and B. longum significantly decreased a level of MCPT-1 (FIG. 20). Thus, it can be seen that *B. longum* and IgE$_{TRAP}$ cooperate to inhibit mast cell degranulation. In a food allergic mouse model, in order to investigate efficacy of a therapeutic agent that decreases IgE, ELISA was used to analyze levels of total IgE and free IgE in serum. IgE$_{TRAP}$, and the combination of IgE$_{TRAP}$ and *B. longum* slightly increased the level of total IgE (FIG. 21). However, IgE$_{TRAP}$, and the combination of IgE$_{TRAP}$ and *B. longum* greatly decreased the level of free IgE (FIG. 22). In contrast, administration of *B. longum* alone did not affect levels of total IgE and free IgE (FIGS. 21 and 22). Thus, IgE$_{TRAP}$ and *B. longum* alleviate food allergic symptoms in several ways, suggesting that this combination may exert an effective therapeutic effect on food allergy.

Experimental Example 9. Identification of Inhibitory Effect of Combination of IgETRAP and *B. longum* on Number of Mast Cells and Goblet Cell Hyperplasia In order to investigate whether IgE$_{TRAP}$ and *B. longum*, and a combination thereof decrease the number of mast cells, chloroacetate esterase activity was used to stain mast cells. The results showed that administration of IgE$_{TRAP}$ and *B. longum* alone remarkably decreased the number of mast cells, and a combination of the two was much more effective (FIGS. 23 and 24). It can be seen that the results for *B. longum* are consistent with those reported previously. Investigation was made on whether goblet cell hyperplasia induced by Th2 cytokine environment can be inhibited by IgE$_{TRAP}$, *B. longum*, and combination therapy thereof. As expected, it was identified that the size of goblet cells in the small intestine of the food allergic mice was increased, and that hyperplasia occurred as the number of cells increased (FIGS. 25 and 26).

It was identified that administration of IgE$_{TRAP}$ and *B. longum* remarkably decreased the size and number of goblet cells and this effect became greater in a case where IgE$_{TRAP}$ and *B. longum* were administered in combination (FIGS. 25 and 26). In addition, it was seen that mRNA expression of IL-33 tended to be decreased by IgE$_{TRAP}$ and *B. longum*, and this effect became significantly greater in a case of being administered in combination (FIG. 28). These results indicate that IgE$_{TRAP}$ and *B. longum* significantly inhibit the number of intestinal mast cells and goblet cell hyperplasia, and exhibit a further improved effect in a case of being administered in combination.

Experimental Example 10. Identification of Presence of IgETRAP in Serum after Oral Administration of IgETRAP to Mice IgE$_{TRAP}$ (300 ug) was orally administered to mice, and 2 hours later, serum is collected by retro-orbital blood collection. After being allowed to react at room temperature for 30 minutes, supernatant (serum) was obtained by centrifugation at 4° C. and 1,300 rpm for 15 minutes. A 96-well immuno plate was coated with an anti-FcεRI antibody (Abcam, ab54411) and allowed to react overnight at 4° C. The plate was washed with washing buffer (PBS containing 0.05% TWEEN®-20 (polysorbate 20)), and then blocking buffer (PBS containing 1% bovine serum albumin) was added thereto. The plate was allowed to react for 1 hour. The plate was washed again with the washing buffer, and a standard sample and a diluted mouse serum sample were added to the plate. The plate was allowed to react for 2 hours, and washed again with the washing buffer. An anti-human IgG4 Fc antibody (Abcam, ab99823) was added thereto and the plate was allowed to react for 1 hour. The plate was washed again with the washing buffer, and TMB substrate (Supmodics) was added thereto. After being allowed to react for 20 minutes while blocking the light, a stop reaction (1 M H$_2$SO$_4$) was added to stop the reaction. A concentration value was measured with a microplate reader (Epoch microplate spectrophotometer) by setting a wavelength to 450 nm. As a result, IgE$_{TRAP}$ was detected in the serum of normal mice (FIG. 35). From these results, it can be seen that in a case where an IgE$_{TRAP}$ protein is orally administered, the IgE$_{TRAP}$ protein is delivered into the serum via binding with FcRn in the mucosa, and thus a therapeutic effect can be exhibited.

Experimental Example 11. Identification of Effect Obtained by Combined Administration of IgETRAP and Various Probiotics in Food Allergy Model In order to evaluate an effect of IgE$_{TRAP}$ and probiotics on food allergy, dose-dependent acute diarrhea was induced in BALB/c mice to produce a mouse model with allergen-induced food allergy. Specifically, experiments were carried out in the same manner as in Experimental Example 7, except that IgE$_{TRAP}$, an FcεRIαECD recombinant protein, was intraperitoneally administered to mice at 100 ug/head as in the experiment schedule of FIG. 17. In addition, lyophilized probiotics were continuously fed at 1×10$^9$ to 2.5× 10$^9$ cfu per mouse using an oral zonde at 2- to 3-day intervals during the experiment, and a negative control was fed an equal amount of lyophilized medium.

The results obtained by identifying diarrhea frequency after administration of IgE$_{TRAP}$ and *L. casei* are illustrated in FIG. 29. The results obtained by identifying diarrhea frequency after administration of IgE$_{TRAP}$ and *Lc. lactis* are illustrated in FIG. 30. The results obtained by identifying diarrhea frequency after administration of IgE$_{TRAP}$ and *S. thermophilus* are illustrated in FIG. 31. The results obtained by identifying diarrhea frequency after administration of IgE$_{TRAP}$ and *L. rhamnosus* are illustrated in FIG. 32. The results obtained by identifying diarrhea frequency after administration of IgE$_{TRAP}$ and *L. reuteri* were illustrated in FIG. 33. The results obtained by identifying diarrhea frequency after administration of IgE$_{TRAP}$ and *L. fermentum* are illustrated in FIG. 34.

REFERENCE SIGNS LIST

*B. longum*: *Bifidobacterium longum*

OIT: Oral immunotherapy

PSA: Passive systemic anaphylaxis

SPR: Surface plasmon resonance

BLI: Bio-layer interferometry

BMMC: Bone marrow-derived mast cell cfu: Colony-forming unit

MCPT-1: Mast cell protease-1

OVA: Ovalbumin

Treg cell: Regulatory T cell

Th2 cell: Type 2 helper T cell

ILC2: Group 2 innate lymphoid cell.

The invention claimed is:

1. A method for treating or preventing an allergic disease of a subject in need thereof, comprising:
   a step of administering a probiotic to the subject; and
   a step of administering a polypeptide dimer,
   wherein the probiotic is *Bifidobacterium longum*,
   wherein the polypeptide dimer comprises two monomers, each of which comprises an extracellular domain of an alpha subunit of an IgE Fc receptor (FcεRIαECD),
   wherein each of the monomers comprises a modified Fc region,
   and wherein the modified Fc region and the FcεRIαECD are linked via a hinge, and wherein the hinge is Arg Asn Thr Gly Arg Gly Gly Glu Glu Lys Lys Xaa1 Xaa2 Lys Glu Lys Glu Glu Gln Glu Glu Arg Glu Thr Lys Thr Pro Glu Cys Pro (SEQ ID NO: 17) or Ala Gln Pro Gln Ala Glu Gly Ser Leu Ala Lys Ala Thr Thr Ala Pro Ala Thr Thr Arg Asn Thr Gly Arg Gly Gly Glu Glu Lys Lys Xaa3 Xaa4 Lys Glu Lys Glu Glu Gln Glu Glu Arg Glu Thr Lys Thr Pro Glu Cys Pro (SEQ ID NO: 18),
   Xaa1 and Xaa3 are Gly, and
   Xaa2 and Xaa4 are Gly or Ser.

2. The method according to claim 1, wherein the extracellular domain of the alpha subunit of the IgE Fc receptor (FcεRIαECD) comprises the amino acid sequence of SEQ ID NO: 1.

3. The method according to claim 1, wherein the probiotic is in the form of a dried powder.

4. The method according to claim 1, wherein the probiotic and the polypeptide dimer are in a form of a pharmaceutical composition, and the pharmaceutical composition further comprises a pharmaceutically acceptable carrier.

5. The method according to claim 1, wherein the probiotic and the polypeptide dimer are in a form of a dietary supplement or a foodstuff.

6. The method according to claim 1, wherein the probiotic is orally administered, and wherein the polypeptide dimer is parenterally administered.

* * * * *

SEQUENCE LISTING

<160> NUMBER OF SEQ ID NOS: 22

<210> SEQ ID NO 1
<211> LENGTH: 180
<212> TYPE: PRT
<213> ORGANISM: Artificial Sequence
<220> FEATURE:
<223> OTHER INFORMATION: FCeRI1 ECD

<400> SEQUENCE: 1

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
                20                  25                  30

Glu Val Ser Ser Thr Lys Trp Phe His Asn Gly Ser Leu Ser Glu Glu
            35                  40                  45

Thr Asn Ser Ser Leu Asn Ile Val Asn Ala Lys Phe Glu Asp Ser Gly
        50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln
            180

<210> SEQ ID NO 2
<211> LENGTH: 215
<212> TYPE: PRT
<213> ORGANISM: Artificial Sequence
<220> FEATURE:
<223> OTHER INFORMATION: Modified Fc

<400> SEQUENCE: 2

Ser His Thr Gln Pro Leu Gly Val Phe Leu Phe Pro Pro Lys Pro Lys
1               5                   10                  15

Asp Thr Leu Met Ile Ser Arg Thr Pro Glu Val Thr Cys Val Val Val
                20                  25                  30

Asp Val Ser Gln Glu Asp Pro Glu Val Gln Phe Asn Trp Tyr Val Asp
            35                  40                  45

Gly Val Glu Val His Asn Ala Lys Thr Lys Pro Arg Glu Glu Gln Phe
        50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

```
Glu Pro Gln Val Tyr Thr Leu Pro Ser Gln Glu Met Thr Lys
            115                 120                 125

Asn Gln Val Ser Leu Thr Cys Leu Val Lys Gly Phe Tyr Pro Ser Asp
130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Arg Leu Thr Val Asp Lys Ser Arg Trp Gln Gln Gly Asn Val Phe Ser
            180                 185                 190

Cys Ser Val Met His Glu Ala Leu His Asn His Tyr Thr Gln Lys Ser
            195                 200                 205

Leu Ser Leu Ser Leu Gly Lys
    210                 215

<210> SEQ ID NO 3
<211> LENGTH: 30
<212> TYPE: PRT
<213> ORGANISM: Artificial Sequence
<220> FEATURE:
<223> OTHER INFORMATION: IgD hinge variant

<400> SEQUENCE: 3

Arg Asn Thr Gly Arg Gly Gly Glu Glu Lys Lys Gly Ser Lys Glu Lys
1               5                   10                  15

Glu Glu Gln Glu Glu Arg Glu Thr Lys Thr Pro Glu Cys Pro
            20                  25                  30

<210> SEQ ID NO 4
<211> LENGTH: 49
<212> TYPE: PRT
<213> ORGANISM: Artificial Sequence
<220> FEATURE:
<223> OTHER INFORMATION: IgD hinge variant

<400> SEQUENCE: 4

Ala Gln Pro Gln Ala Glu Gly Ser Leu Ala Lys Ala Thr Thr Ala Pro
1               5                   10                  15

Ala Thr Thr Arg Asn Thr Gly Arg Gly Gly Glu Glu Lys Lys Gly Ser
            20                  25                  30

Lys Glu Lys Glu Glu Gln Glu Glu Arg Glu Thr Lys Thr Pro Glu Cys
            35                  40                  45

Pro

<210> SEQ ID NO 5
<211> LENGTH: 540
<212> TYPE: DNA
<213> ORGANISM: Artificial Sequence
<220> FEATURE:
<223> OTHER INFORMATION: nucleotides sequence of FCeRI1 ECD

<400> SEQUENCE: 5
gtgccccaga agcccaaggt gagcctgaac cctccctgga cagaatcttc caagggcgag      60
aacgtgaccc tgacctgcaa cggcaacaac ttcttcgagg tgagcagcac caagtggttc     120
cacaatggca gcctgagcga ggagaccaac agctccctga catcgtgaa cgccaagttc     180 gaggacagcg gcgagtacaa gtgccagcac cagcaggtga cgagagcga gcccgtgtac     240 ctggaggtgt tcagcgactg gctgctgctg caggccagcg ccgaggtggt gatggagggc     300 cagccctgt tcctgagatg ccacggctgg agaaactggg acgtgtacaa ggtgatctac     360
```

```
tacaaggatg gcgaggccct gaagtactgg tacgagaacc acaacatctc catcaccaac    420
gccaccgtgg aggacagcgg cacctactac tgcacaggca aggtgtggca gctggactac    480
gagagcgagc ccctgaacat caccgtgatc aaggctccca gagagaagta ctggctgcag    540
```

<210> SEQ ID NO 6
<211> LENGTH: 561
<212> TYPE: DNA
<213> ORGANISM: Artificial Sequence
<220> FEATURE:
<223> OTHER INFORMATION: nucleotides sequence of modified Fc

<400> SEQUENCE: 6

```
tgcgtggtcg tggatgtgag ccaggaagat cccgaagtgc agttcaactg gtacgtggat     60
ggcgtggaag tgcacaacgc caagaccaag cccagagaag agcagttcaa ctccacctac    120
agagtggtga gcgtgctgac cgtgctgcac caggactggc tgaacggcaa ggagtacaag    180
tgcaaggtgt ccaacaaagg cctgcccagc tccatcgaga agaccatcag caaagccaaa    240
ggccagccca gagaacccca ggtgtacacc ctgcctccca gccaggaaga gatgaccaag    300
aaccaggtgt ccctgacctg cctggtgaaa ggcttctacc ccagcgacat cgccgtggag    360
tgggaaagca acggccagcc cgagaacaat tacaagacaa cccctcccgt gctggatagc    420
gatggcagct ctttctgta cagcagactg accgtggaca gagcagatg gcaggaaggc    480 aacgtgttca gctgcagcgt gatgcacgaa gccctgcaca ccactacac ccagaagagc    540 ctgtccctga gcctgggcaa g                                               561
```

<210> SEQ ID NO 7
<211> LENGTH: 174
<212> TYPE: DNA
<213> ORGANISM: Artificial Sequence
<220> FEATURE:
<223> OTHER INFORMATION: nucleotides sequence of IgD hinge variant

<400> SEQUENCE: 7

```
aggaacaccg gcagaggagg cgaggaaaag aaaggaagca aggagaagga ggagcaggag     60
gaaagagaaa ccaagacccc cgagtgcccc agccacaccc agcccctggg cgtgttcctg    120
ttccccccca agcccaagga caccctgatg atcagcagaa ccccgaggt gacc            174
```

<210> SEQ ID NO 8
<211> LENGTH: 231
<212> TYPE: DNA
<213> ORGANISM: Artificial Sequence
<220> FEATURE:
<223> OTHER INFORMATION: nucleotides sequence of IgD hinge variant

<400> SEQUENCE: 8

```
gcccagcccc aggccgaggg cagcctggct aaggccacca cagctcccgc caccaccagg     60
aacaccggca gaggaggcga ggaaaagaaa ggaagcaagg agaaggagga gcaggaggaa    120
agagaaacca agacccccga gtgccccagc cacacccagc cctgggcgt gttcctgttc    180 cccccaagc caaggacac cctgatgatc agcagaaccc cgaggtgac c                 231
```

<210> SEQ ID NO 9
<211> LENGTH: 25
<212> TYPE: PRT
<213> ORGANISM: Artificial Sequence
<220> FEATURE:
<223> OTHER INFORMATION: signal peptide

```
<400> SEQUENCE: 9

Met Asp Ala Met Leu Arg Gly Leu Cys Cys Val Leu Leu Cys Gly
1               5                   10                  15

Ala Val Phe Val Ser Pro Ser His Ala
                20                  25

<210> SEQ ID NO 10
<211> LENGTH: 75
<212> TYPE: DNA
<213> ORGANISM: Artificial Sequence
<220> FEATURE:
<223> OTHER INFORMATION: nucleotides sequence of signal peptide

<400> SEQUENCE: 10
atggacgcca tgctgagagg cctgtgctgt gtgctgctgc tgtgcggcgc cgtgttcgtg    60
tcccctagcc acgcc                                                    75

<210> SEQ ID NO 11
<211> LENGTH: 450
<212> TYPE: PRT
<213> ORGANISM: Artificial Sequence
<220> FEATURE:
<223> OTHER INFORMATION: FceRIa ECD-hinge-Fc2

<400> SEQUENCE: 11

Met Asp Ala Met Leu Arg Gly Leu Cys Cys Val Leu Leu Cys Gly
1               5                   10                  15

Ala Val Phe Val Ser Pro Ser His Ala Val Pro Gln Lys Pro Lys Val
                20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Arg Asn Thr
        195                 200                 205

Gly Arg Gly Gly Glu Glu Lys Lys Gly Ser Lys Glu Lys Glu Glu Gln
    210                 215                 220

Glu Glu Arg Glu Thr Lys Thr Pro Glu Cys Pro Ser His Thr Gln Pro
225                 230                 235                 240

Leu Gly Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 12
<211> LENGTH: 1350
<212> TYPE: DNA
<213> ORGANISM: Artificial Sequence
<220> FEATURE:
<223> OTHER INFORMATION: nucleotides sequence of FceRIa ECD-hinge-Fc2

<400> SEQUENCE: 12
atggacgcca tgctgagagg cctgtgctgt gtgctgctgc tgtgcggcgc cgtgttcgtg      60
tcccctagcc acgccgtgcc ccagaagccc aaggtgagcc tgaaccctcc ctggaacaga     120
atcttcaagg gcgagaacgt gaccctgacc tgcaacggca caacttcttt cgaggtgagc     180
agcaccaagt ggttccacaa tggcagcctg agcgaggaga ccaacagctc cctgaacatc     240
gtgaacgcca agttcgagga cagcggcgag tacaagtgcc agcaccagca ggtgaacgag     300
agcgagcccg tgtacctgga ggtgttcagc gactggctgc tgctgcaggc cagcgccgag     360
gtggtgatgg agggccagcc cctgttcctg agatgccacg gctggagaaa ctgggacgtg     420
tacaaggtga tctactacaa ggatggcgag gccctgaagt actggtacga gaaccacaac     480
atctccatca ccaacgccac cgtggaggac agcggcacct actactgcac aggcaaggtg     540
tggcagctgg actacgagag cgagcccctg aacatcaccg tgatcaaggc tcccagagag     600
aagtactggc tgcagaggaa caccggcaga ggaggcgagg aaaagaaagg aagcaaggag     660
aaggaggagc aggaggaaag agaaaccaag accccgagt gccccagcca cccagccc     720 ctgggcgtgt tcctgttccc ccccaagccc aaggacaccc tgatgatcag cagaaccccc     780
gaggtgacct gcgtggtcgt ggatgtgagc caggaagatc ccgaagtgca gttcaactgg     840
tacgtggatg gcgtggaagt gcacaacgcc aagaccaagc ccagagaaga gcagttcaac     900
```

```
tccacctaca gagtggtgag cgtgctgacc gtgctgcacc aggactggct gaacggcaag    960
gagtacaagt gcaaggtgtc caacaaaggc ctgcccagct ccatcgagaa gaccatcagc   1020
aaagccaaag ccagcccag  agaaccccag gtgtacaccc tgcctcccag ccaggaagag   1080
atgaccaaga accaggtgtc cctgacctgc ctggtgaaag gcttctaccc cagcgacatc   1140
gccgtggagt gggaaagcaa cggccagccc gagaacaatt acaagacaac ccctcccgtg   1200
ctggatagcg atggcagctt ctttctgtac agcagactga ccgtggacaa gagcagatgg   1260
caggaaggca acgtgttcag ctgcagcgtg atgcacgaag ccctgcacaa ccactacacc   1320
cagaagagcc tgtccctgag cctgggcaag                                   1350
```

<210> SEQ ID NO 13
<211> LENGTH: 469
<212> TYPE: PRT
<213> ORGANISM: Artificial Sequence
<220> FEATURE:
<223> OTHER INFORMATION: FceRIa ECD-hinge-Fc3

<400> SEQUENCE: 13

```
Met Asp Ala Met Leu Arg Gly Leu Cys Cys Val Leu Leu Cys Gly
1               5                   10                  15

Ala Val Phe Val Ser Pro Ser His Ala Val Pro Gln Lys Pro Lys Val
                20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Ala Gln Pro
        195                 200                 205

Gln Ala Glu Gly Ser Leu Ala Lys Ala Thr Thr Ala Pro Ala Thr Thr
    210                 215                 220

Arg Asn Thr Gly Arg Gly Gly Glu Glu Lys Lys Gly Ser Lys Glu Lys
225                 230                 235                 240

Glu Glu Gln Glu Glu Arg Glu Thr Lys Thr Pro Glu Cys Pro Ser His
                245                 250                 255

Thr Gln Pro Leu Gly Val Phe Leu Phe Pro Pro Lys Pro Lys Asp Thr
            260                 265                 270

Leu Met Ile Ser Arg Thr Pro Glu Val Thr Cys Val Val Val Asp Val
```

```
                     275                 280                 285
Ser Gln Glu Asp Pro Glu Val Gln Phe Asn Trp Tyr Val Asp Gly Val
    290                 295                 300

Glu Val His Asn Ala Lys Thr Lys Pro Arg Glu Gln Phe Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Gly Leu Pro Ser
            340                 345                 350

Ser Ile Glu Lys Thr Ile Ser Lys Ala Lys Gly Gln Pro Arg Glu Pro
        355                 360                 365

Gln Val Tyr Thr Leu Pro Pro Ser Gln Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Arg Leu
            420                 425                 430

Thr Val Asp Lys Ser Arg Trp Gln Glu Gly Asn Val Phe Ser Cys Ser
        435                 440                 445

Val Met His Glu Ala Leu His Asn His Tyr Thr Gln Lys Ser Leu Ser
    450                 455                 460

Leu Ser Leu Gly Lys
465

<210> SEQ ID NO 14
<211> LENGTH: 1407
<212> TYPE: DNA
<213> ORGANISM: Artificial Sequence
<220> FEATURE:
<223> OTHER INFORMATION: nucleotides sequence of FceRIa ECD-hinge-Fc3

<400> SEQUENCE: 14
atggacgcca tgctgagagg cctgtgctgt gtgctgctgc tgtgcggcgc cgtgttcgtg    60
tcccctagcc acgccgtgcc ccagaagccc aaggtgagcc tgaaccctcc ctggaacaga   120
atcttcaagg gcgagaacgt gaccctgacc tgcaacggca caacttcttc cgaggtgagc   180
agcaccaagt ggttccacaa tggcagcctg agcgaggaga ccaacagctc cctgaacatc   240
gtgaacgcca gttcgagga cagcggcgag tacaagtgcc agcaccagca ggtgaacgag   300
agcgagcccg tgtacctgga ggtgttcagc gactggctgc tgctgcaggc cagcgccgag   360
gtggtgatgg agggccagcc cctgttcctg agatgccacg ctggagaaa ctgggacgtg   420 tacaaggtga tctactacaa ggatggcgag gccctgaagt actggtacga gaaccacaac   480
atctccatca ccaacgccac cgtggaggac agcggcacct actactgcac aggcaaggtg   540
tggcagctgg actacgagag cgagcccctg aacatcaccg tgatcaaggc tcccagagag   600
aagtactggc tgcaggccca gccccaggcc gagggcagcc tggctaaggc caccacagct   660
cccgccacca ccaggaacac cggcagagga ggcgaggaaa agaaaggaag caaggagaag   720
gaggagcagg aggaaagaga accaagacc cccgagtgcc cagccacac ccagcccctg   780 ggcgtgttcc tgttccccc caagcccaag gacaccctga tgatcagcag aacccccgag   840
gtgacctgcg tggtcgtgga tgtgagccag gaagatcccg aagtgcagtt caactggtac   900
gtggatggcg tggaagtgca caacgccaag accaagccca gagaagagca gttcaactcc   960
```

```
acctacagag tggtgagcgt gctgaccgtg ctgcaccagg actggctgaa cggcaaggag   1020
tacaagtgca aggtgtccaa caaaggcctg cccagctcca tcgagaagac catcagcaaa   1080
gccaaaggcc agcccagaga accccaggtg tacaccctgc ctcccagcca ggaagagatg   1140
accaagaacc aggtgtccct gacctgcctg gtgaaaggct tctacccag cgacatcgcc    1200 gtggagtggg aaagcaacgg ccagcccgag aacaattaca agacaacccc tcccgtgctg   1260
gatagcgatg gcagcttctt tctgtacagc agactgaccg tggacaagag cagatggcag   1320
gaaggcaacg tgttcagctg cagcgtgatg cacgaagccc tgcacaacca ctacacccag   1380
aagagcctgt ccctgagcct gggcaag                                       1407
```

```
<210> SEQ ID NO 15
<211> LENGTH: 406
<212> TYPE: PRT
<213> ORGANISM: Artificial Sequence
<220> FEATURE:
<223> OTHER INFORMATION: human a-2,6 sialic acid transferase

<400> SEQUENCE: 15
```

| | | | | | | | | | | | | | | |
|---|---|---|---|---|---|---|---|---|---|---|---|---|---|---|
| Met | Ile | His | Thr | Asn | Leu | Lys | Lys | Phe | Ser | Cys | Cys | Val | Leu | Val |
| 1 | | | | 5 | | | | | 10 | | | | | 15 |
| Phe | Leu | Leu | Phe | Ala | Val | Ile | Cys | Val | Trp | Lys | Glu | Lys | Lys | Gly |
| | | | | 20 | | | | | 25 | | | | | 30 |
| Ser | Tyr | Tyr | Asp | Ser | Phe | Lys | Leu | Gln | Thr | Lys | Glu | Phe | Gln | Val | Leu |
| | | | 35 | | | | | 40 | | | | | 45 | | |
| Lys | Ser | Leu | Gly | Lys | Leu | Ala | Met | Gly | Ser | Asp | Ser | Gln | Ser | Val | Ser |
| | 50 | | | | | 55 | | | | | 60 | | | | |
| Ser | Ser | Ser | Thr | Gln | Asp | Pro | His | Arg | Gly | Arg | Gln | Thr | Leu | Gly | Ser |
| 65 | | | | | 70 | | | | | 75 | | | | | 80 |
| Leu | Arg | Gly | Leu | Ala | Lys | Ala | Lys | Pro | Glu | Ala | Ser | Phe | Gln | Val | Trp |
| | | | | 85 | | | | | 90 | | | | | 95 | |
| Asn | Lys | Asp | Ser | Ser | Ser | Lys | Asn | Leu | Ile | Pro | Arg | Leu | Gln | Lys | Ile |
| | | | | 100 | | | | | 105 | | | | | 110 | |
| Trp | Lys | Asn | Tyr | Leu | Ser | Met | Asn | Lys | Tyr | Lys | Val | Ser | Tyr | Lys | Gly |
| | | | | 115 | | | | | 120 | | | | | 125 | |
| Pro | Gly | Pro | Gly | Ile | Lys | Phe | Ser | Ala | Glu | Ala | Leu | Arg | Cys | His | Leu |
| | 130 | | | | | 135 | | | | | 140 | | | | |
| Arg | Asp | His | Val | Asn | Val | Ser | Met | Val | Glu | Val | Thr | Asp | Phe | Pro | Phe |
| 145 | | | | | 150 | | | | | 155 | | | | | 160 |
| Asn | Thr | Ser | Glu | Trp | Glu | Gly | Tyr | Leu | Pro | Lys | Glu | Ser | Ile | Arg | Thr |
| | | | | 165 | | | | | 170 | | | | | 175 | |
| Lys | Ala | Gly | Pro | Trp | Gly | Arg | Cys | Ala | Val | Val | Ser | Ser | Ala | Gly | Ser |
| | | | 180 | | | | | 185 | | | | | 190 | | |
| Leu | Lys | Ser | Ser | Gln | Leu | Gly | Arg | Glu | Ile | Asp | Asp | His | Asp | Ala | Val |
| | 195 | | | | | 200 | | | | | 205 | | | | |
| Leu | Arg | Phe | Asn | Gly | Ala | Pro | Thr | Ala | Asn | Phe | Gln | Gln | Asp | Val | Gly |
| 210 | | | | | 215 | | | | | 220 | | | | | |
| Thr | Lys | Thr | Thr | Ile | Arg | Leu | Met | Asn | Ser | Gln | Leu | Val | Thr | Thr | Glu |
| 225 | | | | | 230 | | | | | 235 | | | | | 240 |
| Lys | Arg | Phe | Leu | Lys | Asp | Ser | Leu | Tyr | Asn | Glu | Gly | Ile | Leu | Ile | Val |
| | | | | 245 | | | | | 250 | | | | | 255 | |
| Trp | Asp | Pro | Ser | Val | Tyr | His | Ser | Asp | Ile | Pro | Lys | Trp | Tyr | Gln | Asn |
| | | | 260 | | | | | 265 | | | | | 270 | | |
| Pro | Asp | Tyr | Asn | Phe | Phe | Asn | Asn | Tyr | Lys | Thr | Tyr | Arg | Lys | Leu | His |

```
                275                 280                 285
Pro Asn Gln Pro Phe Tyr Ile Leu Lys Pro Gln Met Pro Trp Glu Leu
            290                 295                 300
Trp Asp Ile Leu Gln Glu Ile Ser Pro Glu Glu Ile Gln Pro Asn Pro
305                 310                 315                 320
Pro Ser Ser Gly Met Leu Gly Ile Ile Met Met Thr Leu Cys Asp
                325                 330                 335
Gln Val Asp Ile Tyr Glu Phe Leu Pro Ser Lys Arg Lys Thr Asp Val
            340                 345                 350
Cys Tyr Tyr Tyr Gln Lys Phe Asp Ser Ala Cys Thr Met Gly Ala
                355                 360                 365
Tyr His Pro Leu Leu Tyr Glu Lys Asn Leu Val Lys His Leu Asn Gln
            370                 375                 380
Gly Thr Asp Glu Asp Ile Tyr Leu Leu Gly Lys Ala Thr Leu Pro Gly
385                 390                 395                 400
Phe Arg Thr Ile His Cys
                405

<210> SEQ ID NO 16
<211> LENGTH: 1218
<212> TYPE: DNA
<213> ORGANISM: Artificial Sequence
<220> FEATURE:
<223> OTHER INFORMATION: nucleotides sequence of human a-2,6 sialic acid
      transferase

<400> SEQUENCE: 16
atgatccaca ccaacctgaa gaagaagttc agctgctgcg tgctggtgtt cctgctgttc      60
gccgtgatct gcgtgtggaa ggagaagaag aaaggcagct actacgacag cttcaagctg     120
cagaccaagg agttccaggt gctgaagagc ctgggcaagc tggccatggg cagcgacagc     180
cagagcgtgt ccagctcctc cacccaggat ccccacagag gcagacagac cctgggcagc     240
ctgagaggcc tggccaaggc caagcccgag gccagcttcc aggtgtggaa caaggacagc     300
agcagcaaga acctgatccc cagactgcag aagatctgga gaactaccct gagcatgaac     360
aagtacaagg tgagctacaa ggaccccgga cccggcatca gttcagcgc cgaggccctg     420 aggtgccacc tgagagacca cgtgaacgtg agcatggtgg aagtgaccga cttccccttc     480
aacaccagcg agtgggaagg ctacctgccc aaggagagca tcaggaccaa ggctggcccc     540
tggggcagat cgccgtggt gagcagcgct ggcagcctga gagctcccca gctgggcaga     600
gagatcgacg accacgatgc cgtgctgagg ttcaatggcg ctcccaccgc caacttccag     660
caggacgtgg gcaccaagac cacaatccgg ctgatgaaca gccagctggt gacaaccgag     720
aagcggttcc tgaaggacag cctgtacaac gagggcatcc tgatcgtgtg ggatcccagc     780
gtgtaccaca gcgacatccc caagtggtac cagaatcccg actacaactt cttcaacaac     840
tacaagacct atagaaagct gcaccccaac cagcccttct acatcctgaa gccccagatg     900
ccctgggagc tgtgggacat cctgcaggag atcagccctg aagagatcca gcccaaccct     960
ccctccagcg gcatgctggg cattatcatc atgatgaccc tgtgcgacca ggtgacatc    1020 tacgagttcc tgcccagcaa gagaaagacc gacgtgtgct actactatca gaagttcttc    1080
gacagcgcct gcaccatggg cgcctaccac cccctgctgt acgagaagaa cctggtgaag    1140
cacctgaacc agggcaccga cgaggacatc tacctgctgg gcaaagccac cctgcccggc    1200
ttcagaacca tccactgc                                                   1218
```

```
<210> SEQ ID NO 17
<211> LENGTH: 30
<212> TYPE: PRT
<213> ORGANISM: Artificial Sequence
<220> FEATURE:
<223> OTHER INFORMATION: IgD hinge variant
<220> FEATURE:
<221> NAME/KEY: Xaa is Lys or Gly
<222> LOCATION: (12)..(12)
<220> FEATURE:
<221> NAME/KEY: Xaa is Glu, Gly, or Ser
<222> LOCATION: (13)..(13)

<400> SEQUENCE: 17

Arg Asn Thr Gly Arg Gly Gly Glu Glu Lys Lys Xaa Xaa Lys Glu Lys
1               5                   10                  15

Glu Glu Gln Glu Glu Arg Glu Thr Lys Thr Pro Glu Cys Pro
            20                  25                  30

<210> SEQ ID NO 18
<211> LENGTH: 49
<212> TYPE: PRT
<213> ORGANISM: Artificial Sequence
<220> FEATURE:
<223> OTHER INFORMATION: IgD hinge variant
<220> FEATURE:
<221> NAME/KEY: Xaa is Lys or Gly
<222> LOCATION: (31)..(31)
<220> FEATURE:
<221> NAME/KEY: Xaa is Glu, Gly, or Ser
<222> LOCATION: (32)..(32)

<400> SEQUENCE: 18

Ala Gln Pro Gln Ala Glu Gly Ser Leu Ala Lys Ala Thr Thr Ala Pro
1               5                   10                  15

Ala Thr Thr Arg Asn Thr Gly Arg Gly Gly Glu Glu Lys Lys Xaa Xaa
            20                  25                  30

Lys Glu Lys Glu Glu Gln Glu Glu Arg Glu Thr Lys Thr Pro Glu Cys
        35                  40                  45

Pro

<210> SEQ ID NO 19
<211> LENGTH: 30
<212> TYPE: PRT
<213> ORGANISM: Artificial Sequence
<220> FEATURE:
<223> OTHER INFORMATION: IgD hinge

<400> SEQUENCE: 19

Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro
            20                  25                  30

<210> SEQ ID NO 20
<211> LENGTH: 425
<212> TYPE: PRT
<213> ORGANISM: Artificial Sequence
<220> FEATURE:
<223> OTHER INFORMATION: FceRIa ECD-hinge-Fc1

<400> SEQUENCE: 20

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
```

```
           20                  25                  30
Glu Val Ser Ser Thr Lys Trp Phe His Asn Gly Ser Leu Ser Glu Glu
            35                  40                  45

Thr Asn Ser Ser Leu Asn Ile Val Asn Ala Lys Phe Glu Asp Ser Gly
 50                  55                  60

Glu Tyr Lys Cys Gln His Gln Gln Val Asn Glu Ser Glu Pro Val Tyr
 65                  70                  75                  80

Leu Glu Val Phe Ser Asp Trp Leu Leu Leu Gln Ala Ser Ala Glu Val
                 85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
            115                 120                 125

Tyr Trp Tyr Glu Asn His Asn Ile Ser Ile Thr Asn Ala Thr Val Glu
            130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Arg Asn Thr Gly Arg Gly Glu Glu Lys Lys Lys
            180                 185                 190

Glu Lys Glu Lys Glu Glu Gln Glu Arg Glu Thr Lys Thr Pro Glu
            195                 200                 205

Cys Pro Ser His Thr Gln Pro Leu Gly Val Phe Leu Phe Pro Pro Lys
            210                 215                 220

Pro Lys Asp Thr Leu Met Ile Ser Arg Thr Pro Glu Val Thr Cys Val
225                 230                 235                 240

Val Val Asp Val Ser Gln Glu Asp Pro Glu Val Gln Phe Asn Trp Tyr
                245                 250                 255

Val Asp Gly Val Glu Val His Asn Ala Lys Thr Lys Pro Arg Glu Glu
            260                 265                 270

Gln Phe Asn Ser Thr Tyr Arg Val Val Ser Val Leu Thr Val Leu His
            275                 280                 285

Gln Asp Trp Leu Asn Gly Lys Glu Tyr Lys Cys Lys Val Ser Asn Lys
            290                 295                 300

Gly Leu Pro Ser Ser Ile Glu Lys Thr Ile Ser Lys Ala Lys Gly Gln
305                 310                 315                 320

Pro Arg Glu Pro Gln Val Tyr Thr Leu Pro Pro Ser Gln Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
            355                 360                 365

Tyr Lys Thr Thr Pro Pro Val Leu Asp Ser Asp Gly Ser Phe Phe Leu
            370                 375                 380

Tyr Ser Arg Leu Thr Val Asp Lys Ser Arg Trp Gln Glu Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Leu Gly Lys
            420                 425

<210> SEQ ID NO 21
```

<211> LENGTH: 425
<212> TYPE: PRT
<213> ORGANISM: Artificial Sequence
<220> FEATURE:
<223> OTHER INFORMATION: FceRIa ECD-hinge-Fc2

<400> SEQUENCE: 21

```
Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
                20                  25                  30

Glu Val Ser Ser Thr Lys Trp Phe His Asn Gly Ser Leu Ser Glu Glu
            35                  40                  45

Thr Asn Ser Ser Leu Asn Ile Val Asn Ala Lys Phe Glu Asp Ser Gly
    50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
                100                 105                 110

Trp Asp Val Tyr Lys Val Ile Tyr Tyr Lys Asp Gly Glu Ala Leu Lys
            115                 120                 125

Tyr Trp Tyr Glu Asn His Asn Ile Ser Ile Thr Asn Ala Thr Val Glu
    130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Arg Asn Thr Gly Arg Gly Glu Glu Lys Lys Gly
            180                 185                 190

Ser Lys Glu Lys Glu Glu Gln Glu Arg Glu Thr Lys Thr Pro Glu
    195                 200                 205

Cys Pro Ser His Thr Gln Pro Leu Gly Val Phe Leu Phe Pro Pro Lys
210                 215                 220

Pro Lys Asp Thr Leu Met Ile Ser Arg Thr Pro Glu Val Thr Cys Val
225                 230                 235                 240

Val Val Asp Val Ser Gln Glu Asp Pro Glu Val Gln Phe Asn Trp Tyr
                245                 250                 255

Val Asp Gly Val Glu Val His Asn Ala Lys Thr Lys Pro Arg Glu Glu
            260                 265                 270

Gln Phe Asn Ser Thr Tyr Arg Val Val Ser Val Leu Thr Val Leu His
    275                 280                 285

Gln Asp Trp Leu Asn Gly Lys Glu Tyr Lys Cys Lys Val Ser Asn Lys
290                 295                 300

Gly Leu Pro Ser Ser Ile Glu Lys Thr Ile Ser Lys Ala Lys Gly Gln
305                 310                 315                 320

Pro Arg Glu Pro Gln Val Tyr Thr Leu Pro Pro Ser Gln Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
    355                 360                 365

Tyr Lys Thr Thr Pro Pro Val Leu Asp Ser Asp Gly Ser Phe Phe Leu
370                 375                 380
```

```
Tyr Ser Arg Leu Thr Val Asp Lys Ser Arg Trp Gln Glu Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Leu Gly Lys
                420                 425

<210> SEQ ID NO 22
<211> LENGTH: 444
<212> TYPE: PRT
<213> ORGANISM: Artificial Sequence
<220> FEATURE:
<223> OTHER INFORMATION: FceRIa ECD-hinge-Fc3

<400> SEQUENCE: 22

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
                20                  25                  30

Glu Val Ser Ser Thr Lys Trp Phe His Asn Gly Ser Leu Ser Glu Glu
            35                  40                  45

Thr Asn Ser Ser Leu Asn Ile Val Asn Ala Lys Phe Glu Asp Ser Gly
        50                  55                  60

Glu Tyr Lys Cys Gln His Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
                100                 105                 110

Trp Asp Val Tyr Lys Val Ile Tyr Tyr Lys Asp Gly Glu Ala Leu Lys
            115                 120                 125

Tyr Trp Tyr Glu Asn His Asn Ile Ser Ile Thr Asn Ala Thr Val Glu
        130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Ala Gln Pro Gln Ala Glu Gly Ser Leu Ala Lys Ala
            180                 185                 190

Thr Thr Ala Pro Ala Thr Thr Arg Asn Thr Gly Arg Gly Gly Glu Glu
        195                 200                 205

Lys Lys Gly Ser Lys Glu Lys Glu Glu Glu Glu Arg Glu Thr Lys
            210                 215                 220

Thr Pro Glu Cys Pro Ser His Thr Gln Pro Leu Gly Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320
```

```
Ser Asn Lys Gly Leu Pro Ser Ser Ile Glu Lys Thr Ile Ser Lys Ala
            325             330             335

Lys Gly Gln Pro Arg Glu Pro Gln Val Tyr Thr Leu Pro Pro Ser Gln
        340             345             350

Glu Glu Met Thr Lys Asn Gln Val Ser Leu Thr Cys Leu Val Lys Gly
        355             360             365

Phe Tyr Pro Ser Asp Ile Ala Val Glu Trp Glu Ser Asn Gly Gln Pro
    370             375             380

Glu Asn Asn Tyr Lys Thr Thr Pro Pro Val Leu Asp Ser Asp Gly Ser
385             390             395             400

Phe Phe Leu Tyr Ser Arg Leu Thr Val Asp Lys Ser Arg Trp Gln Glu
            405             410             415

Gly Asn Val Phe Ser Cys Ser Val Met His Glu Ala Leu His Asn His
            420             425             430

Tyr Thr Gln Lys Ser Leu Ser Leu Ser Leu Gly Lys
        435             440
```